US012239715B2

(12) United States Patent
Hanson et al.

(10) Patent No.: US 12,239,715 B2
(45) Date of Patent: *Mar. 4, 2025

(54) PEPTIDE OLIGONUCLEOTIDE CONJUGATES

(71) Applicant: Sarepta Therapeutics, Inc., Cambridge, MA (US)

(72) Inventors: Gunnar J. Hanson, Cambridge, MA (US); Ming Zhou, Cambridge, MA (US)

(73) Assignee: Sarepta Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/296,697

(22) Filed: Apr. 6, 2023

(65) Prior Publication Data

US 2023/0310625 A1   Oct. 5, 2023

Related U.S. Application Data

(63) Continuation of application No. 17/403,403, filed on Aug. 16, 2021, now Pat. No. 11,672,871, which is a continuation of application No. 16/860,292, filed on Apr. 28, 2020, now Pat. No. 11,097,011, which is a continuation of application No. 15/574,734, filed as application No. PCT/US2016/033276 on May 19, 2016, now Pat. No. 10,675,356.

(60) Provisional application No. 62/337,536, filed on May 17, 2016, provisional application No. 62/163,960, filed on May 19, 2015.

(51) Int. Cl.
| | | |
|---|---|---|
| A61K 47/64 | (2017.01) | |
| A61K 47/18 | (2017.01) | |
| C07K 7/06 | (2006.01) | |
| C07K 7/08 | (2006.01) | |
| A61K 38/00 | (2006.01) | |

(52) U.S. Cl.
CPC ............ *A61K 47/645* (2017.08); *A61K 47/18* (2013.01); *C07K 7/06* (2013.01); *C07K 7/08* (2013.01); *A61K 38/00* (2013.01); *Y02A 50/30* (2018.01)

(58) Field of Classification Search
CPC ...... A61K 47/645; A61K 47/18; A61K 38/00; C07K 7/08; C07K 7/06; Y02A 50/385
See application file for complete search history.

(56) References Cited

U.S. PATENT DOCUMENTS

| | | | | |
|---|---|---|---|---|
| 10,675,356 B2* | 6/2020 | Hanson | ................ | C07K 7/08 |
| 11,097,011 B2* | 8/2021 | Hanson | ................ | C07K 7/06 |
| 11,672,871 B2* | 6/2023 | Hanson | ................ | C07K 7/08 |
| | | | | 424/193.1 |
| 2002/0156235 A1 | 10/2002 | Manoharan et al. | | |
| 2011/0269665 A1 | 11/2011 | Kole | | |
| 2013/0190390 A1 | 7/2013 | Sazani et al. | | |
| 2014/0024821 A1 | 1/2014 | Kole et al. | | |
| 2014/0303238 A1 | 10/2014 | Linsley et al. | | |

FOREIGN PATENT DOCUMENTS

| | | |
|---|---|---|
| EP | 2623507 A1 | 8/2013 |
| JP | 2012-506703 A | 3/2012 |
| JP | 2014-513946 A | 6/2014 |
| JP | 2014-515762 A | 7/2014 |
| JP | 2015-501817 A | 1/2015 |
| WO | WO 2010/048586 A1 | 4/2010 |
| WO | WO 2012/144906 A1 | 10/2012 |
| WO | WO 2012/150960 A1 | 11/2012 |
| WO | WO 2013/086441 A2 | 6/2013 |
| WO | WO 2014/144978 A2 | 9/2014 |
| WO | WO 2016/138534 A2 | 9/2016 |

OTHER PUBLICATIONS

U.S. Appl. No. 15/574,734, filed Nov. 16, 2017, 2018-0214567 A1, Aug. 2, 2018, U.S. Pat. No. 10,675,356, dated Jun. 9, 2020, Gunnar J. Hanson.
U.S. Appl. No. 16/860,292, filed Apr. 28, 2020, 2020-0254109 A1, Aug. 12, 2020, U.S. Pat. No. 11,097,011, dated Aug. 24, 2021, Gunnar J. Hanson.
U.S. Appl. No. 17/403,403, filed Aug. 16, 2021, 2022-0072143 A1, Mar. 10, 2022, Gunnar J. Hanson.
U.S. Appl. No. 18/296,697, filed Apr. 6, 2023, Gunnar J. Hanson.
Bowie et al., "Deciphering the message in protein sequences: tolerance to amino acid substitutions", *Science* 247(4948):1306-1310 (1990).
Burgess et al., "Possible dissociation of the heparin-binding and mitogenic activities of heparin-binding (acidic fibroblast) growth factor-1 from its receptor-binding activities by site-directed mutagenesis of a single lysine residue", *Journal of Cell Biology* 111(5):2129-2138 (1990).
Extended European Search Report for European Application No. 16797300.7, dated Oct. 18, 2018.
International Search Report with Written Opinion corresponding to International Patent Application No. PCT/US2016/033276, mailed Aug. 26, 2016.
Jarver et al. (2011) "Peptide-mediated Cell and In Vivo Delivery of Antisense Oligonucleotides and siRNA", *Molecular Therapy-Nucleic Acids*, 1(6):e27, 17 pages.
Lazar et al., "Transforming growth factor alpha: mutation of aspartic acid 47 and leucine 48 results in different biological activities", *Molecular and Cellular Biology* 8(3):1247-1252 (1988).
Spokoyny et al. (2013) "A Perfluoroaryl-Cysteine SNAr Chemistry Approach to Unprotected Peptide Stapling", *Journal of the American Chemical Society*, 135:5946-5949.
Zhou et al. (2014) "Convergent diversity-oriented side-chain macrocyclization scan for unprotected polypeptides", *Organic and Biomolecular Chemistry*, 12:566-573.

* cited by examiner

Primary Examiner — Sudhakar Katakam
(74) *Attorney, Agent, or Firm* — Sterne, Kessler, Goldstein & Fox P.L.L.C.

(57) ABSTRACT

Provided herein are oligonucleotides, peptides, and peptide-oligonucleotide-conjugates. Also provided herein are methods of treating a muscle disease, a viral infection, or a bacterial infection in a subject in need thereof, comprising administering to the subject oligonucleotides, peptides, and peptide-oligonucleotide-conjugates described herein.

27 Claims, 13 Drawing Sheets

PEPTIDE OLIGONUCLEOTIDE CONJUGATES

RELATED APPLICATIONS

This application claims priority to U.S. patent application Ser. No. 17/403,403, filed on Aug. 16, 2021, which application claims priority to U.S. patent application Ser. No. 16/860,292, filed on Apr. 28, 2020, now U.S. Pat. No. 11,097,011, which application claims priority to U.S. patent application Ser. No. 15/574,734, filed Nov. 16, 2017, now U.S. Pat. No. 10,675,356, which application is a national stage entry of PCT/US2016/033276, filed May 19, 2016, which application claims priority to U.S. Provisional Patent Application No. 62/337,536, filed on May 17, 2016, and U.S. Provisional Patent Application No. 62/163,960, filed on May 19, 2015. The entire contents of these applications are herein incorporated by reference.

SEQUENCE LISTING

The present application is being filed along with a Sequence Listing in computer readable format. The Sequence Listing is provided as a file entitled 4140_0930005_SequenceListing_ST26.xml created Nov. 7, 2024, which is 21,439 bytes in size. The information in the computer readable format of the sequence listing is incorporated herein by reference in its entirety.

BACKGROUND

Antisense technology provides a means for modulating the expression of one or more specific gene products, including alternative splice products, and is uniquely useful in a number of therapeutic, diagnostic, and research applications. The principle behind antisense technology is that an antisense compound, e.g., an oligonucleotide, which hybridizes to a target nucleic acid, modulates gene expression activities such as transcription, splicing or translation through any one of a number of antisense mechanisms. The sequence specificity of antisense compounds makes them attractive as tools for target validation and gene functionalization, as well as therapeutics to selectively modulate the expression of genes involved in disease.

Although significant progress has been made in the field of antisense technology, there remains a need in the art for oligonucleotides, and peptide-oligonucleotide-conjugates with improved antisense or antigene performance. Such improved antisense or antigene performance includes, at least, for example: lower toxicity, stronger affinity for DNA and RNA without compromising sequence selectivity, improved pharmacokinetics and tissue distribution, improved cellular delivery, and both reliable and controllable in vivo distribution.

SUMMARY

Provided herein are peptides, oligonucleotides, and peptide-oligonucleotide-conjugates. Also provided herein are methods of treating a disease in a subject in need thereof, comprising administering to the subject a peptide-oligonucleotide-conjugate described herein.

Accordingly, in one aspect, provided herein is a peptide-oligonucleotide-conjugate of Formula I:

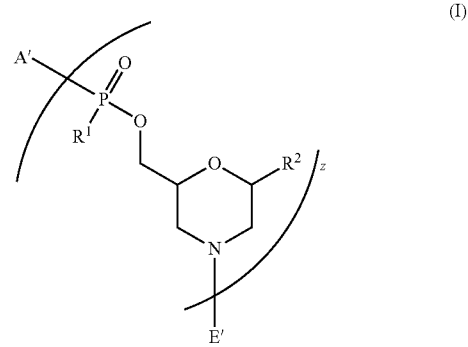

(I)

or a pharmaceutically acceptable salt thereof,

In one embodiment, the peptide-oligonucleotide-conjugate of Formula I is a peptide-oligonucleotide-conjugate of Formula Ia:

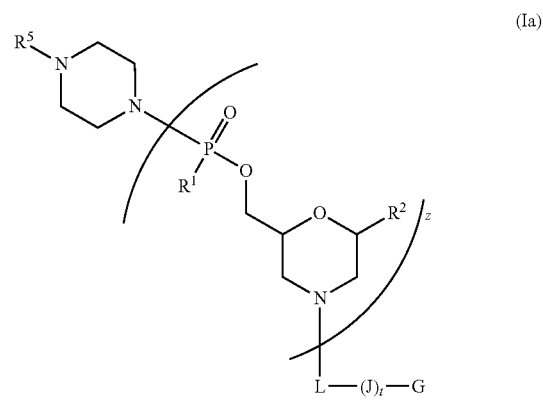

(Ia)

or a pharmaceutically acceptable salt thereof

In another embodiment, the peptide-oligonucleotide-conjugate of Formula I is a peptide-oligonucleotide-conjugate of Formula Ib:

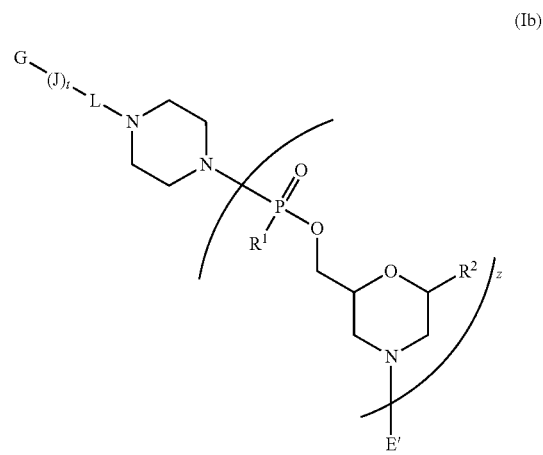

(Ib)

or a pharmaceutically acceptable salt thereof.

In still another embodiment, the peptide-oligonucleotide-conjugate of Formula I is a peptide-oligonucleotide-conjugate of Formula Ic:

(Ic)

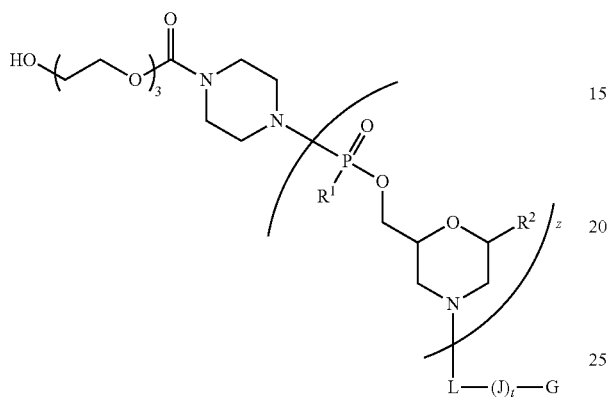

or a pharmaceutically acceptable salt thereof.

In yet another embodiment, the peptide-oligonucleotide-conjugate of Formula I is a peptide-oligonucleotide-conjugate of Formula Id:

(Id)

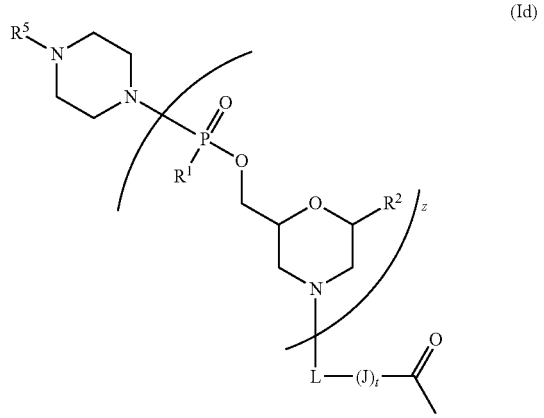

or a pharmaceutically acceptable salt thereof.

In still another embodiment, the peptide-oligonucleotide-conjugate of Formula I is a peptide-oligonucleotide-conjugate of Formula Ie:

(Ie)

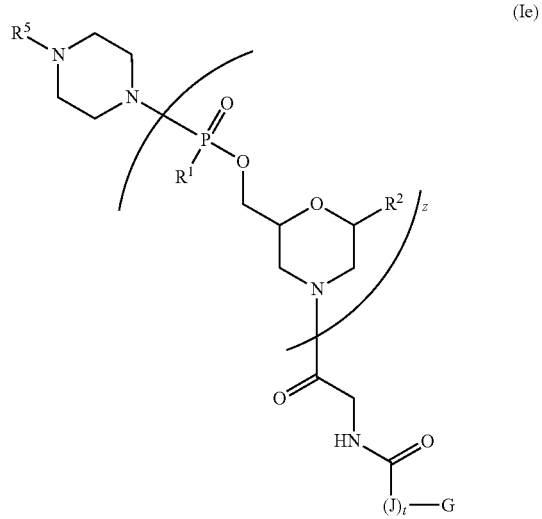

or a pharmaceutically acceptable salt thereof.

In another aspect, provided herein is a peptide-oligonucleotide-conjugate of Formula IV:

(IV)

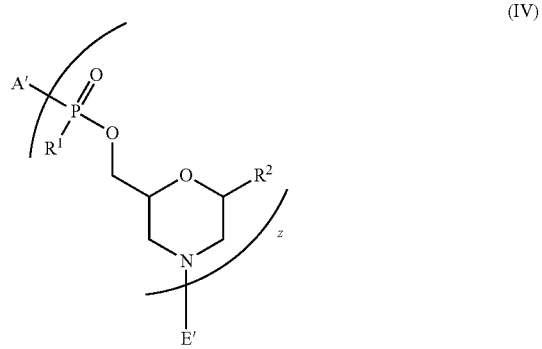

or a pharmaceutically acceptable salt thereof

In another aspect, provided herein is a peptide-oligonucleotide-conjugate of Formula IV:

(V)

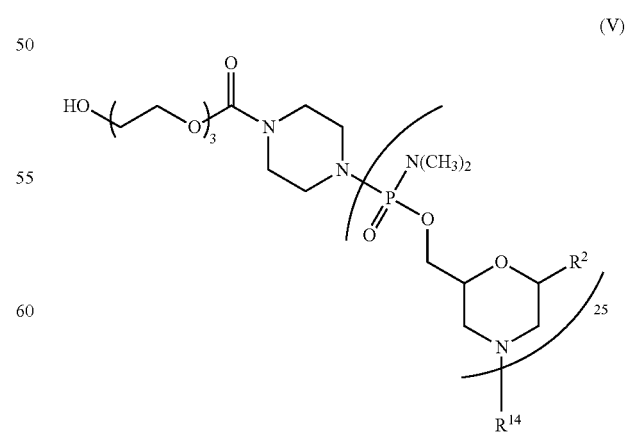

or a pharmaceutically acceptable salt thereof.

In still another aspect, provided herein is a method of treating a muscle disease, a viral infection, or a bacterial infection in a subject in need thereof, comprising administering to the subject a peptide-oligonucleotide-conjugate of the present disclosure.

DETAILED DESCRIPTION

Figure 1:
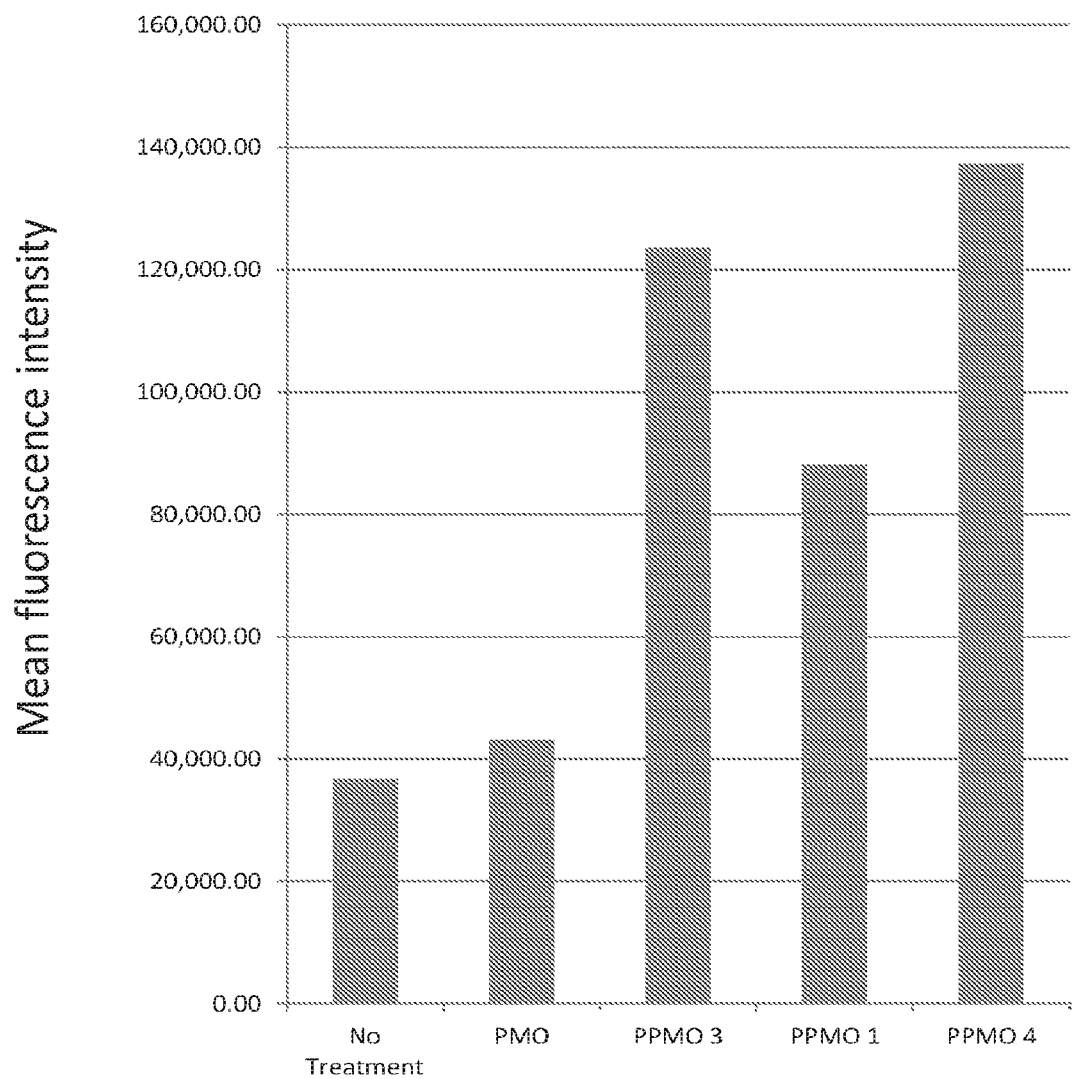
FIG. 1 shows the extent of penetration of selected oligonucleotides, peptides, and peptide-oligonucleotide-conjugates into HeLa cells based on flow cytometry experiments.
Figure 2A:
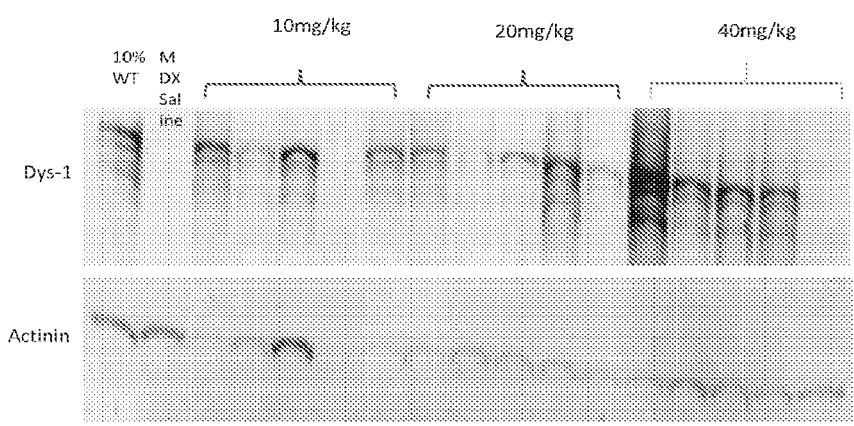
FIG. 2A is a western blot showing dystrophin levels in mouse quadriceps tissue following administration of PPMO 5.
Figure 2B:
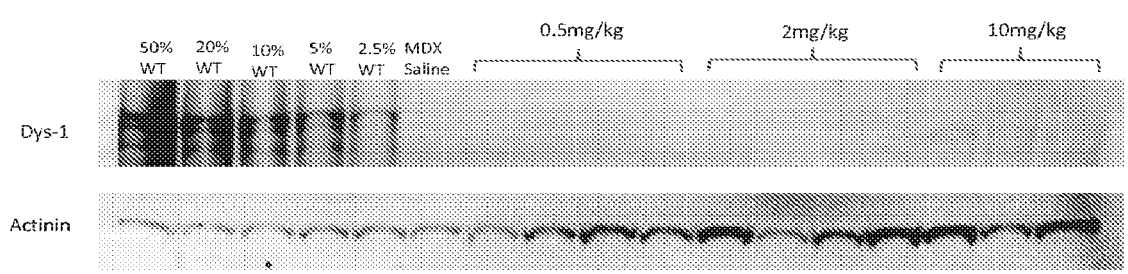
FIG. 2B is a western blot showing dystrophin levels in mouse quadriceps tissue following administration of PPMO 6.
Figure 2C:
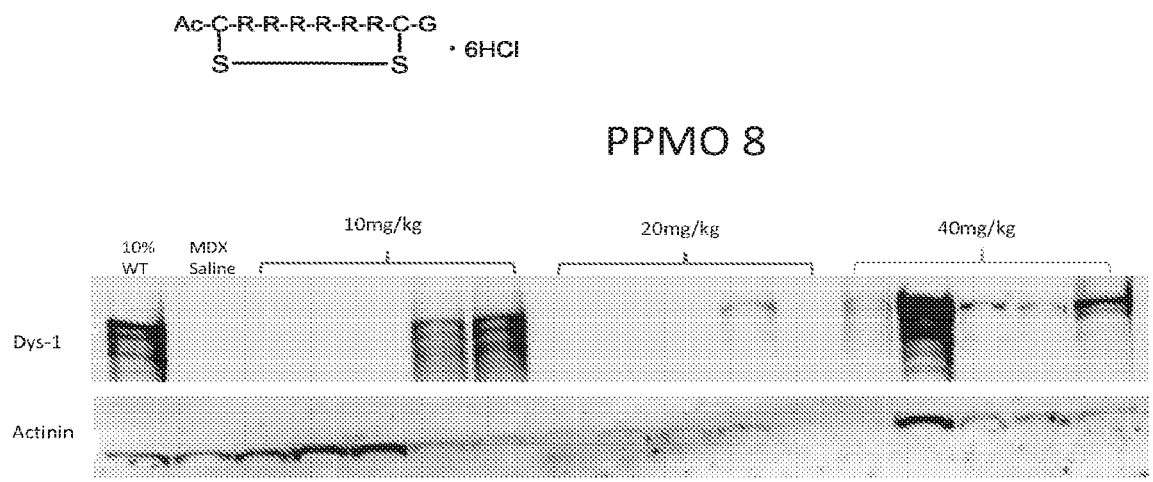
FIG. 2C is a western blot showing dystrophin levels in mouse quadriceps tissue following administration of PPMO 8.
Figure 2D:
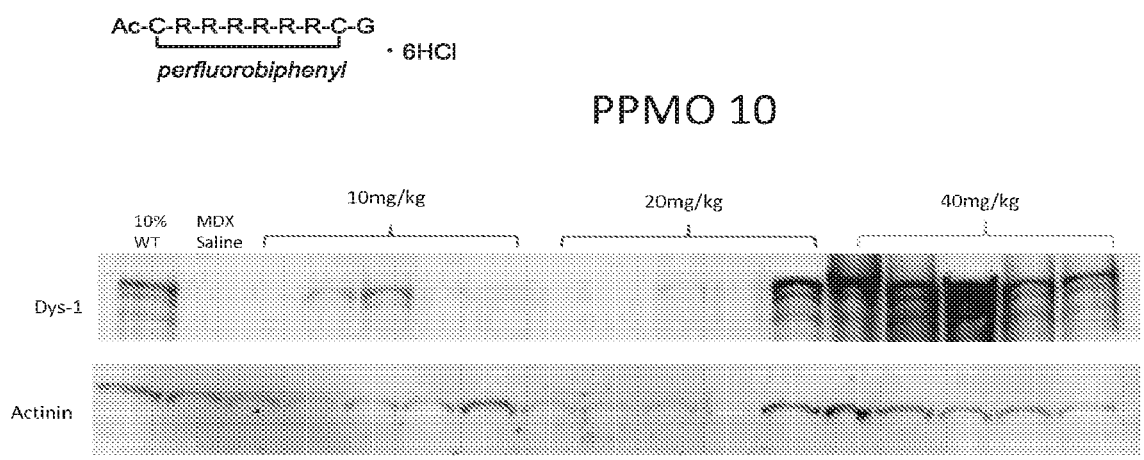
FIG. 2D is a western blot showing dystrophin levels in mouse quadriceps tissue following administration of PPMO 10.
Figure 3A:
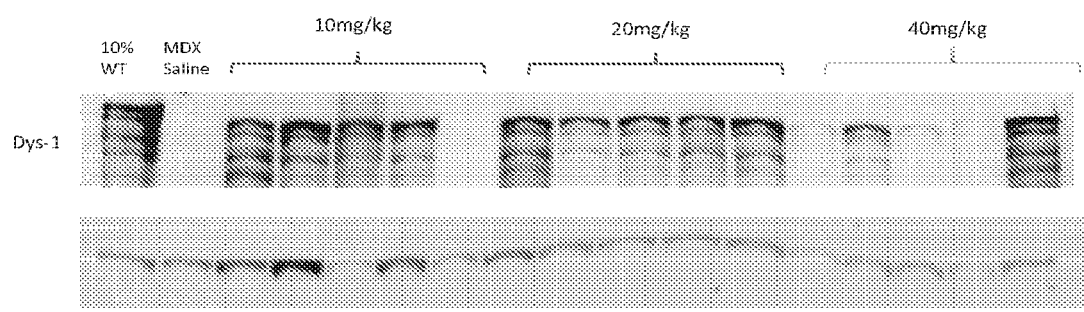
FIG. 3A is a western blot showing dystrophin levels in mouse quadriceps tissue following administration of PPMO 5.
Figure 3B:
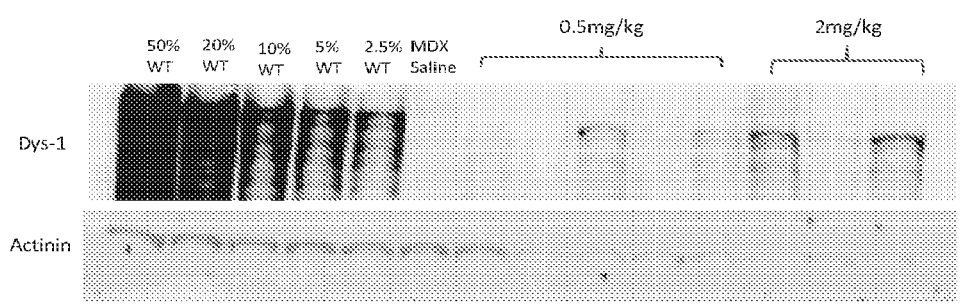
FIG. 3B is a western blot showing dystrophin levels in mouse quadriceps tissue following administration of PPMO 7.
Figure 3C:
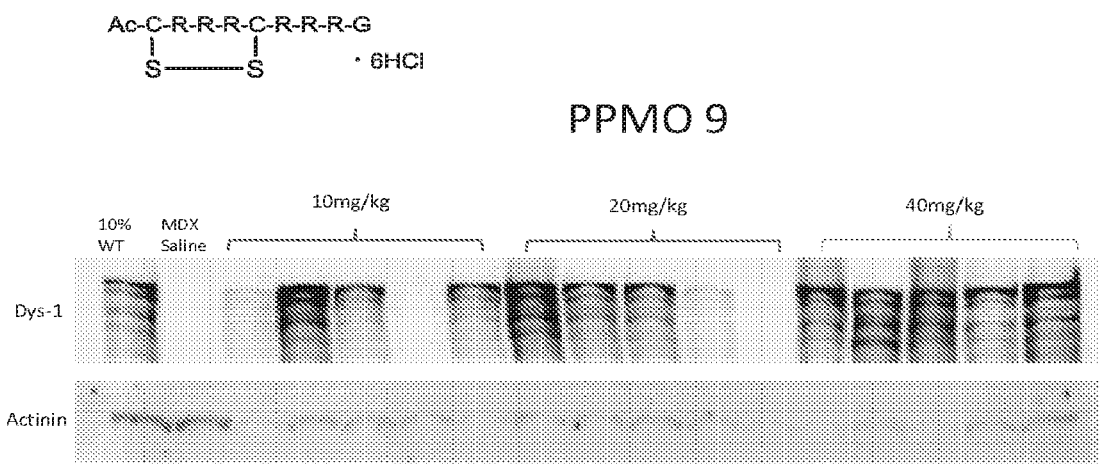
FIG. 3C is a western blot showing dystrophin levels in mouse quadriceps tissue following administration of PPMO 9.
Figure 3D:
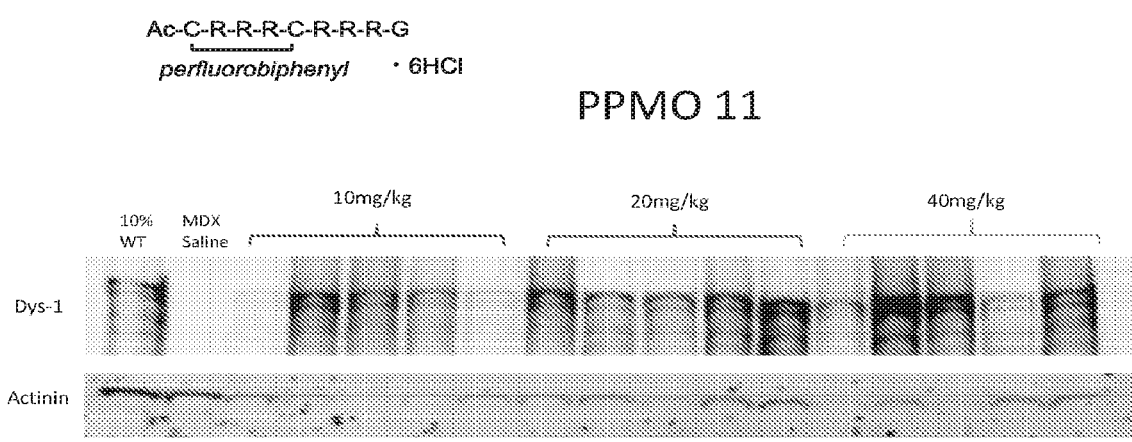
FIG. 3D is a western blot showing dystrophin levels in mouse quadriceps tissue following administration of PPMO 11.
Figure 4A:
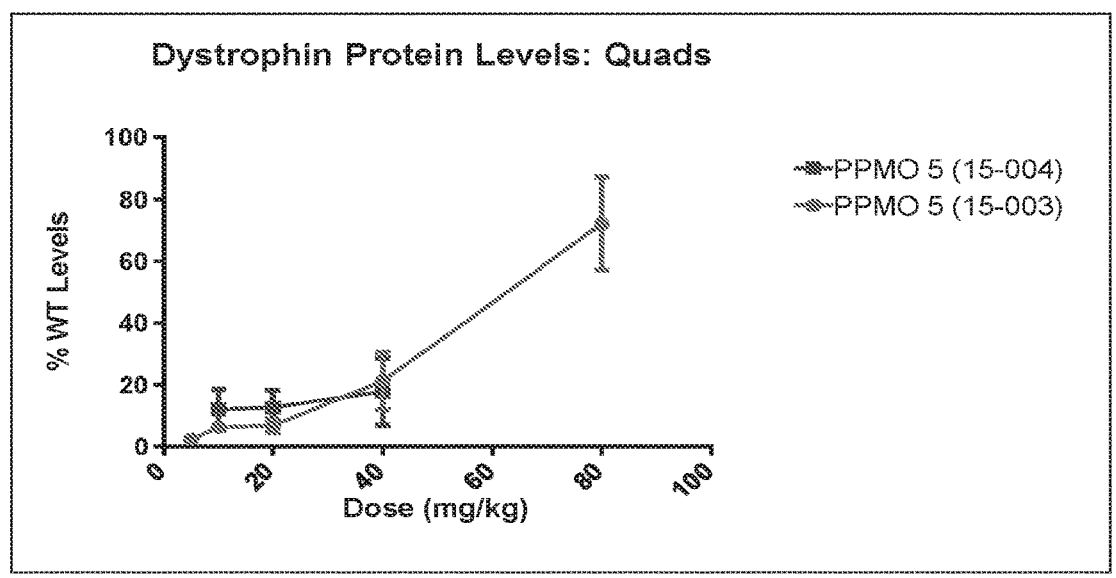
FIG. 4A shows the quantification of dystrophin levels in mouse quadriceps tissue following administration of PPMO 5 (two replications of same assay).
Figure 4B:
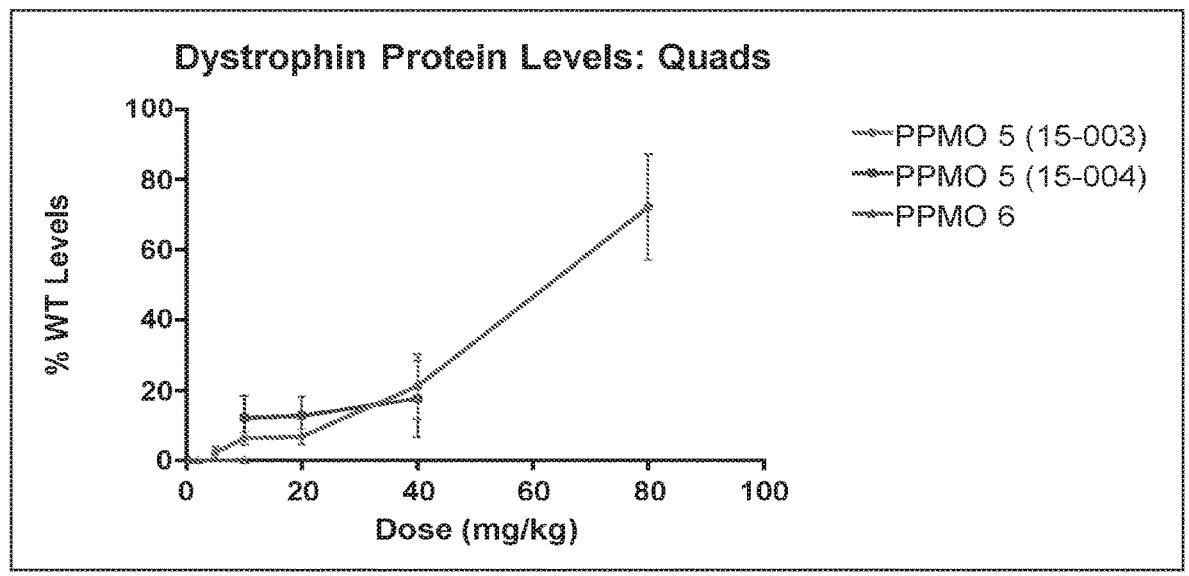
FIG. 4B shows the quantification of dystrophin levels in mouse quadriceps tissue following administration of PPMO 5 (two replications of same assay) or PPMO 6.
Figure 4C:
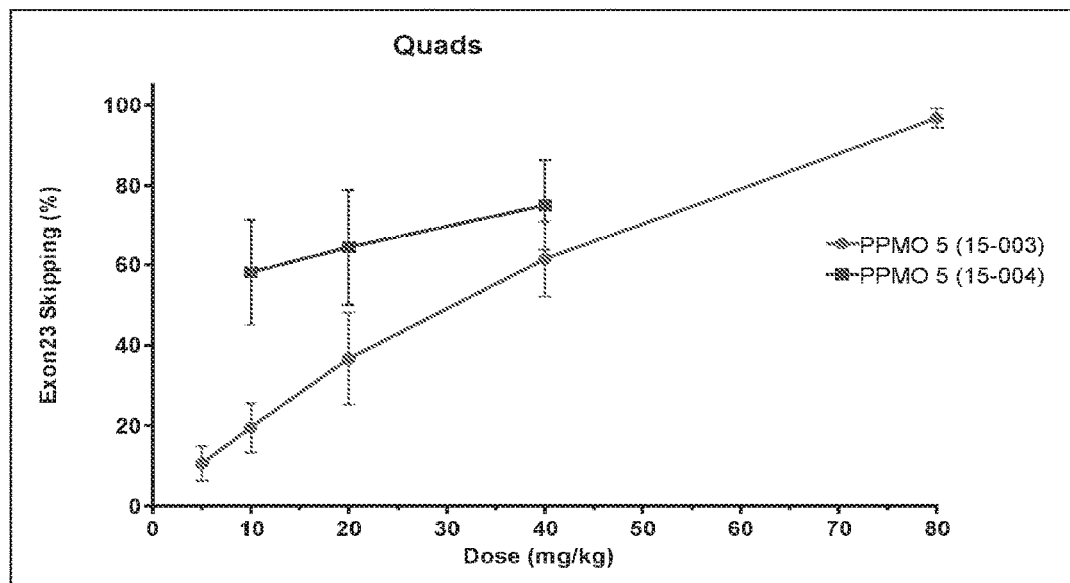
FIG. 4C shows the quantification of Exon23 Skipping (%) in mouse quadriceps tissue following administration of PPMO 5 (two replications of same assay).
Figure 4D:
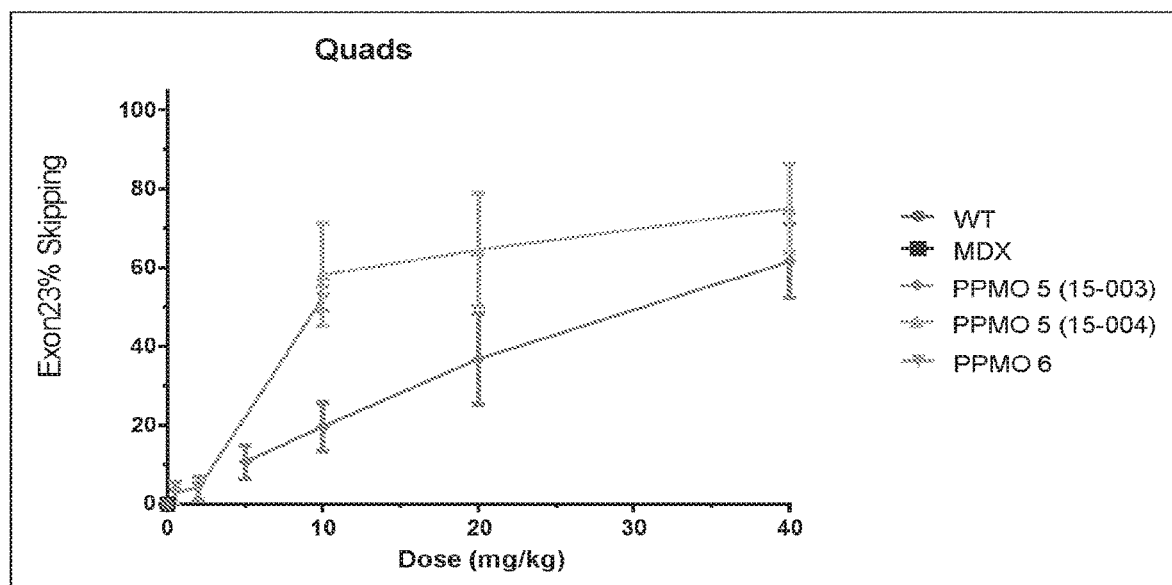
FIG. 4D shows the quantification of Exon23 Skipping (%) in mouse quadriceps tissue following administration of PPMO 5 (two replications of same assay) or PPMO 6; wildtype and mdx mice were used as controls.
Figure 5A:
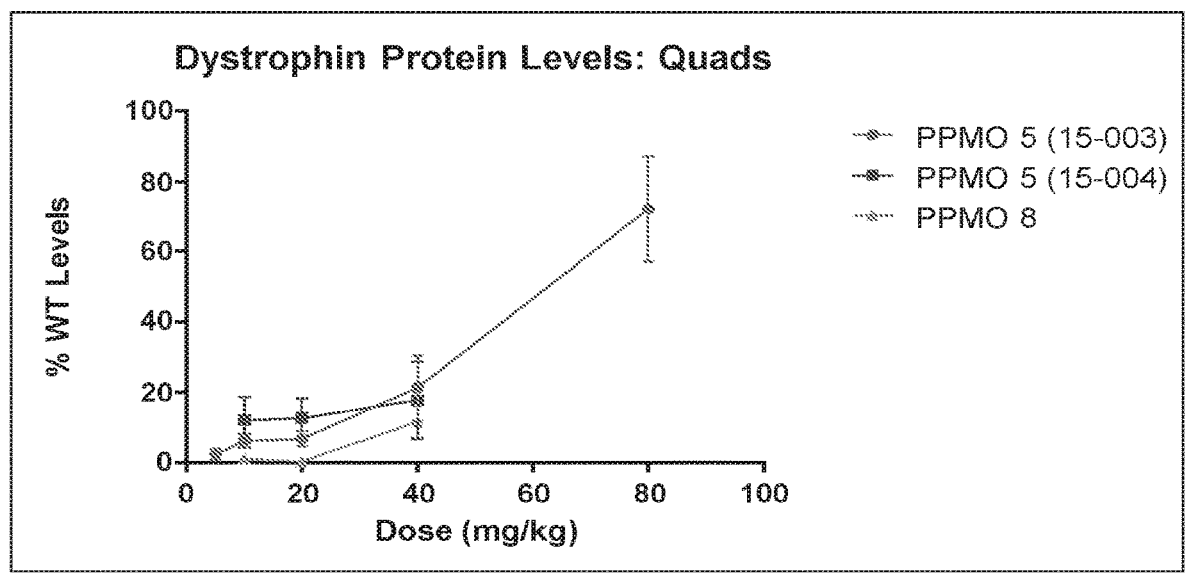
FIG. 5A shows the quantification of dystrophin levels in mouse quadriceps tissue following administration of PPMO 5 (two replications of same assay) or PPMO 8.
Figure 5B:
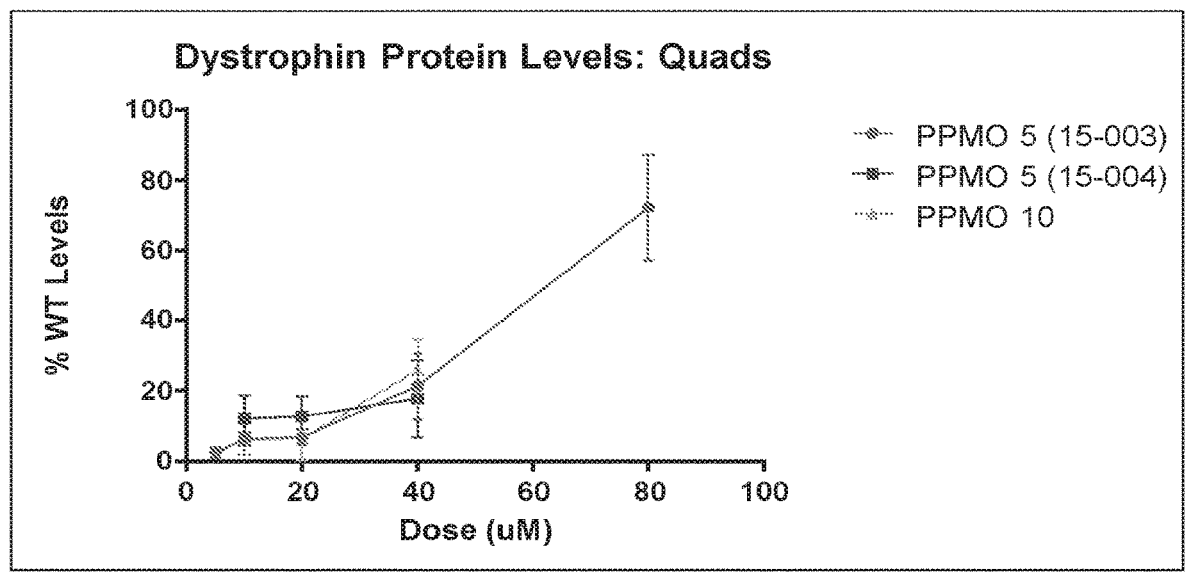
FIG. 5B shows the quantification of dystrophin levels in mouse quadriceps tissue following administration of PPMO 5 (two replications of same assay) or PPMO 10.
Figure 5C:
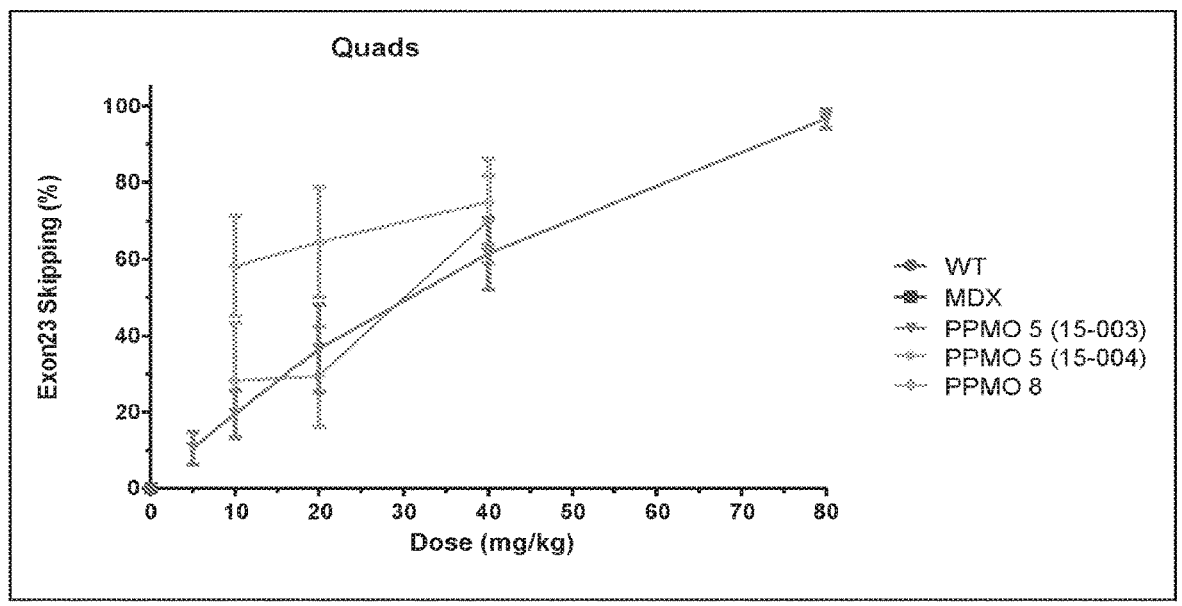
FIG. 5C shows the quantification of Exon23 Skipping (%) in mouse quadriceps tissue following administration of PPMO 5 (two replications of same assay) or PPMO 8; wildtype and mdx mice were used as controls.
Figure 5D:
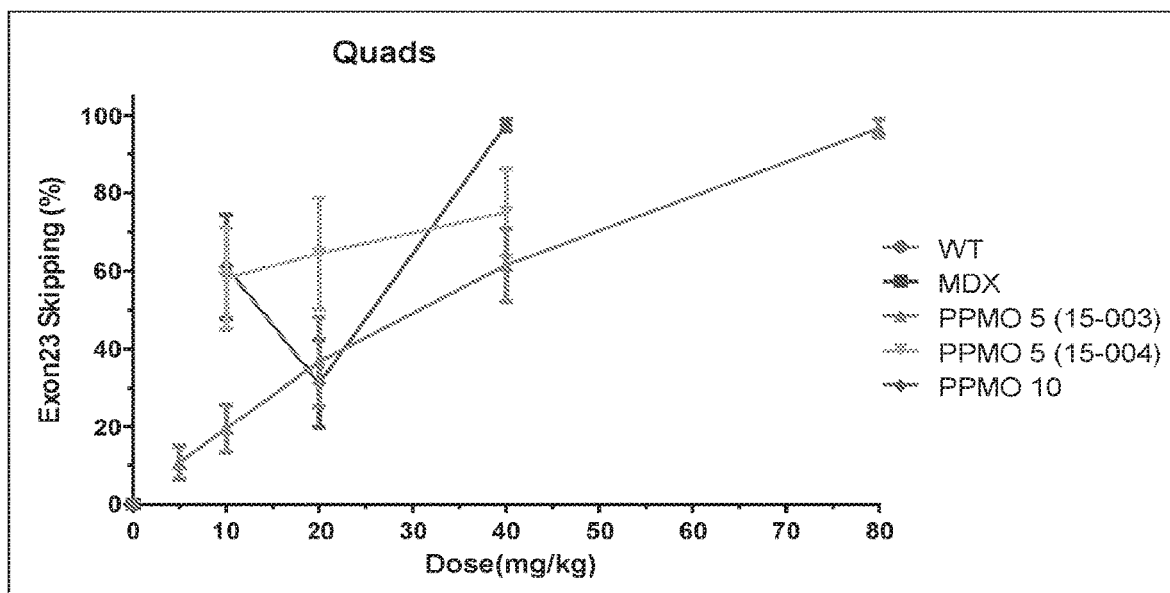
FIG. 5D shows the quantification of Exon23 Skipping (%) in mouse quadriceps tissue following administration of PPMO 5 (two replications of same assay) or PPMO 10; wildtype and mdx mice were used as controls.
Figure 6A:
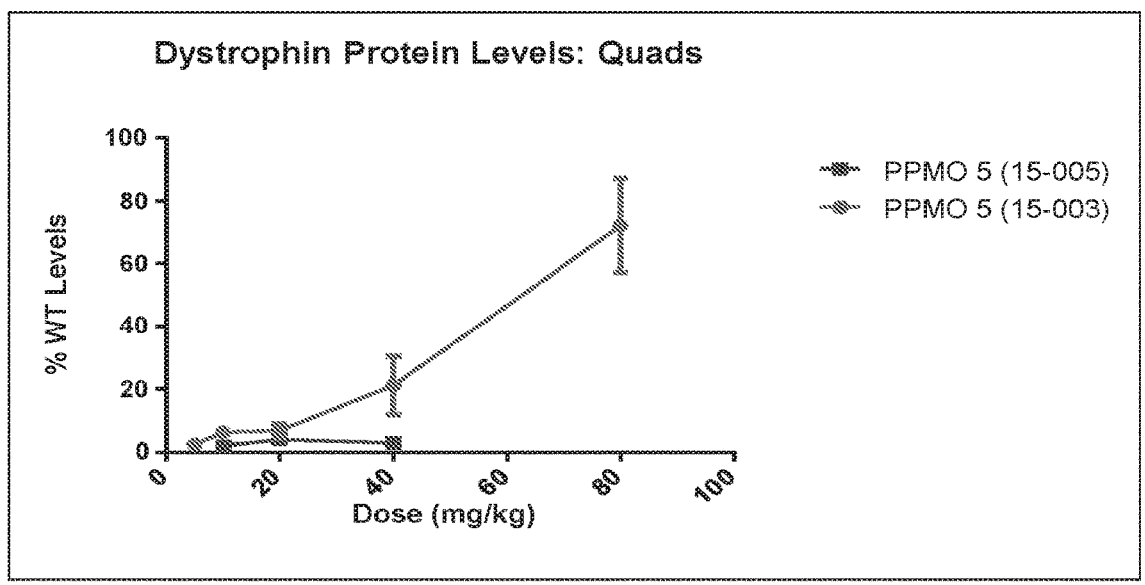
FIG. 6A shows the quantification of dystrophin levels in mouse quadriceps tissue following administration of PPMO 5 (two replications of same assay).
Figure 6B:
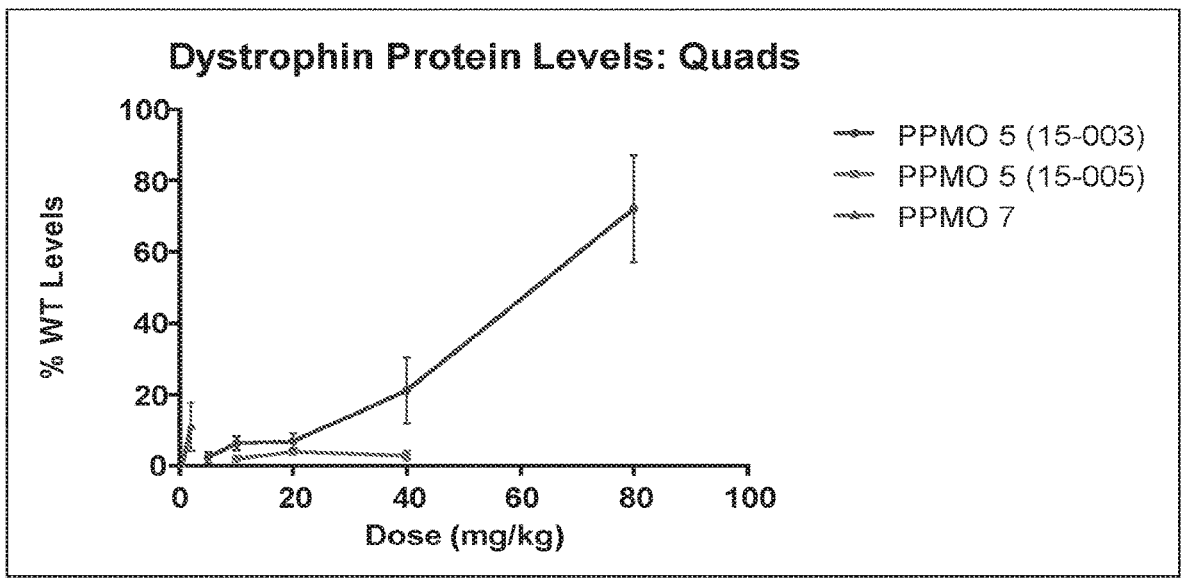
FIG. 6B shows the quantification of dystrophin levels in mouse quadriceps tissue following administration of PPMO 5 (two replications of same assay) or PPMO 7.
Figure 6C:
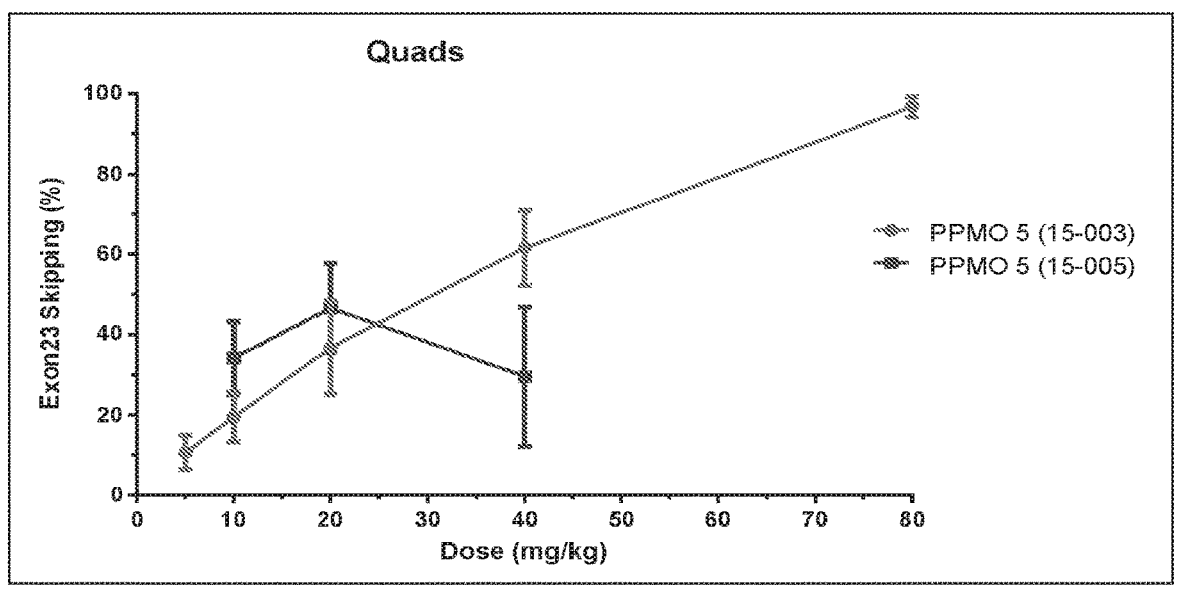
FIG. 6C shows the quantification of Exon23 Skipping (%) in mouse quadriceps tissue following administration of PPMO 5 (two replications of same assay).
Figure 6D:
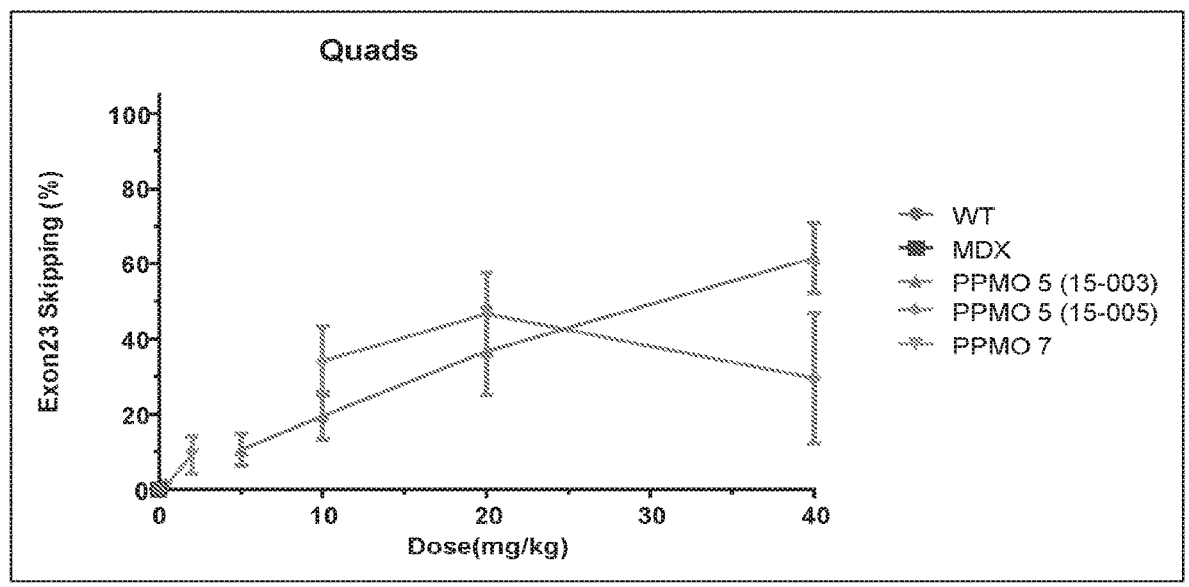
FIG. 6D shows the quantification of Exon23 Skipping (%) in mouse quadriceps tissue following administration of PPMO 5 (two replications of same assay) or PPMO 7; wildtype and mdx mice were used as controls.

Provided herein are peptides, oligonucleotides, and peptide-oligonucleotide-conjugates. Also provided herein are methods of treating a disease in a subject in need thereof, comprising administering to the subject a peptide-oligonucleotide-conjugate described herein. The oligonucleotides, and thereby the peptide-oligonucleotide-conjugates, described herein display stronger affinity for DNA and RNA without compromising sequence selectivity, relative to native or unmodified oligonucleotides. In some embodiments, the oligonucleotides of the disclosure minimize or prevent cleavage by RNase H. In some embodiments, the antisense oligonucleotides of the disclosure do not activate RNase H.

The peptides described herein impart to their corresponding peptide-oligonucleotide-conjugates lower toxicity, enhance the activity of the oligonucleotide, improve pharmacokinetics and tissue distribution, improve cellular delivery, and impart both reliable and controllable in vivo distribution.

Definitions

Listed below are definitions of various terms used to describe this disclosure. These definitions apply to the terms as they are used throughout this specification and claims, unless otherwise limited in specific instances, either individually or as part of a larger group.

The term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

The term "alkyl" refers to saturated, straight- or branched-chain hydrocarbon moieties containing, in certain embodiments, between one and six, or one and eight carbon atoms, respectively. Examples of $C_{1-6}$-alkyl moieties include, but are not limited to, methyl, ethyl, propyl, isopropyl, n-butyl, tert-butyl, neopentyl, n-hexyl moieties; and examples of $C_{1-8}$-alkyl moieties include, but are not limited to, methyl, ethyl, propyl, isopropyl, n-butyl, tert-butyl, neopentyl, n-hexyl, heptyl, and octyl moieties.

The number of carbon atoms in an alkyl substituent can be indicated by the prefix "$C_{x-y}$," where x is the minimum and y is the maximum number of carbon atoms in the substituent. Likewise, a $C_x$ chain means an alkyl chain containing x carbon atoms.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$—CH$_2$—S(=O)—CH$_3$. Up to two heteroatoms may be consecutive, such as, for example, —CH$_2$—NH—OCH$_3$, or —CH$_2$—CH$_2$—S—S—CH$_3$. The term "aryl," employed alone or in combination with other terms, means, unless otherwise stated, a carbocyclic aromatic system containing one or more rings (typically one, two, or three rings), wherein such rings may be attached together in a pendent manner, such as a biphenyl, or may be fused, such as naphthalene. Examples of aryl groups include phenyl, anthracyl, and naphthyl. In various embodiments, examples of an aryl group may include phenyl (e.g., $C_6$-aryl) and biphenyl (e.g., $C_{12}$-aryl). In some embodiments, aryl groups have from six to sixteen carbon atoms. In some embodiments, aryl groups have from six to twelve carbon atoms (e.g., $C_{6-12}$-aryl). In some embodiments, aryl groups have six carbon atoms (e.g., $C_6$-aryl).

As used herein, the term "heteroaryl" or "heteroaromatic" refers to a heterocycle having aromatic character. Heteroaryl substituents may be defined by the number of carbon atoms, e.g., $C_{1-9}$-heteroaryl indicates the number of carbon atoms contained in the heteroaryl group without including the number of heteroatoms. For example, a $C_{1-9}$-heteroaryl will include an additional one to four heteroatoms. A polycyclic heteroaryl may include one or more rings that are partially saturated. Non-limiting examples of heteroaryls include pyridyl, pyrazinyl, pyrimidinyl (including, e.g., 2- and 4-pyrimidinyl), pyridazinyl, thienyl, furyl, pyrrolyl (including, e.g., 2-pyrrolyl), imidazolyl, thiazolyl, oxazolyl, pyrazolyl (including, e.g., 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Non-limiting examples of polycyclic heterocycles and heteroaryls include indolyl (including, e.g., 3-, 4-, 5-, 6- and 7-indolyl), indolinyl, quinolyl, tetrahydroquinolyl, isoquinolyl (including, e.g., 1- and 5-isoquinolyl), 1,2,3,4-tetrahydroisoquinolyl, cinnolinyl, quinoxalinyl (including, e.g., 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (including, e.g., 3-, 4-, 5-, 6- and 7-benzofuryl), 2,3-dihydrobenzofuryl, 1,2-benzisoxazolyl, benzothienyl (including, e.g., 3-, 4-, 5-, 6-, and 7-benzothienyl), benzoxazolyl, benzothiazolyl (including, e.g., 2-benzothiazolyl and 5-benzothiazolyl), purinyl, benzimidazolyl (including, e.g., 2-benzimidazolyl), benzotriazolyl, thioxanthinyl, carbazolyl, carbolinyl, acridinyl, pyrrolizidinyl, and quinolizidinyl.

The term "protecting group" or "chemical protecting group" refers to chemical moieties that block some or all reactive moieties of a compound and prevent such moieties from participating in chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, monomethoxytrityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid moieties may be blocked with base labile groups such as, without limitation, methyl, or ethyl, and hydroxy reactive moieties may be blocked with base labile groups such as acetyl in the presence of amines blocked with acid labile groups such as tert-butyl carbamate or with carbamates that are both acid and base stable but hydrolytically removable.

Carboxylic acid and hydroxyl reactive moieties may also be blocked with hydrolytically removable protective groups such as the benzyl group, while amine groups may be blocked with base labile groups such as Fmoc. A particularly useful amine protecting group for the synthesis of compounds of Formula (I) is the trifluoroacetamide. Carboxylic acid reactive moieties may be blocked with oxidatively-removable protective groups such as 2,4-dimethoxybenzyl, while coexisting amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

The term "nucleobase," "base pairing moiety," "nucleobase-pairing moiety," or "base" refers to the heterocyclic ring portion of a nucleoside, nucleotide, and/or morpholino subunit. Nucleobases may be naturally occurring, or may be modified or analogs of these naturally occurring nucleobases, e.g., one or more nitrogen atoms of the nucleobase may be independently at each occurrence replaced by carbon. Exemplary analogs include hypoxanthine (the base component of the nucleoside inosine); 2, 6-diaminopurine; 5-methyl cytosine; C5-propynyl-modified pyrimidines; 10-(9-(aminoethoxy)phenoxazinyl) (G-clamp) and the like.

Further examples of base pairing moieties include, but are not limited to, uracil, thymine, adenine, cytosine, guanine and hypoxanthine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). The modified nucleobases disclosed in Chiu and Rana, R N A, 2003, 9, 1034-1048, Limbach et al. Nucleic Acids Research, 1994, 22, 2183-2196 and Revankar and Rao, Comprehensive Natural Products Chemistry, vol. 7, 313, are also contemplated, the contents of which are incorporated herein by reference.

Further examples of base pairing moieties include, but are not limited to, expanded-size nucleobases in which one or more benzene rings has been added. Nucleic base replacements described in the Glen Research catalog (www.glen-research.com); Krueger AT et al., Acc. Chem. Res., 2007, 40, 141-150; Kool, ET, Acc. Chem. Res., 2002, 35, 936-943; Benner S. A., et al., Nat. Rev. Genet., 2005, 6, 553-543; Romesberg, F. E., et al., Curr. Opin. Chem. Biol., 2003, 7, 723-733; Hirao, I., Curr. Opin. Chem. Biol., 2006, 10, 622-627, the contents of which are incorporated herein by reference, are contemplated as useful for the synthesis of the oligomers described herein. Examples of expanded-size nucleobases are shown below:

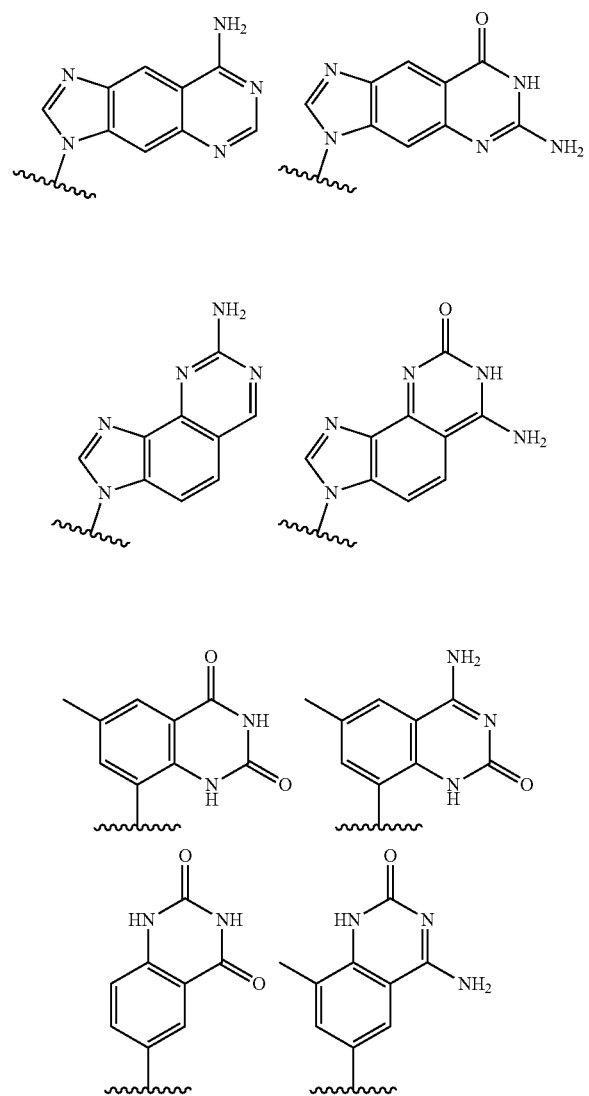
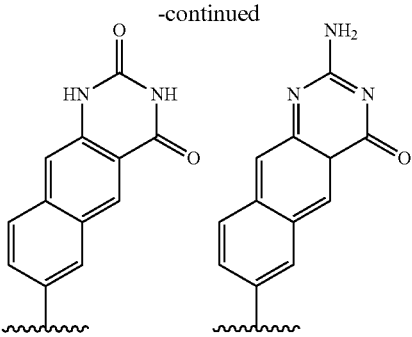

The terms "oligonucleotide" or "oligomer" refer to a compound comprising a plurality of linked nucleosides, nucleotides, or a combination of both nucleosides and nucleotides. In specific embodiments provided herein, an oligonucleotide is a morpholino oligonucleotide.

The phrase "morpholino oligonucleotide" or "PMO" refers to a modified oligonucleotide having morpholino subunits linked together by phosphoramidate or phosphorodiamidate linkages, joining the morpholino nitrogen of one subunit to the 5'-exocyclic carbon of an adjacent subunit. Each morpholino subunit comprises a nucleobase-pairing moiety effective to bind, by nucleobase-specific hydrogen bonding, to a nucleobase in a target.

The terms "antisense oligomer," "antisense compound" and "antisense oligonucleotide" are used interchangeably and refer to a sequence of subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid: oligomer heteroduplex within the target sequence. The oligomer may have exact (perfect) or near (sufficient) sequence complementarity to the target sequence; variations in sequence near the termini of an oligomer are generally preferable to variations in the interior.

Such an antisense oligomer can be designed to block or inhibit translation of mRNA or to inhibit/alter natural or abnormal pre-mRNA splice processing, and may be said to be "directed to" or "targeted against" a target sequence with which it hybridizes. The target sequence is typically a region including an AUG start codon of an mRNA, a Translation Suppressing Oligomer, or splice site of a pre-processed mRNA, a Splice Suppressing Oligomer (SSO). The target sequence for a splice site may include an mRNA sequence having its 5' end 1 to about 25 base pairs downstream of a normal splice acceptor junction in a preprocessed mRNA. In various embodiments, a target sequence may be any region of a preprocessed mRNA that includes a splice site or is contained entirely within an exon coding sequence or spans a splice acceptor or donor site. An oligomer is more generally said to be "targeted against" a biologically relevant target, such as a protein, virus, or bacteria, when it is targeted against the nucleic acid of the target in the manner described above.

The antisense oligonucleotide and the target RNA are complementary to each other when a sufficient number of corresponding positions in each molecule are occupied by nucleotides which can hydrogen bond with each other, such that stable and specific binding occurs between the oligonucleotide and the target. Thus, "specifically hybridizable" and "complementary" are terms which are used to indicate a sufficient degree of complementarity or precise pairing such that stable and specific binding occurs between the oligonucleotide and the target. It is understood in the art that the sequence of an oligonucleotide need not be 100% complementary to that of its target sequence to be specifically hybridizable. An oligonucleotide is specifically hybridizable when binding of the oligonucleotide to the target molecule interferes with the normal function of the target RNA, and there is a sufficient degree of complementarity to avoid non-specific binding of the antisense oligonucleotide to non-target sequences under conditions in which specific binding is desired, i.e., under physiological conditions in the case of in vivo assays or therapeutic treatment, and in the case of in vitro assays, under conditions in which the assays are performed.

Oligonucleotides may also include nucleobase (often referred to in the art simply as "base") modifications or substitutions. Oligonucleotides containing a modified or substituted base include oligonucleotides in which one or more purine or pyrimidine bases most commonly found in nucleic acids are replaced with less common or non-natural bases. In some embodiments, the nucleobase is covalently linked at the N9 atom of the purine base, or at the N1 atom of the pyrimidine base, to the morpholine ring of a nucleotide or nucleoside.

Purine bases comprise a pyrimidine ring fused to an imidazole ring, as described by the general formula:

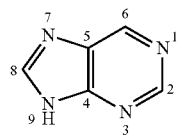

Purine

Adenine and guanine are the two purine nucleobases most commonly found in nucleic acids. These may be substituted with other naturally-occurring purines, including but not limited to N6-methyladenine, N2-methylguanine, hypoxanthine, and 7-methylguanine.

Pyrimidine bases comprise a six-membered pyrimidine ring as described by the general formula:

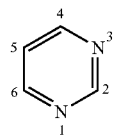

Pyrimidine

Cytosine, uracil, and thymine are the pyrimidine bases most commonly found in nucleic acids. These may be substituted with other naturally-occurring pyrimidines, including but not limited to 5-methylcytosine, 5-hydroxymethylcytosine, pseudouracil, and 4-thiouracil. In one embodiment, the oligonucleotides described herein contain thymine bases in place of uracil.

Other modified or substituted bases include, but are not limited to, 2,6-diaminopurine, orotic acid, agmatidine, lysidine, 2-thiopyrimidine (e.g. 2-thiouracil, 2-thiothymine), G-clamp and its derivatives, 5-substituted pyrimidine (e.g. 5-halouracil, 5-propynyluracil, 5-propynylcytosine, 5-aminomethyluracil, 5-hydroxymethyluracil, 5-aminomethylcytosine, 5-hydroxymethylcytosine, Super T), 7-deazaguanine, 7-deazaadenine, 7-aza-2,6-diaminopurine, 8-aza-7-deazaguanine, 8-aza-7-deazaadenine, 8-aza-7-deaza-2,6-diaminopurine, Super G, Super A, and N4-ethylcytosine, or derivatives thereof; N2-cyclopentylguanine (cPent-G), N2-cyclopentyl-2-aminopurine (cPent-AP), and N2-propyl-2-aminopurine (Pr-AP), pseudouracil or derivatives thereof and degenerate or universal bases, like 2,6-difluorotoluene or absent bases like abasic sites (e.g. 1-deoxyribose, 1,2-dideoxyribose, 1-deoxy-2-O-methylribose; or pyrrolidine derivatives in which the ring oxygen has been replaced with nitrogen (azaribose)). Pseudouracil is a naturally occuring isomerized version of uracil, with a C-glycoside rather than the regular N-glycoside as in uridine.

Certain modified or substituted nucleobases are particularly useful for increasing the binding affinity of the antisense oligonucleotides of the disclosure. These include 5-substituted pyrimidines, 6-azapyrimidines and N-2, N-6 and 0-6 substituted purines, including 2-aminopropyladenine, 5-propynyluracil and 5-propynylcytosine. In various embodiments, nucleobases may include 5-methylcytosine substitutions, which have been shown to increase nucleic acid duplex stability by 0.6-1.2° C.

In some embodiments, modified or substituted nucleobases are useful for facilitating purification of antisense oligonucleotides. For example, in certain embodiments, antisense oligonucleotides may contain three or more (e.g. 3, 4, 5, 6 or more) consecutive guanine bases. In certain antisense oligonucleotides, a string of three or more consecutive guanine bases can result in aggregation of the oligonucleotides, complicating purification. In such antisense oligonucleotides, one or more of the consecutive guanines can be substituted with hypoxanthine. The substitution of hypoxanthine for one or more guanines in a string of three or more consecutive guanine bases can reduce aggregation of the antisense oligonucleotide, thereby facilitating purification.

The oligonucleotides provided herein are synthesised and do not include antisense compositions of biological origin. The molecules of the disclosure may also be mixed, encapsulated, conjugated or otherwise associated with other molecules, molecule structures or mixtures of compounds, as for example, liposomes, receptor targeted molecules, oral, rectal, topical or other formulations, for assisting in uptake, distribution, or absorption, or a combination thereof.

The terms "complementary" and "complementarity" refer to oligonucleotides (i.e., a sequence of nucleotides) related by base-pairing rules. For example, the sequence "T-G-A (5'-3')," is complementary to the sequence "T-C-A (5'-3')." Complementarity may be "partial," in which only some of the nucleic acids' bases are matched according to base pairing rules. Or, there may be "complete," "total," or "perfect" (100%) complementarity between the nucleic acids. The degree of complementarity between nucleic acid strands has significant effects on the efficiency and strength of hybridization between nucleic acid strands. While perfect complementarity is often desired, some embodiments can include one or more but preferably 6, 5, 4, 3, 2, or 1 mismatches with respect to the target RNA. Such hybridization may occur with "near" or "substantial" complementarity of the antisense oligomer to the target sequence, as well as with exact complementarity. In some embodiments, an oligomer may hybridize to a target sequence at about 50%, 55%, 60%, 65%, 70%, 75%, 80%, 85%, 90%, 95%, 99% or 100% complementarity. Variations at any location within the oligomer are included. In certain embodiments, variations in sequence near the termini of an oligomer are generally preferable to variations in the interior, and if present are typically within about 6, 5, 4, 3, 2, or 1 nucleotides of the 5'-terminus, 3'-terminus, or both termini.

The term "peptide" refers to a compound comprising a plurality of linked amino acids. The peptides provided herein can be considered to be cell penetrating peptides.

The terms "cell penetrating peptide" and "CPP" are used interchangeably and refer to cationic cell penetrating peptides, also called transport peptides, carrier peptides, or peptide transduction domains. The peptides, provided herein, have the capability of inducing cell penetration within 100% of cells of a given cell culture population and allow macromolecular translocation within multiple tissues in vivo upon systemic administration. In various embodiments, a CPP embodiment of the disclosure may include an arginine-rich peptide as described further below.

The term "treatment" refers to the application of one or more specific procedures used for the amelioration of a disease. In certain embodiments, the specific procedure is the administration of one or more pharmaceutical agents. "Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent. Treatment includes any desirable effect on the symptoms or pathology of a disease or condition, and may include, for example, minimal changes or improvements in one or more measurable markers of the disease or condition being treated. Also included are "prophylactic" treatments, which can be directed to reducing the rate of progression of the disease or condition being treated, delaying the onset of that disease or condition, or reducing the severity of its onset. An "effective amount" or "therapeutically effective amount" refers to an amount of therapeutic compound, such as an antisense oligomer, administered to a mammalian subject, either as a single dose or as part of a series of doses, which is effective to produce a desired therapeutic effect.

The term "amelioration" means a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

As used herein, "pharmaceutically acceptable salts" refers to derivatives of the disclosed oligonucleotides wherein the parent oligonucleotide is modified by converting an existing acid or base moiety to its salt form. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Peptide-Oligonucleotide-Conjugates

Provided herein are oligonucleotides chemically-linked to one or more moieties, such as a cell penetrating peptide, that enhance the activity, cellular distribution, or cellular uptake of the oligonucleotide. The oligonucleotides can additionally be chemically-linked to one or more heteroalkyl moieties (e.g., polyethylene glycol) that further enhance the activity, cellular distribution, or cellular uptake of the oligonucleotide. In one exemplary embodiment, the arginine-rich polypeptide is covalently coupled at its N-terminal or C-terminal residue to either end, or both ends, of the antisense compound.

Thus, in one aspect, provided herein is a peptide-oligonucleotide-conjugate of Formula I:

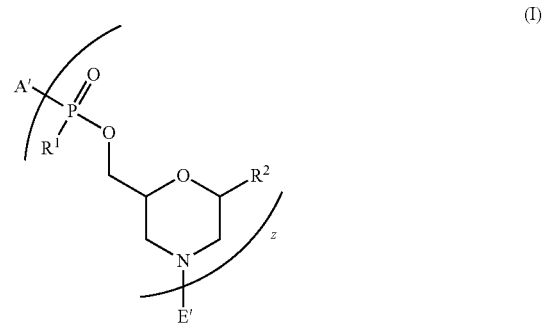

(I)

or a pharmaceutically acceptable salt thereof,
wherein:
A' is selected from —NHCH$_2$C(O)NH$_2$, —N(C$_{1-6}$-alkyl)CH$_2$C(O)NH$_2$,

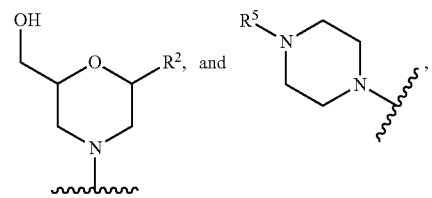

wherein
R$^5$ is —C(O)(O-alkyl)$_x$-OH, wherein x is 3-10 and each alkyl group is independently at each occurrence C$_{2-6}$-alkyl, or R$^5$ is selected from —C(O)C$_{1-6}$ alkyl, trityl, monomethoxytrityl, —(C$_{1-6}$-alkyl)R$^6$, —(C$_{1-6}$ heteroalkyl)-R$^6$, aryl-R$^6$, heteroaryl-R$^6$, —C(O)O—(C$_{1-6}$ alkyl)-R$^6$, —C(O)O-aryl-R$^6$, —C(O)O— heteroaryl-R$^6$ and

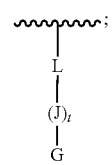

wherein R$^6$ is selected from OH, SH, and NH$_2$, or R$^6$ is O, S, or NH, covalently linked to a solid support;

each R$^1$ is independently selected from OH and —NR$^3$R$^4$, wherein each R$^3$ and R$^4$ are independently at each occurrence —C$_{1-6}$ alkyl;

each R$^2$ is independently selected from H, a nucleobase, and a nucleobase functionalized with a chemical protecting-group, wherein the nucleobase independently at each occurrence comprises a C$_{3-6}$ heterocyclic ring selected from pyridine, pyrimidine, triazinane, purine, and deaza-purine;

z is 8-40; and

E' is selected from H, —C$_{1-6}$ alkyl, —C(O)C$_{1-6}$ alkyl, benzoyl, stearoyl, trityl, monomethoxytrityl, dimethoxytrityl, trimethoxytrityl,

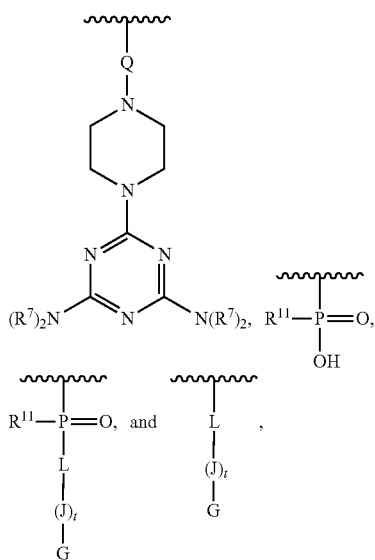

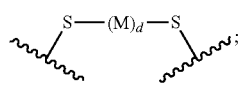

wherein
Q is —C(O)(CH$_2$)$_6$C(O)— or —C(O)(CH$_2$)$_2$S$_2$(CH$_2$)$_2$C(O)—,
R$^7$ is —(CH$_2$)$_2$OC(O)N(R$^8$)$_2$, wherein R$^8$ is —(CH$_2$)$_6$NHC(=NH)NH$_2$, and
R$^{11}$ is selected from OH and —NR$^3$R$^4$, wherein L is covalently linked by an amide bond to the carboxy-terminus of J, and L is selected from —NH(CH$_2$)$_{1-6}$C(O)—, —NH(CH$_2$)$_{1-6}$C(O)NH(CH$_2$)$_{1-6}$C(O)—, and

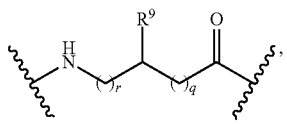

t is 4-9;
each J is independently at each occurrence selected from an amino acid of the structure
wherein:
r and q are each independently 0, 1, 2, 3, or 4; and
each R$^9$ is independently at each occurrence selected from H, an amino acid side-chain, and an amino acid side-chain functionalized with a chemical protecting-group, wherein two or more amino acid side-chain groups of R$^9$ independently at each occurrence comprise a sulfur, wherein two of the sulfur atoms, together with the atoms to which they are attached, form the structure

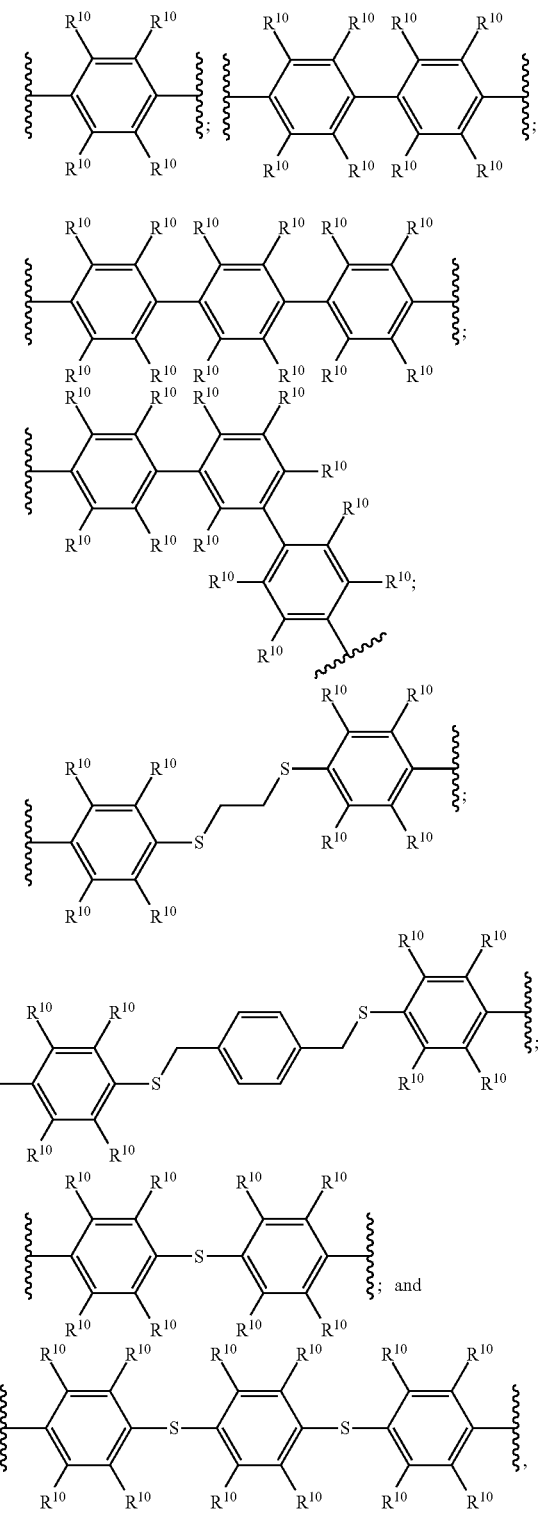

wherein d is 0 or 1, and M is selected from:

wherein each $R^{10}$ is independently at each occurrence H or a halogen; and

G is covalently linked to the amino-terminus of J, and G is selected from

H, —C(O)C$_{1-6}$ alkyl, benzoyl, and stearoyl, and wherein at least one of the following conditions is true:

1) A' is

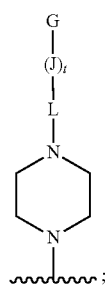

2) E' is

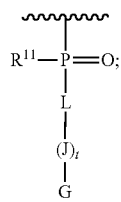

or 3) E' is

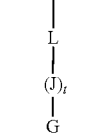

In one embodiment, E' is selected from H, —C$_{1-6}$ alkyl, —C(O)C$_{1-6}$ alkyl, benzoyl, stearoyl, trityl, monomethoxytrityl, dimethoxytrityl, trimethoxytrityl, and

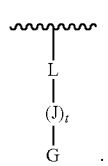

In another embodiment, only one of A' is

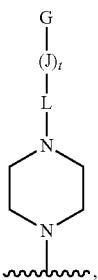

E' is

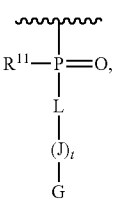

or E' is

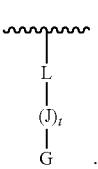

In still another embodiment, A' is

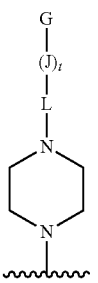

or E' is

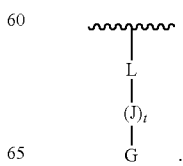

In yet another embodiment, A' is selected from —N(C$_{1-6}$-alkyl)CH$_2$C(O)NH$_2$,

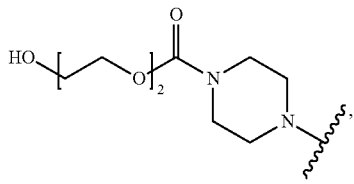

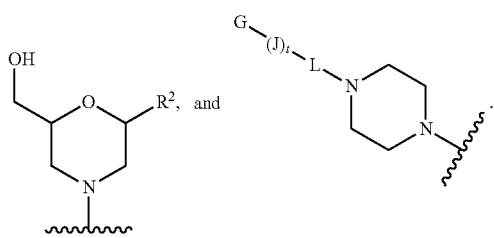

In another embodiment E' is selected from H, —C(O)CH$_3$, trityl, 4-methoxytrityl, benzoyl, stearoyl, and

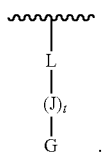

In still another embodiment, A' is selected from —N(C$_{1-6}$-alkyl)CH$_2$C(O)NH$_2$,

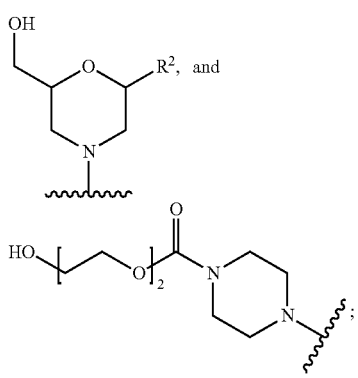

and
E' is

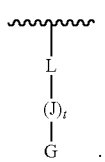

In yet another embodiment, A' is

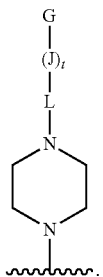

In another embodiment, E' is selected from H, —C(O)CH$_3$, trityl, 4-methoxytrityl, benzoyl, and stearoyl.

In yet another embodiment, E' is selected from H and —C(O)CH$_3$.

In still another embodiment, the peptide-oligonucleotide-conjugate of Formula I is a peptide-oligonucleotide-conjugate of Formula Ia:

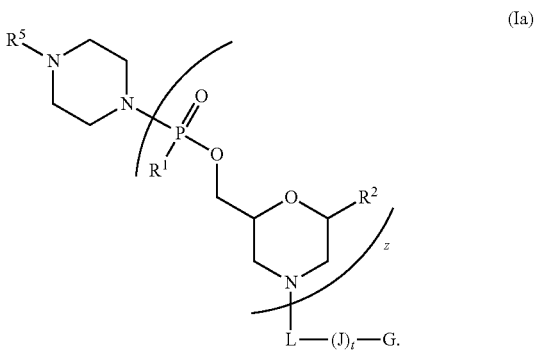

(Ia)

In an embodiment of Formula I and Ia, R$^5$ is —C(O)(O-alkyl)$_x$OH, wherein each alkyl group is independently for each occurrence C$_{2-6}$-alkyl.

In another embodiment of Formula I and Ia, R$^5$ is —C(O)(O—CH$_2$CH$_2$)$_3$OH.

In another embodiment, the peptide-oligonucleotide-conjugate of Formula I is a peptide-oligonucleotide-conjugate of Formula Ib:

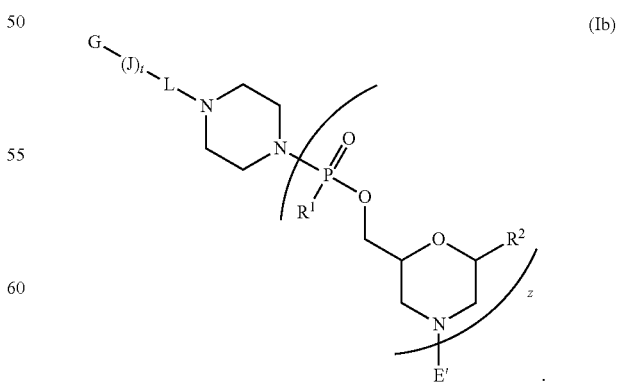

(Ib)

In an embodiment of Formula I and Ib, E' is selected from H, C$_{1-6}$ alkyl, —C(O)CH$_3$, benzoyl, and stearoyl.

In another embodiment of Formula I and Ib, E' is selected from H and —C(O)CH$_3$.

In an embodiment of Formula I, Ia, and Ib, each R$^{10}$ is independently a halogen selected from fluorine, chlorine, bromine, and iodine.

In another embodiment of Formula I, Ia, and Ib, each R$^{10}$ is fluorine.

In still another embodiment of Formula I, Ia, and Ib, M is

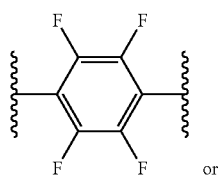

or

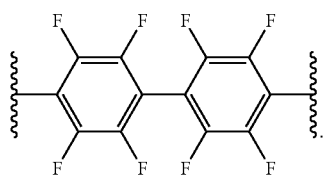

In another embodiment of Formula I, Ia, and Ib, two amino acid side-chain groups are independently at each occurrence cysteine or homocysteine amino acid side-chain groups.

In still another embodiment of Formula I, Ia, and Ib, each J is independently at each occurrence selected from an α-amino acid, a β$^2$-amino acid, and a β$^3$-amino acid.

In yet another embodiment of Formula I, Ia, and Ib, r and q are each 0.

In another embodiment of Formula I, Ia, and Ib, J is independently selected from cysteine and arginine.

In still another embodiment of Formula I, Ia, and Ib, two J groups are cysteine.

In yet another embodiment of Formula I, Ia, and Ib, z is 8-25.

In another embodiment of Formula I, Ia, and Ib, z is 15-25.

In still another embodiment of Formula I, Ia, and Ib, z is 10-20.

In another embodiment of Formula I, Ia, and Ib, each R$^1$ is independently NR$^3$R4, wherein each R$^3$ and R$^4$ are independently at each occurrence C$_{1-3}$-alkyl.

In still another embodiment of Formula I, Ia, and Ib, each R$^1$ is N(CH$_3$)$_2$.

In yet another embodiment of Formula I, Ia, and Ib, each R$^2$ is a nucleobase, wherein the nucleobase independently at each occurrence comprises a C$_{4-6}$-heterocyclic ring selected from pyridine, pyrimidine, triazinane, purine, and deaza-purine.

In another embodiment of Formula I, Ia, and Ib, each R$^2$ is a nucleobase, wherein the nucleobase independently at each occurrence comprises a C$_{4-6}$-heterocyclic ring selected from pyrimidine, purine, and deaza-purine.

In still another embodiment of Formula I, Ia, and Ib, each R$^2$ is a nucleobase independently at each occurrence selected from adenine, 2,6-diaminopurine, 7-deaza-adenine, guanine, 7-deaza-guanine, hypoxanthine, cytosine, 5-methyl-cytosine, thymine, uracil, and hypoxanthine.

In yet another embodiment of Formula I, Ia, and Ib, each R$^2$ is a nucleobase independently at each occurrence selected from adenine, guanine, cytosine, 5-methyl-cytosine, thymine, uracil, and hypoxanthine.

In another embodiment of Formula I, Ia, and Ib, L is selected from —NH(CH$_2$)$_{1-6}$C(O)—, —NH(CH$_2$)$_5$C(O)NH(CH$_2$)$_2$C(O)—, and

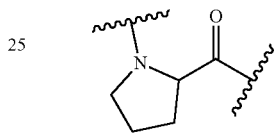

In still another embodiment of Formula I, Ia, and Ib, L is selected from glycine and

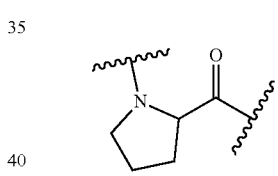

In yet another embodiment of Formula I, Ia, and Ib, L is glycine.

In another embodiment of Formula I, Ia, and Ib, G is selected from H, C(O)CH$_3$, benzoyl, and stearoyl.

In still another embodiment of Formula I, Ia, and Ib, G is H or —C(O)CH$_3$.

In yet another embodiment of Formula I, Ia, and Ib, G is —C(O)CH$_3$.

In another embodiment of Formula I, Ia, and Ib, d is 1.

In still another embodiment of Formula I, Ia, and Ib, d is 0.

In yet another embodiment of Formula I, Ia, and Ib,

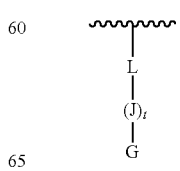

is selected from:
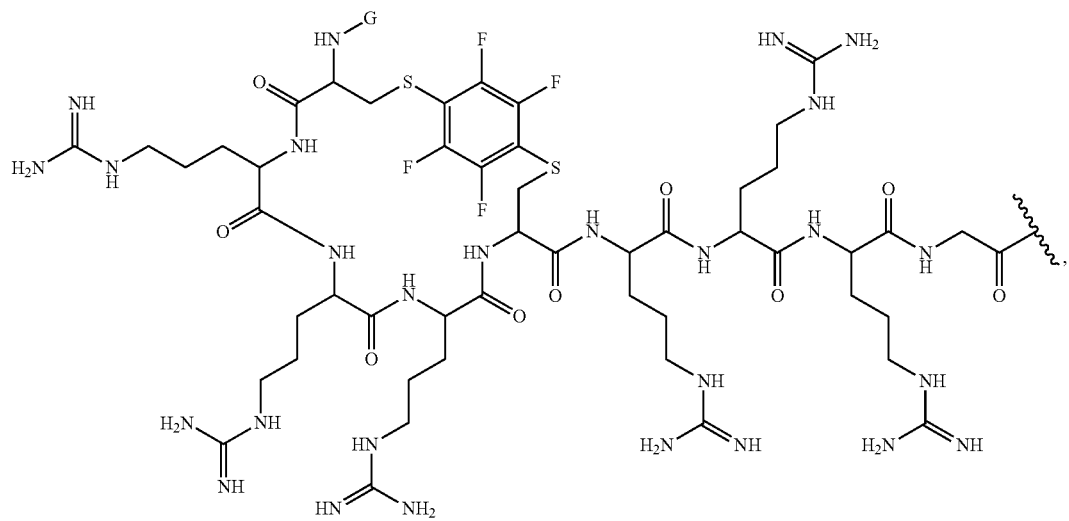
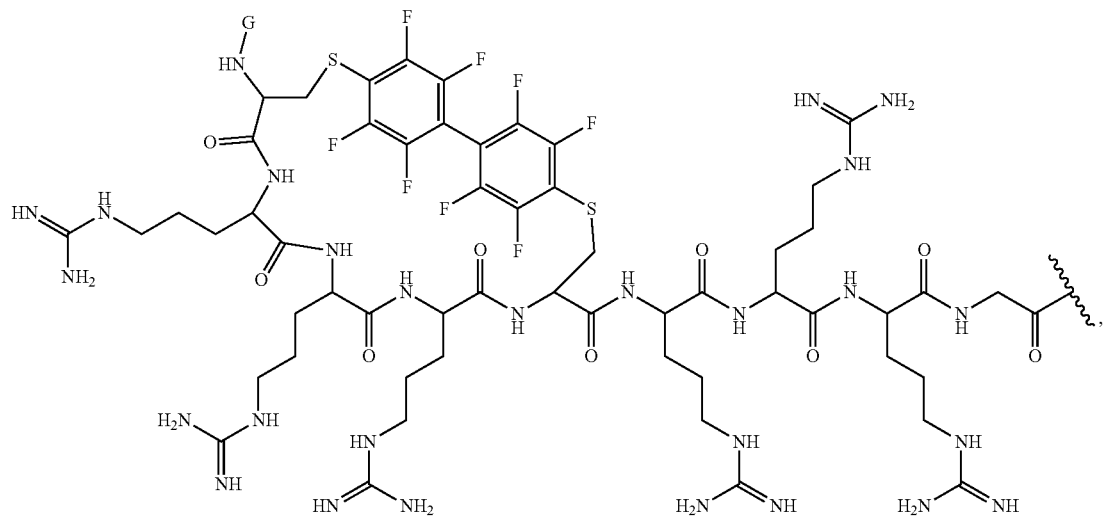

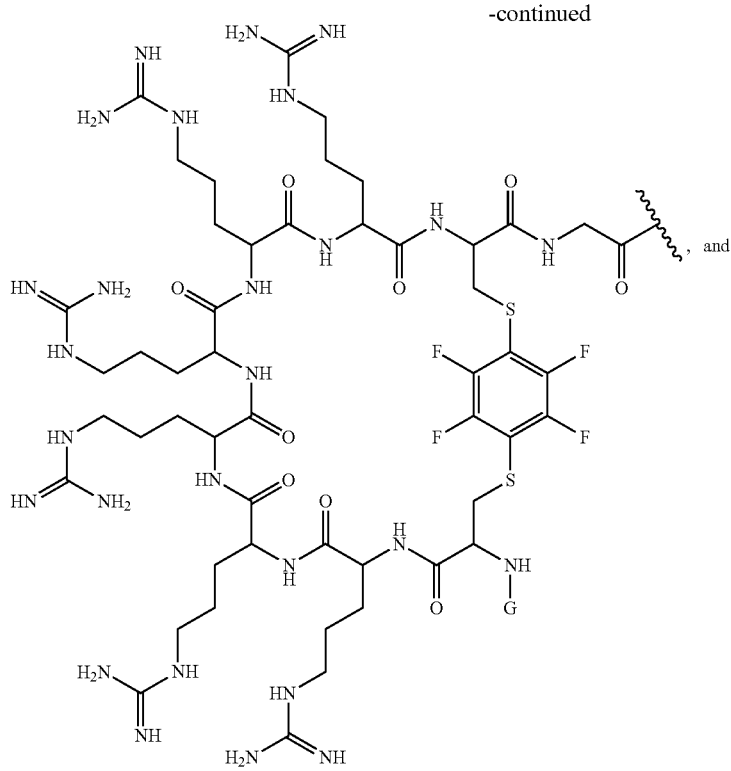, and
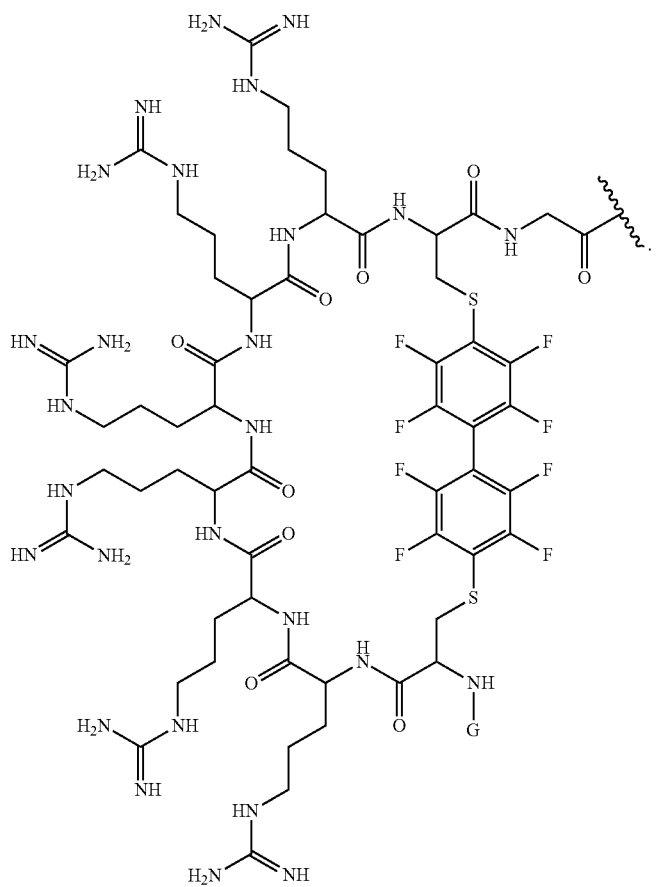.

In still another embodiment, the peptide-oligonucleotide-conjugate of Formula I is a peptide-oligonucleotide-conjugate of Formula Ic:

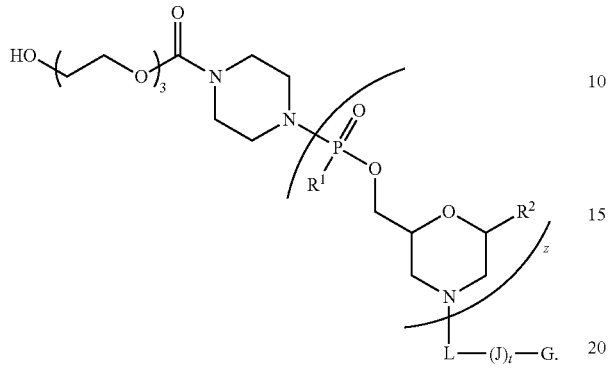
(Ic)

In yet another embodiment, the peptide-oligonucleotide-conjugate of Formula I is a peptide-oligonucleotide-conjugate of Formula Id:

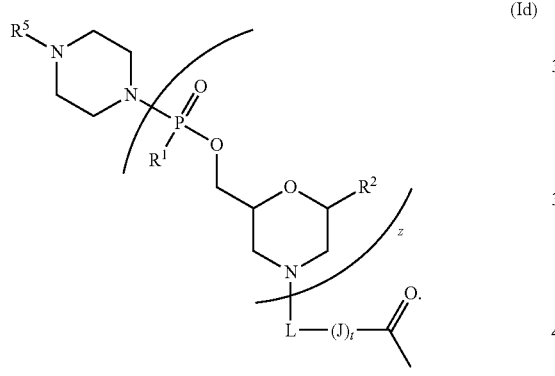
(Id)

In another embodiment, the peptide-oligonucleotide-conjugate of Formula I is a peptide-oligonucleotide-conjugate of Formula Ie:

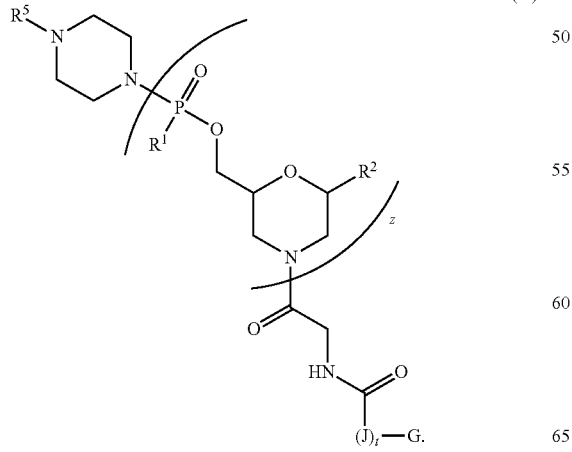
(Ie)

In another aspect, provided herein is a peptide-oligonucleotide-conjugate of Formula IV:

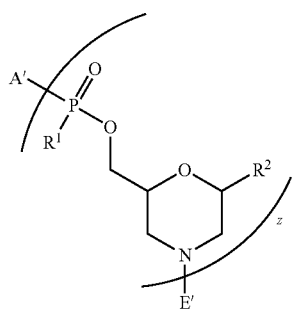
(IV)

or a pharmaceutically acceptable salt thereof,
wherein:
A' is selected from —NHCH$_2$C(O)NH$_2$, —N(C$_{1-6}$-alkyl)CH$_2$C(O)NH$_2$,

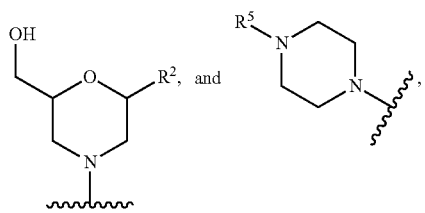

wherein
R$^5$ is —C(O)(O-alkyl)$_x$OH, wherein x is 3-10 and each alkyl group is independently at each occurrence C$_{2-6}$-alkyl, or R$^5$ is selected from —C(O)C$_{1-6}$ alkyl, trityl, monomethoxytrityl, —(C$_{1-6}$-alkyl)R$^6$, —(C$_{1-6}$ heteroalkyl)-R$^6$, aryl-R$^6$, heteroaryl-R$^6$, —C(O)O—(C$_{1-6}$ alkyl)-R$^6$, —C(O)O-aryl-R$^6$, —C(O)O— heteroaryl-R$^6$, and

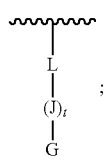
;

wherein R$^6$ is selected from OH, SH, and NH$_2$, or R$^6$ is O, S, or NH, covalently linked to a solid support;
each R$^1$ is independently selected from OH and —NR$^3$R$^4$, wherein each R$^3$ and R$^4$ are independently at each occurrence —C$_{1-6}$ alkyl;
each R$^2$ is independently selected from H, a nucleobase, and a nucleobase functionalized with a chemical protecting-group, wherein the nucleobase independently at each occurrence comprises a C$_{3-6}$ heterocyclic ring selected from pyridine, pyrimidine, triazinane, purine, and deaza-purine;
z is 8-40; and
E' is selected from H, —C$_{1-6}$ alkyl, —C(O)C$_{1-6}$ alkyl, benzoyl, stearoyl, trityl, monomethoxytrityl, dimethoxytrityl, trimethoxytrityl,

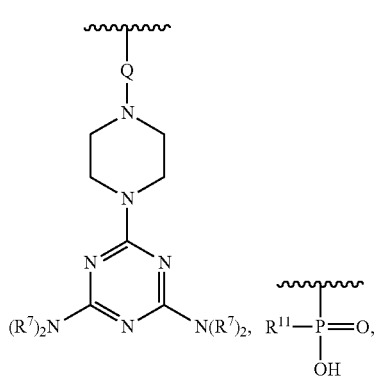

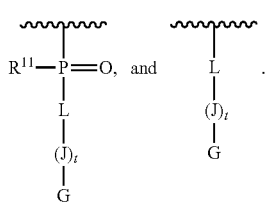

wherein
Q is —C(O)(CH$_2$)$_6$C(O)— or —C(O)(CH$_2$)$_2$S$_2$(CH$_2$)$_2$C(O)—,
R$^7$ is —(CH$_2$)$_2$OC(O)N(R$^8$)$_2$, wherein R$^8$ is —(CH$_2$)$_6$NHC(=NH)NH$_2$, and
R$^{11}$ is selected from OH and —NR$^3$R$^4$,
wherein L is covalently linked by an amide bond to the carboxy-terminus of J, and L is selected from —NH(CH$_2$)$_{1-6}$C(O)—, —NH(CH$_2$)$_{1-6}$C(O)NH(CH$_2$)$_{1-6}$C(O)—, and

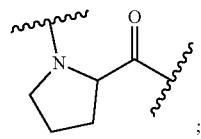 [SMILES: *C(=O)C1CCCN1*]

t is 4-9;
each J is independently at each occurrence selected from an amino acid of the

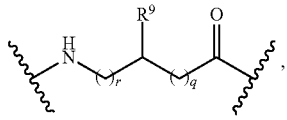

structure
wherein:
r and q are each independently 0, 1, 2, 3, or 4; and
each R$^9$ is independently at each occurrence selected from H, an amino acid side-chain, and an amino acid side-chain functionalized with a chemical protecting-group,
wherein two or more amino acid side-chain groups of R$^9$ independently at each occurrence comprise a sulfur, wherein two of the sulfur atoms, together with the atoms to which they are attached, form the structure

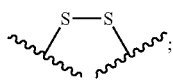

and

G is covalently linked to the amino-terminus of J, and G is selected from
H, —C(O)C$_{1-6}$ alkyl, benzoyl, and stearoyl, and
wherein at least one of the following conditions is true:
1) A' is

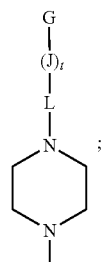

2) E' is

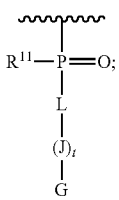

or 3) E' is

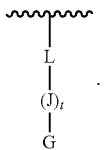

In an embodiment of Formula IV, d is 1.
In another embodiment of Formula IV, E' is selected from H, —C(O)CH$_3$, and

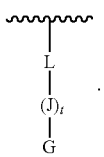

In still another embodiment of Formula IV, A' is selected from —N(C$_{1-6}$-alkyl)CH$_2$C(O)NH$_2$,

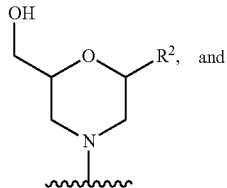

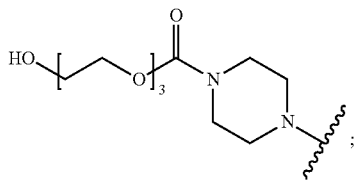

E' is

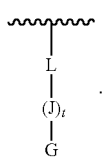

In yet another embodiment of Formula IV, A' is

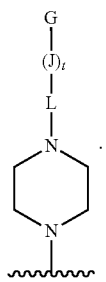

In another embodiment of Formula IV, E' is selected from H and —C(O)CH$_3$.

In still another embodiment of Formula IV, M is

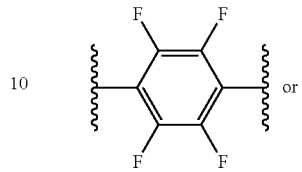

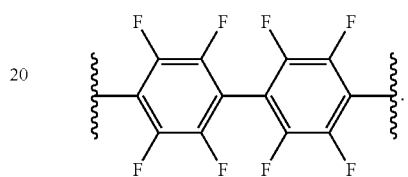

In still another embodiment of Formula IV, each J is independently at each occurrence selected from an α-amino acid, a β$^2$-amino acid, and a β$^3$-amino acid.

In yet another embodiment of Formula IV, r and q are each 0.

In another embodiment of Formula IV, J is independently selected from cysteine and arginine.

In another embodiment of Formula IV, z is 15-25.

In yet another embodiment of Formula IV, z is 10-20.

In still another embodiment of Formula IV, each R$^1$ is N(CH$_3$)$_2$.

In yet another embodiment of Formula IV, each R$^2$ is a nucleobase independently at each occurrence selected from adenine, guanine, cytosine, 5-methyl-cytosine, thymine, uracil, and hypoxanthine.

In yet another embodiment of Formula IV, L is glycine.

In yet another embodiment of Formula IV, G is selected from H, C(O)CH$_3$, benzoyl, and stearoyl.

In yet another embodiment of Formula IV, G is —C(O)CH$_3$.

In yet another embodiment, the oligonucleotide comprises a targeting sequence having sequence complementarity to an RNA target. In a specific embodiment, the RNA target is a cellular RNA target. In another specific embodiment, the targeting sequence has sufficient sequence complementarity to bind to the RNA target. In yet another specific embodiment, the targeting sequence has perfect sequence complementarity to the RNA target.

Representative

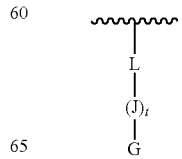

moieties of the disclosure include, amongst others, moieties of the following formulae:
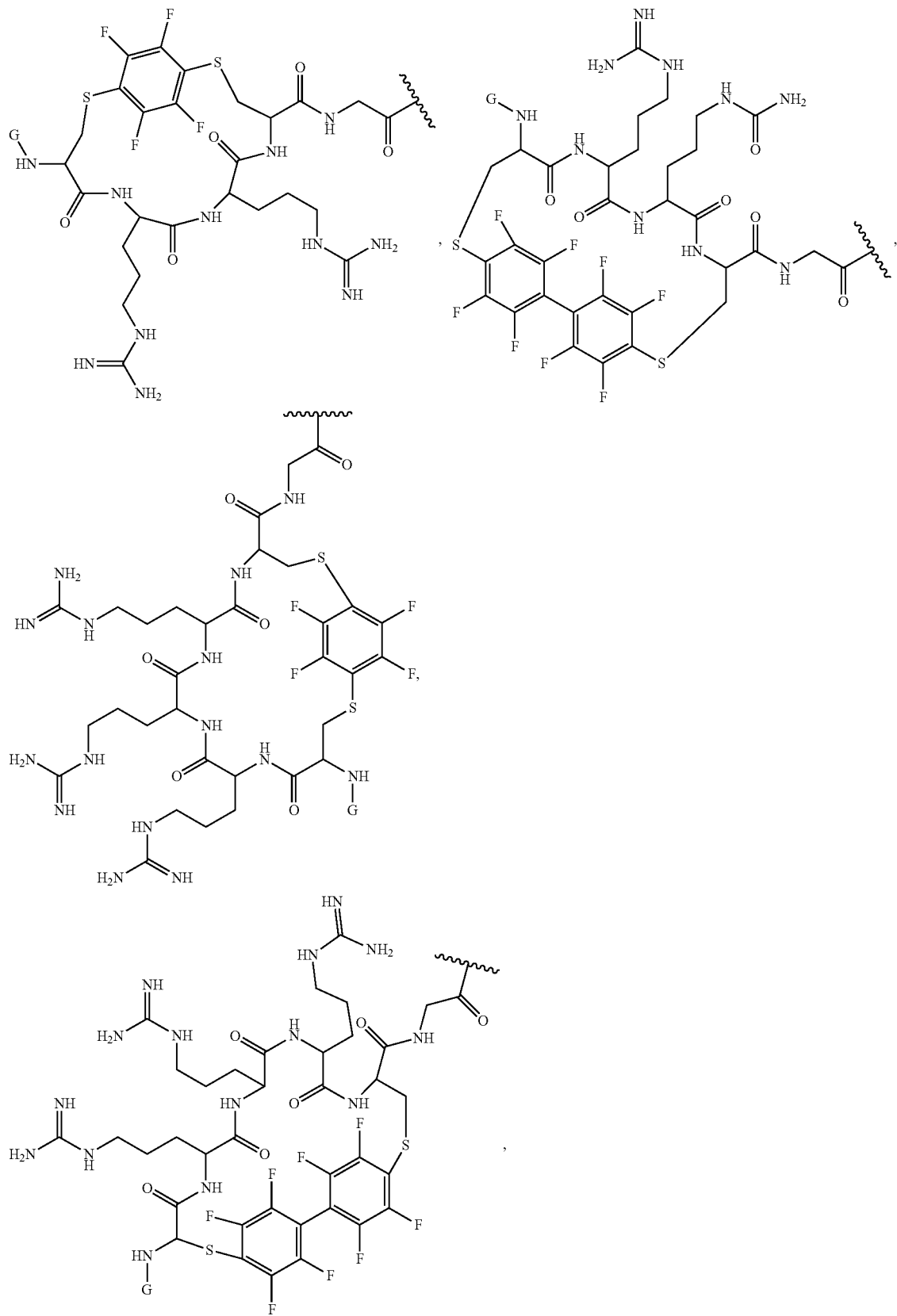

-continued
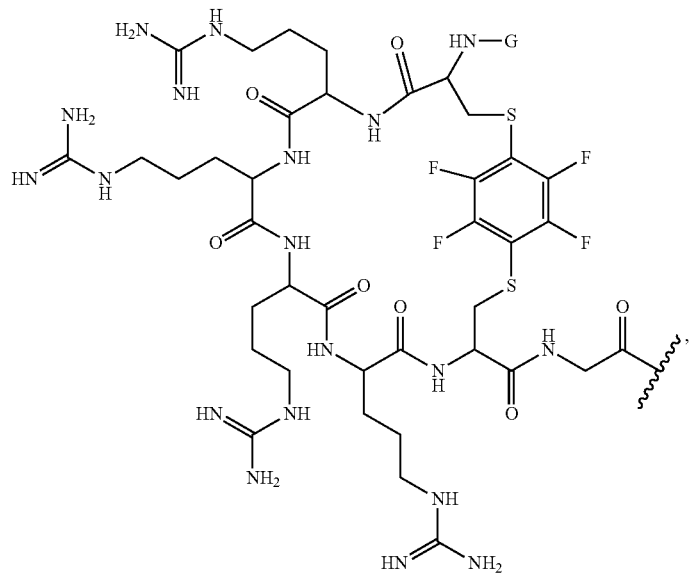
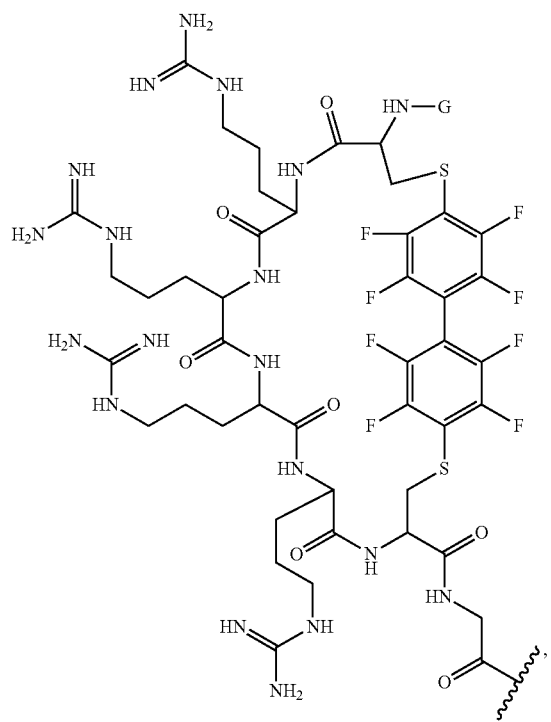

-continued
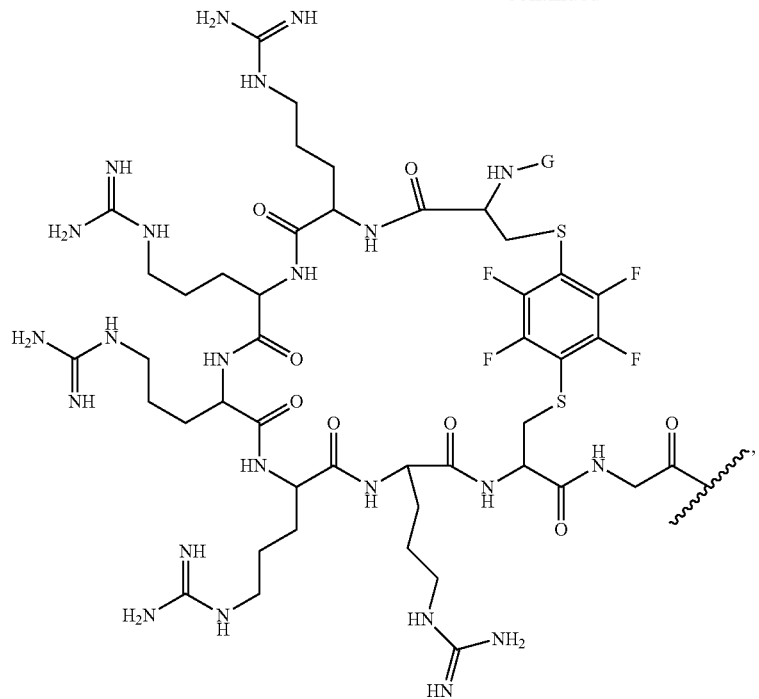
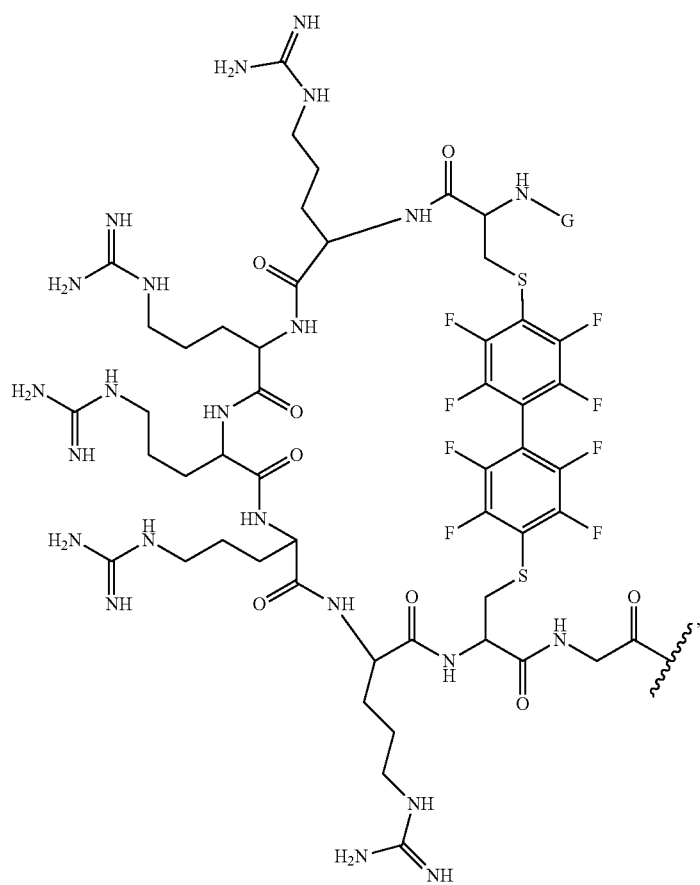

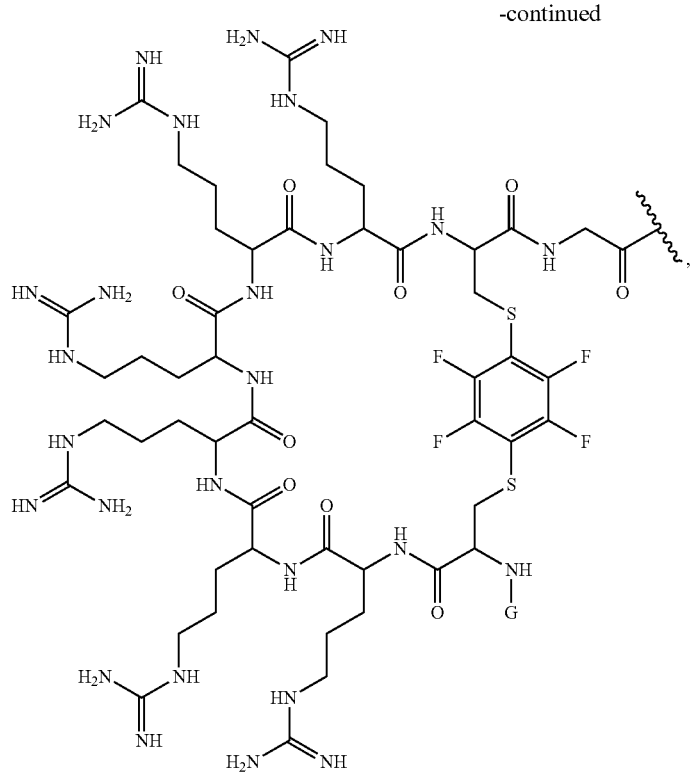
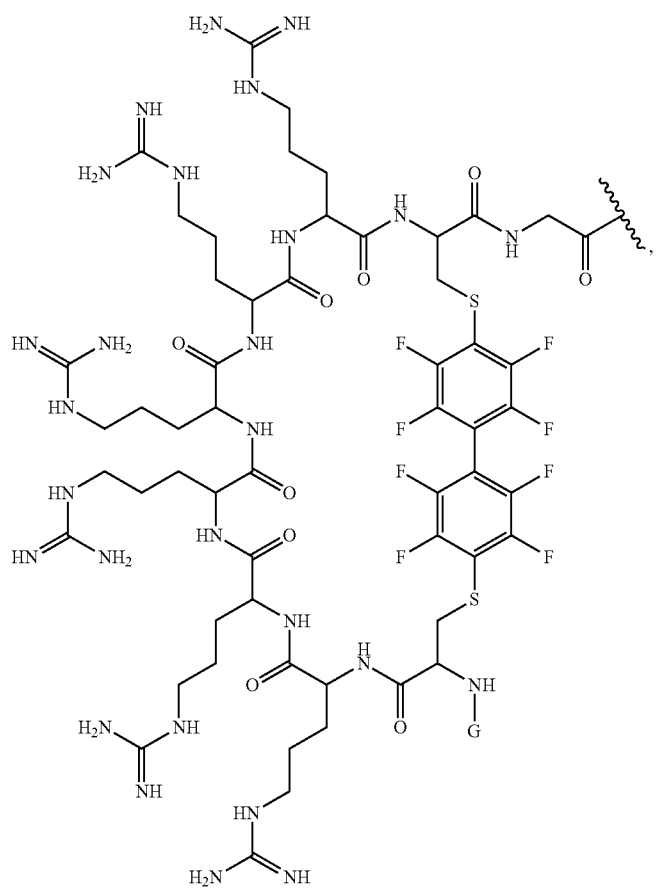

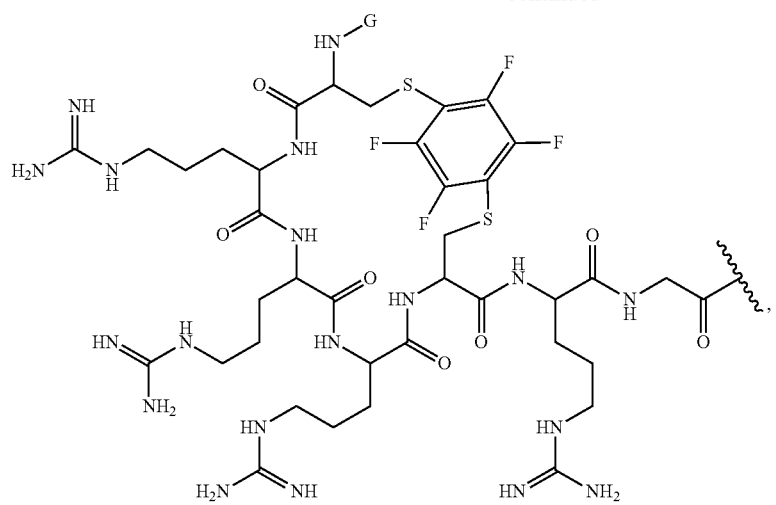
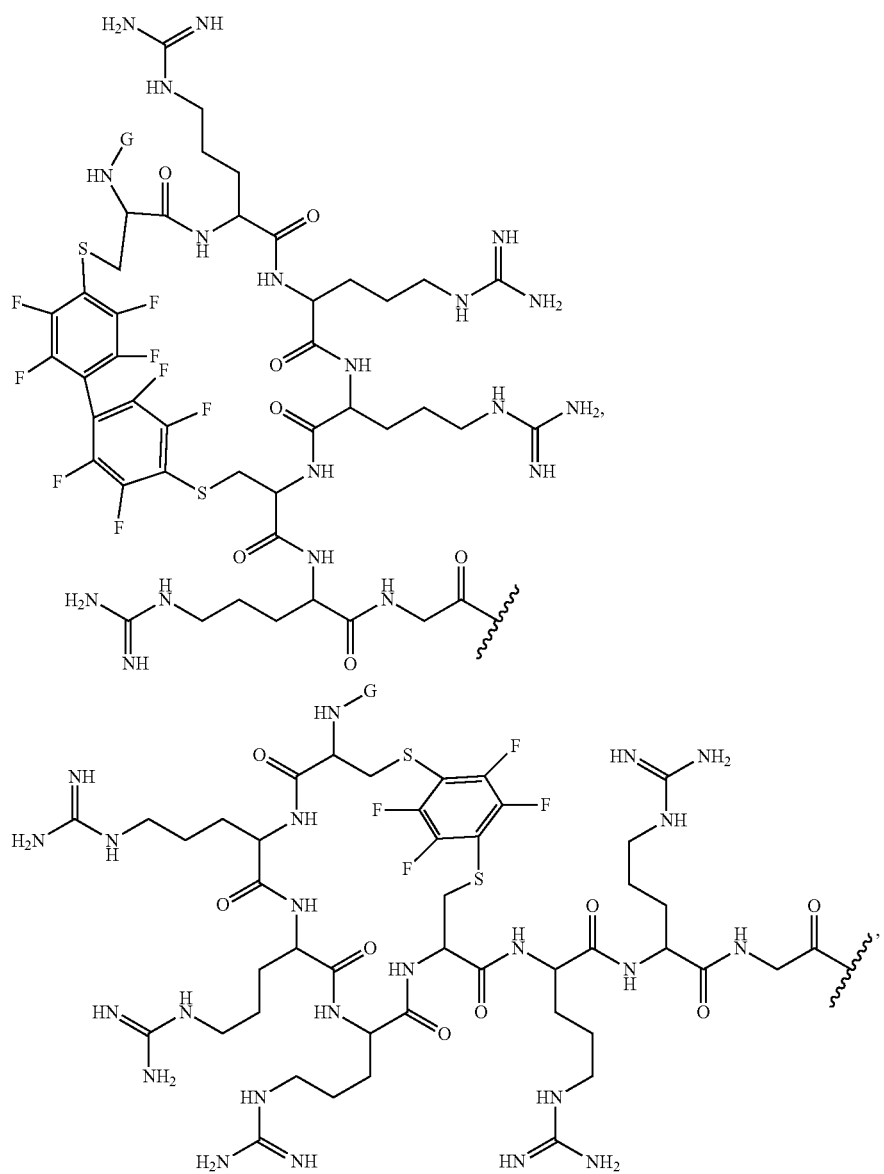

-continued
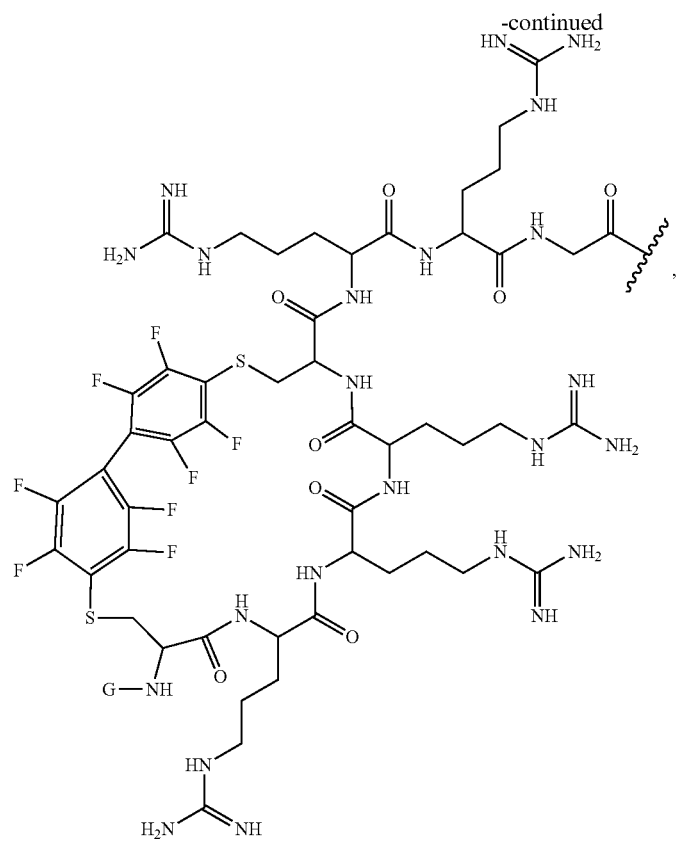
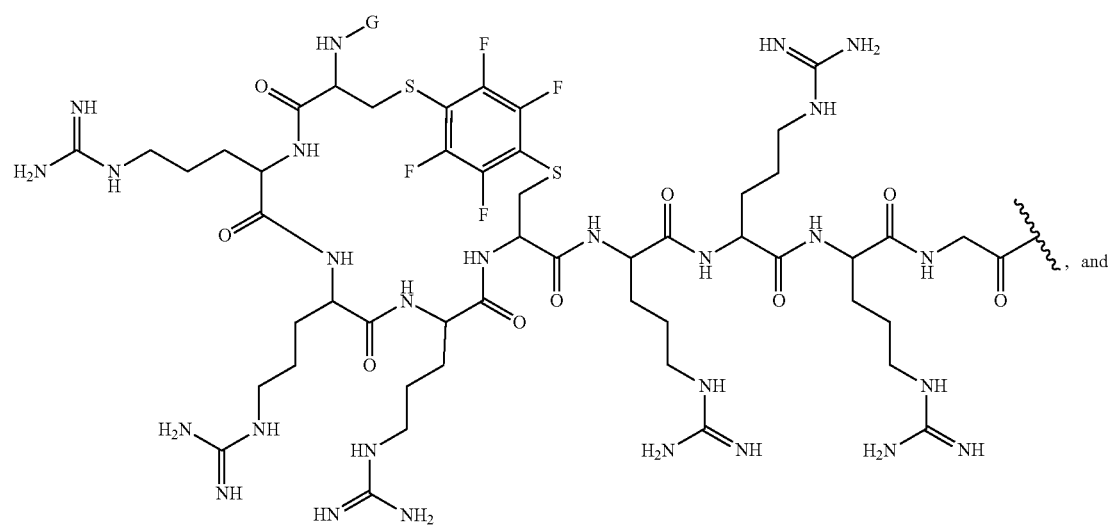

-continued
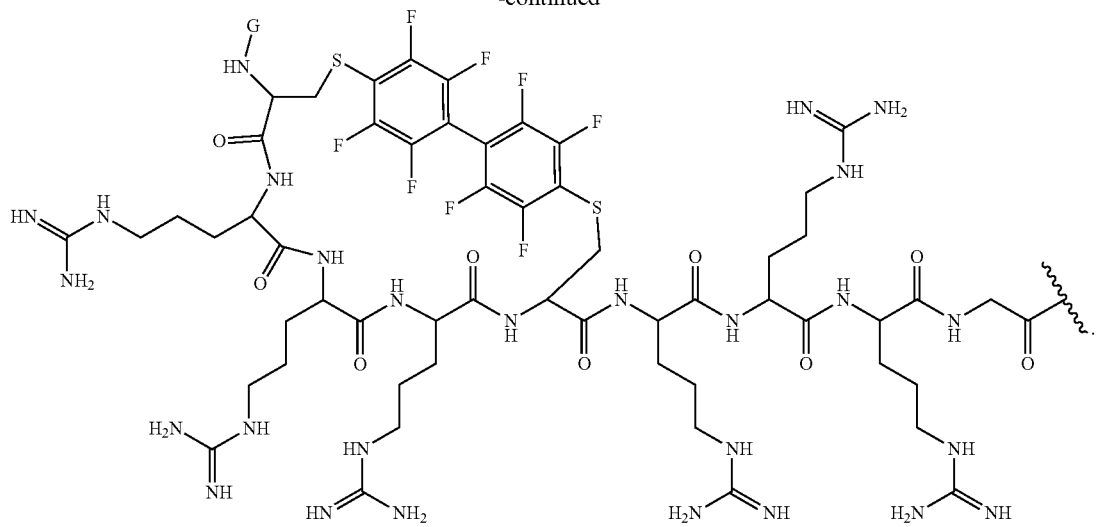
Representative peptide-oligonucleotide-conjugates of the disclosure include, amongst others, peptide-oligonucleotide-conjugates of the following structures:
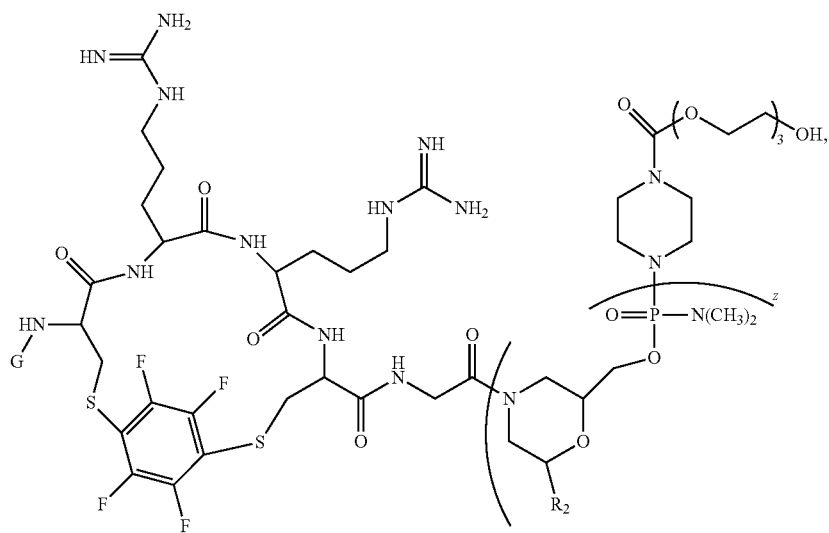

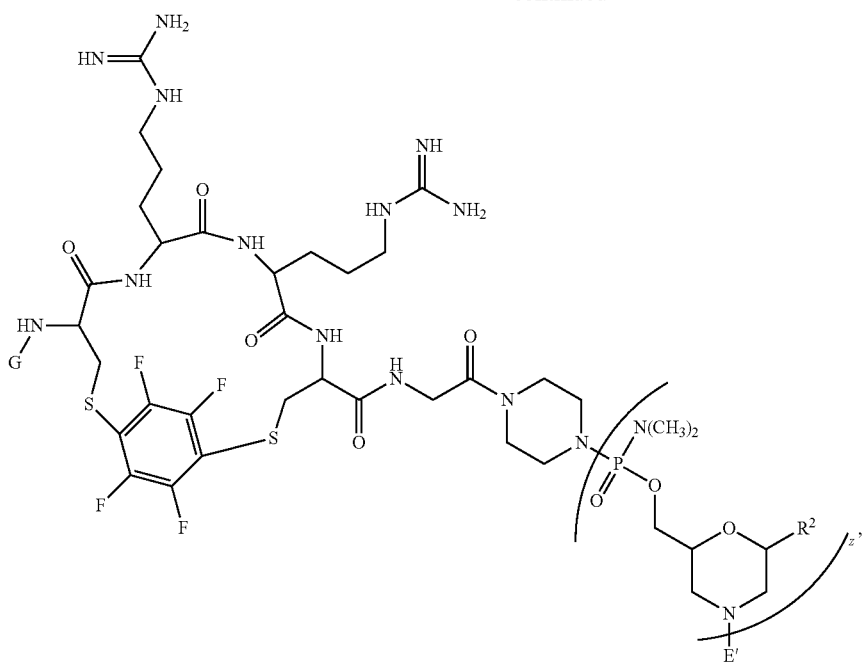
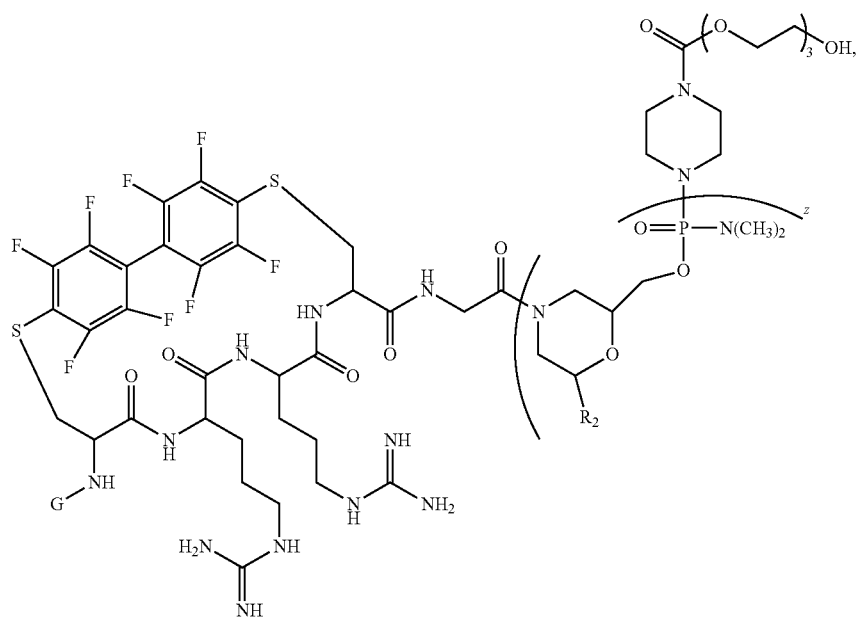

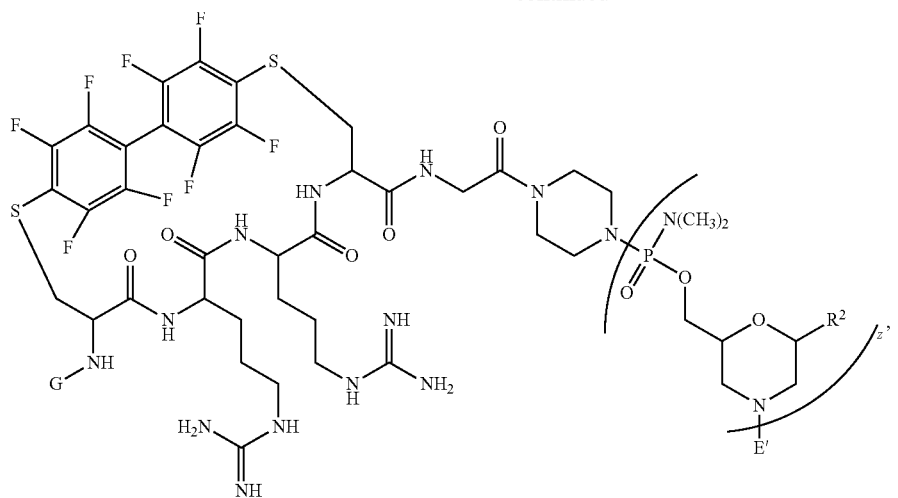
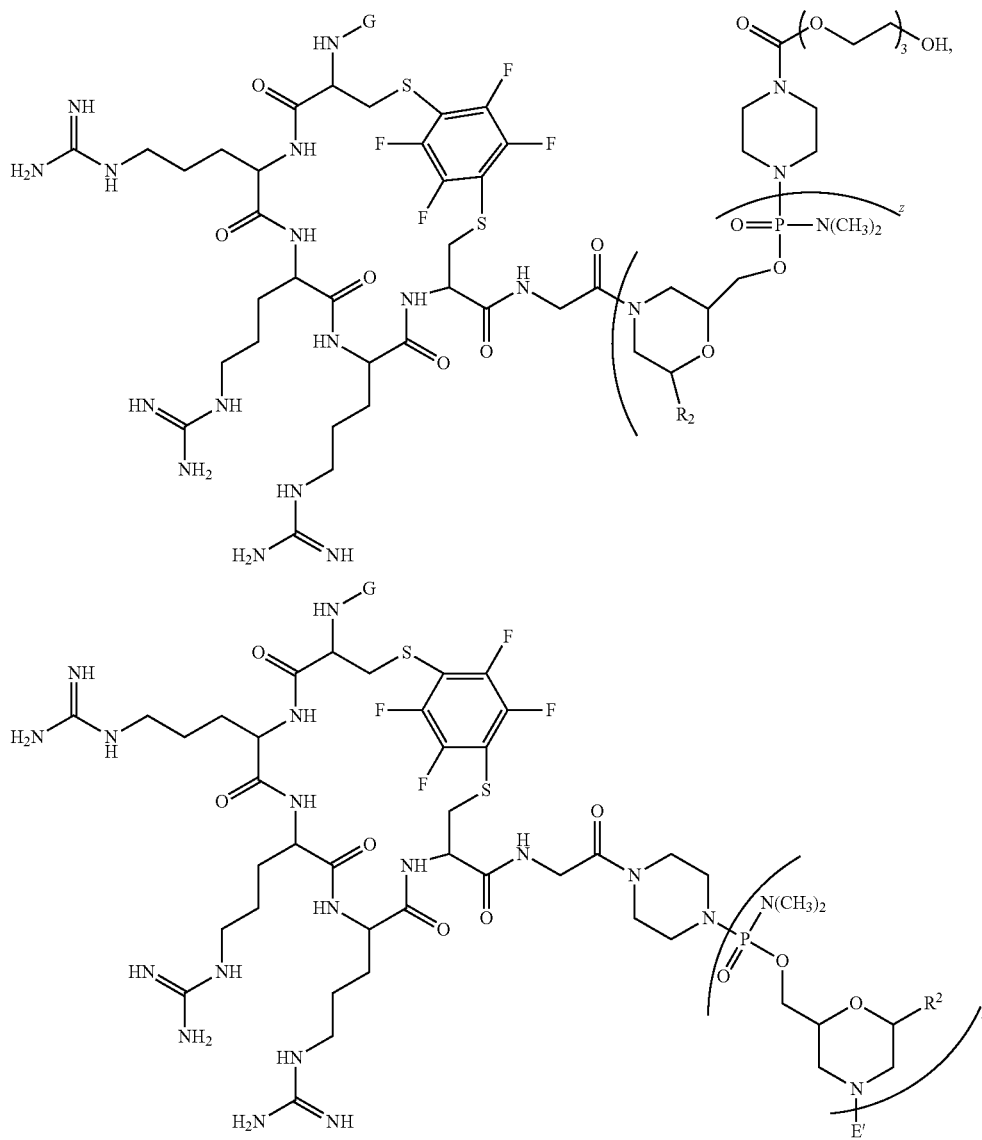

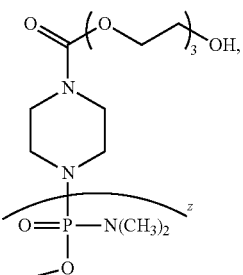
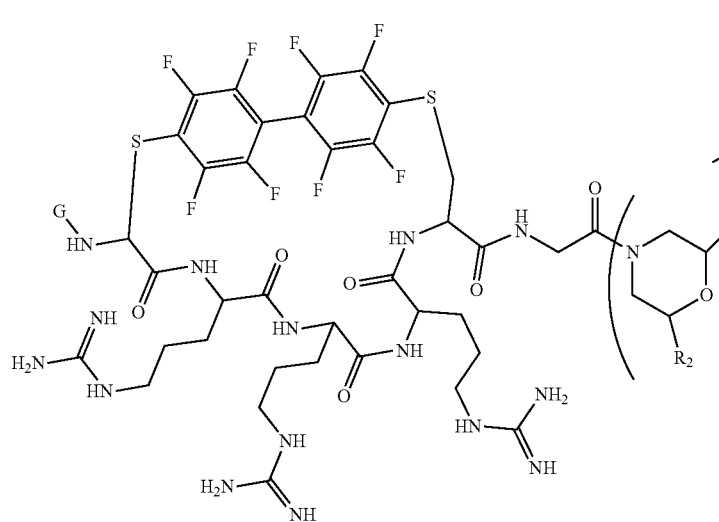
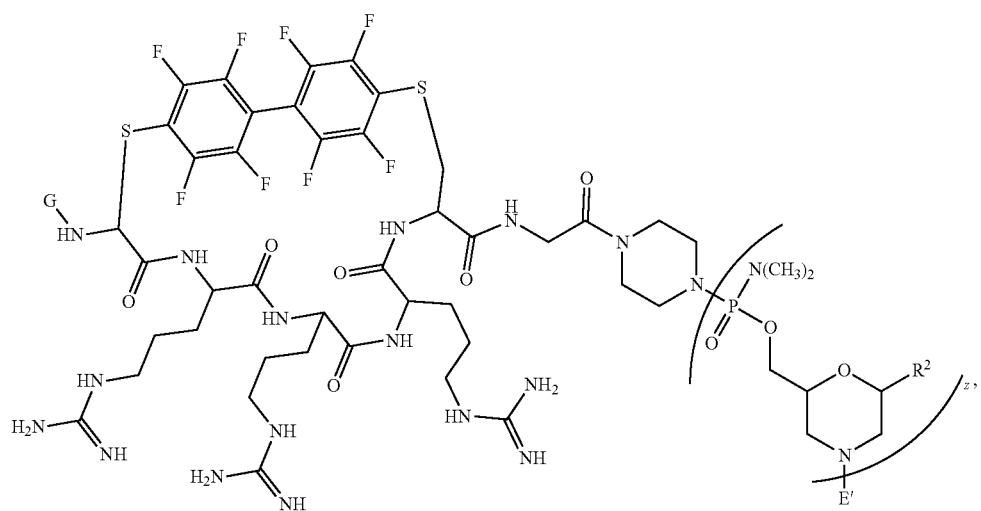

-continued
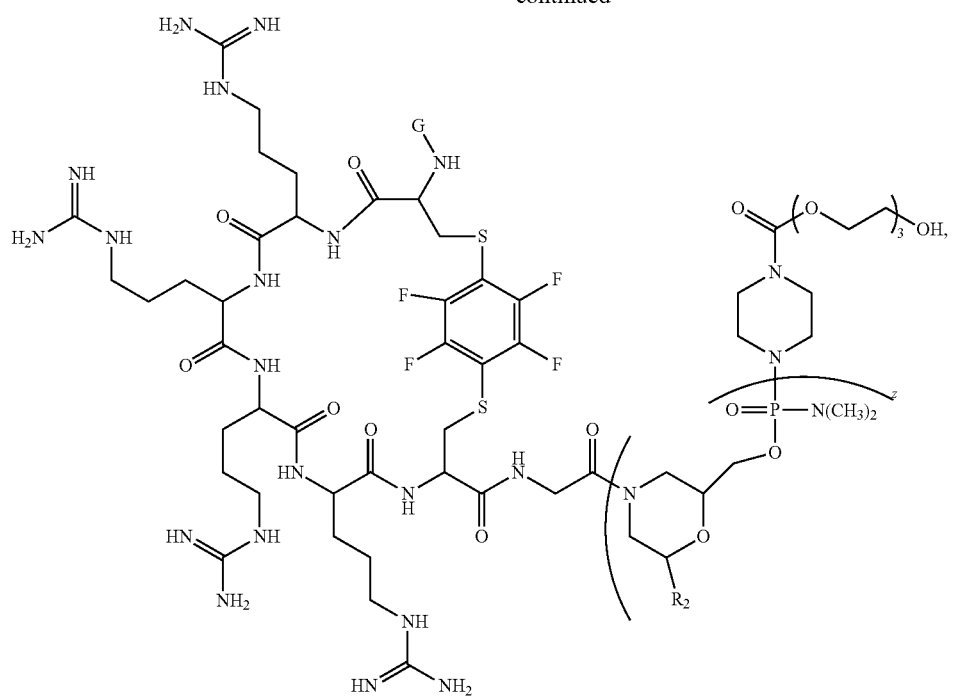
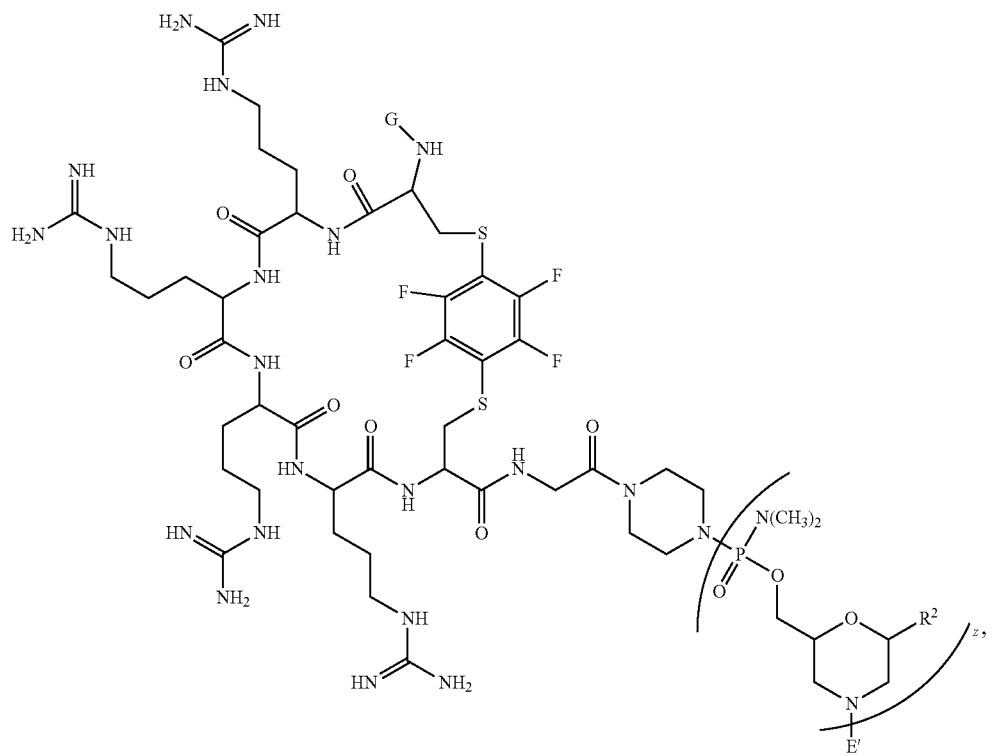

-continued
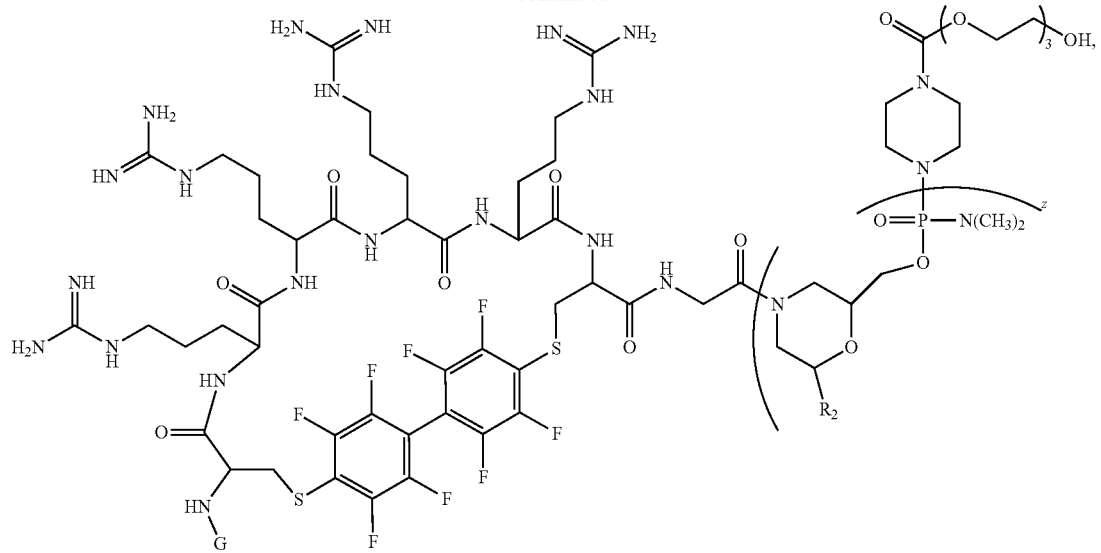
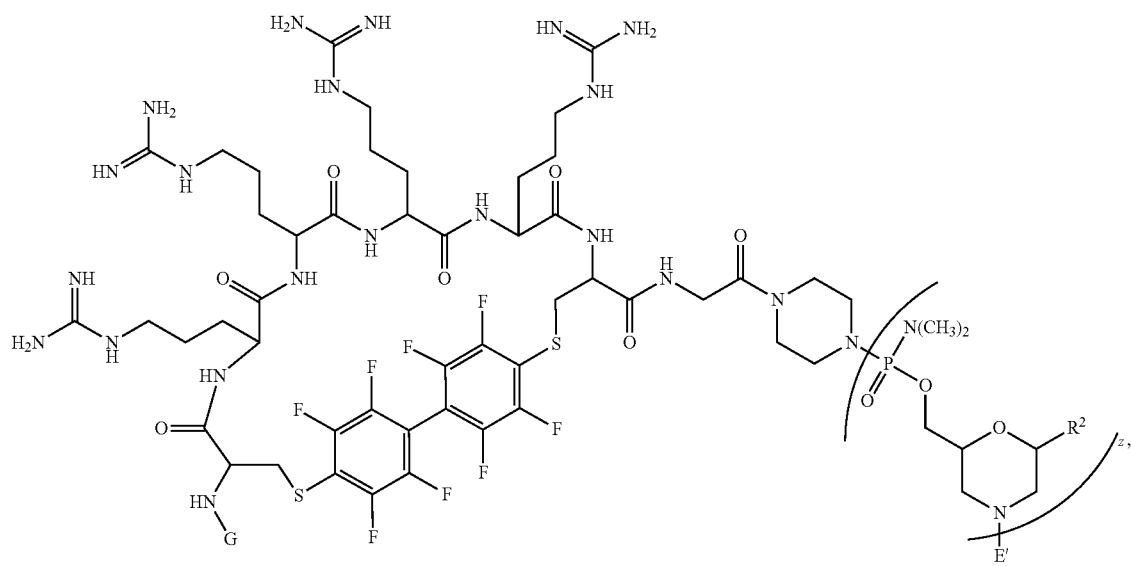

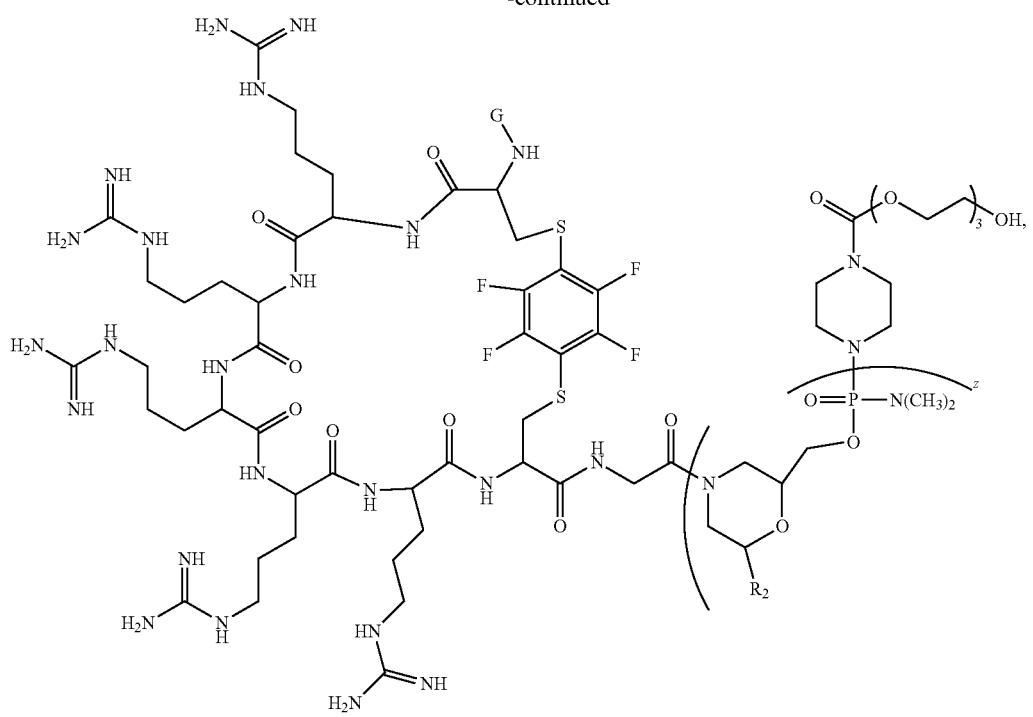
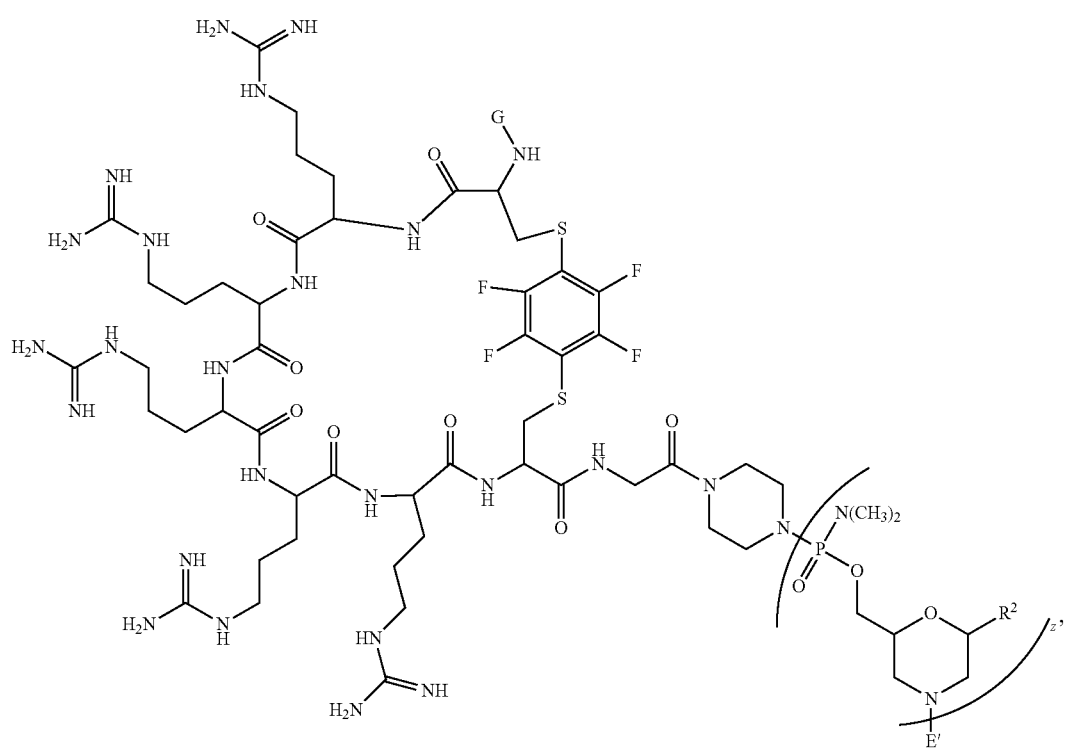

-continued
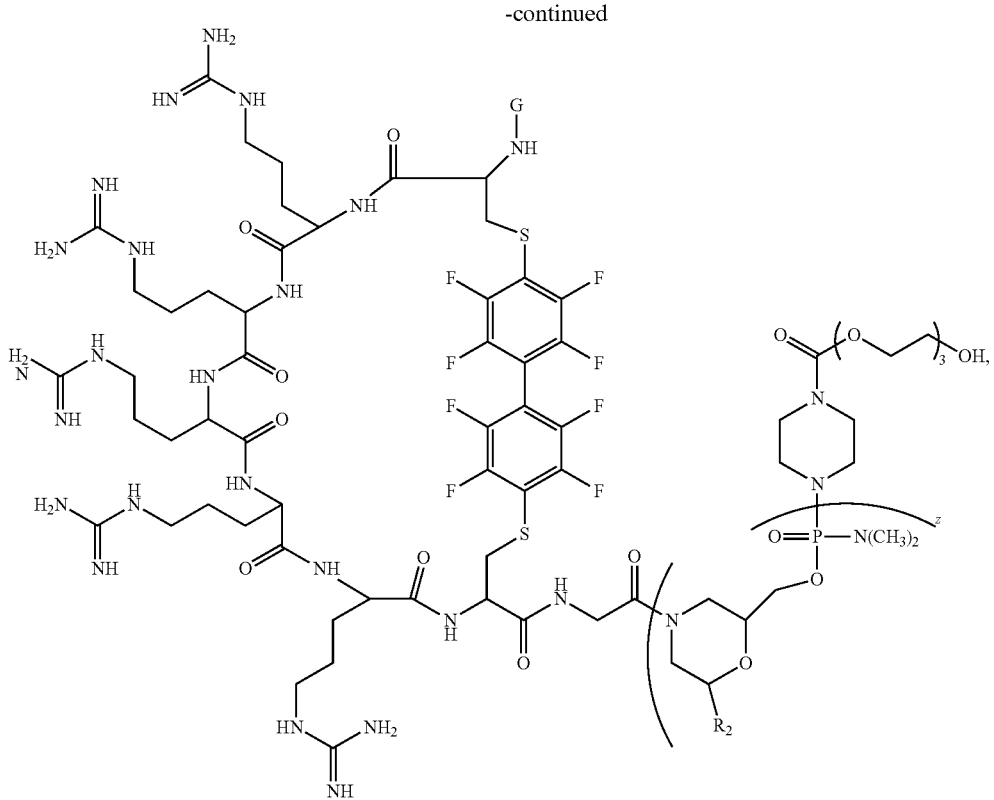
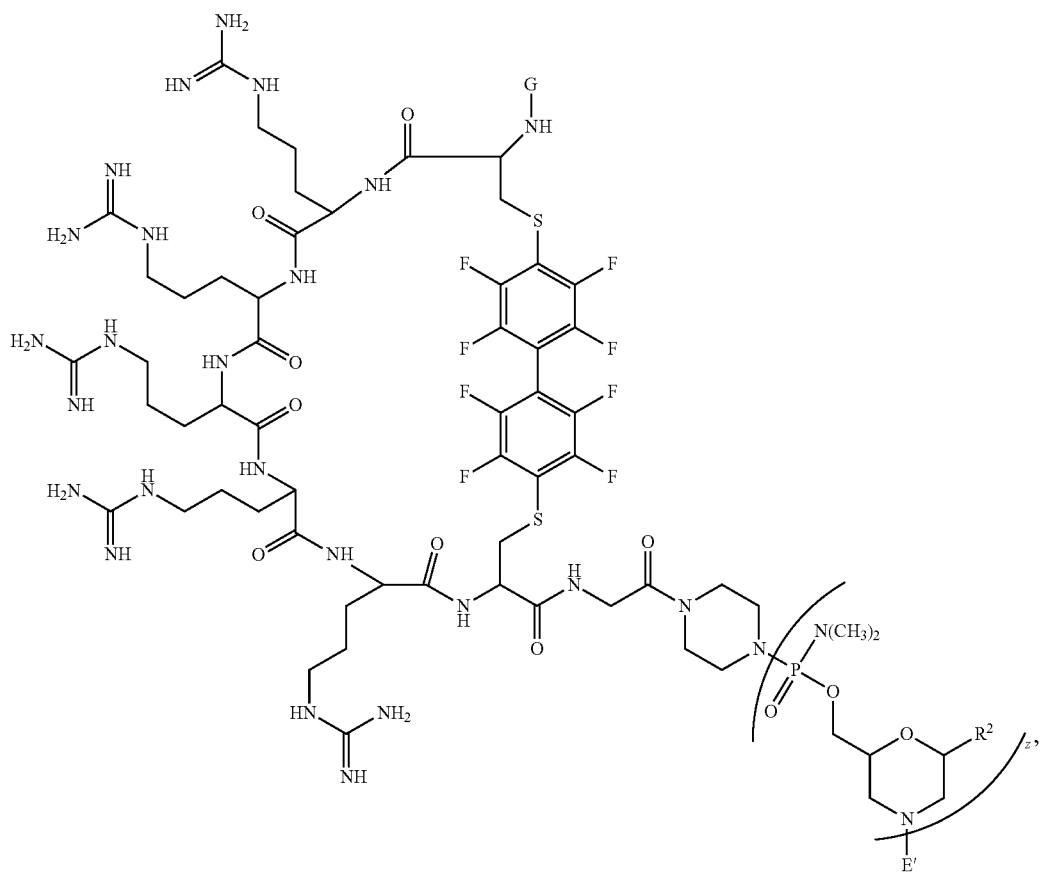

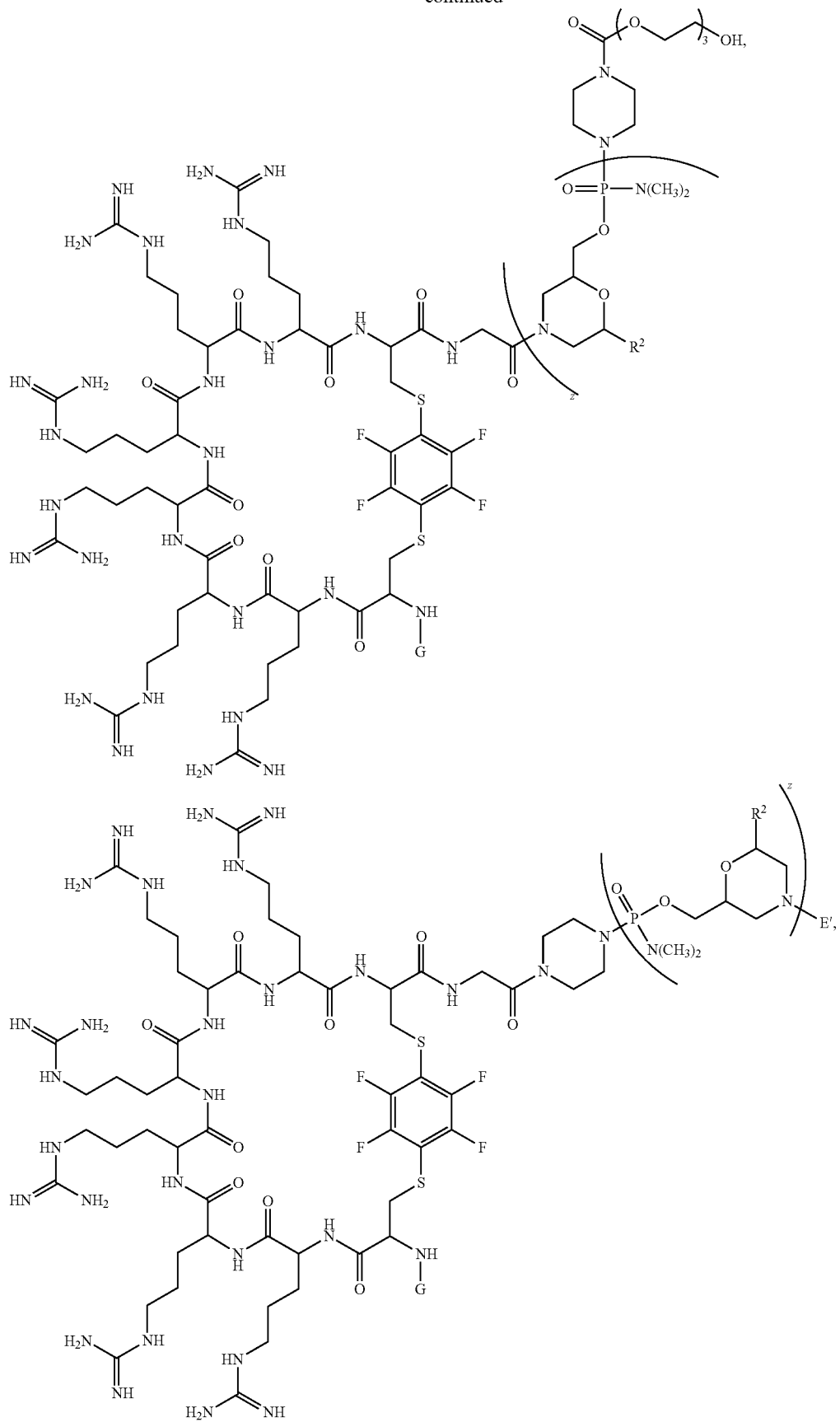

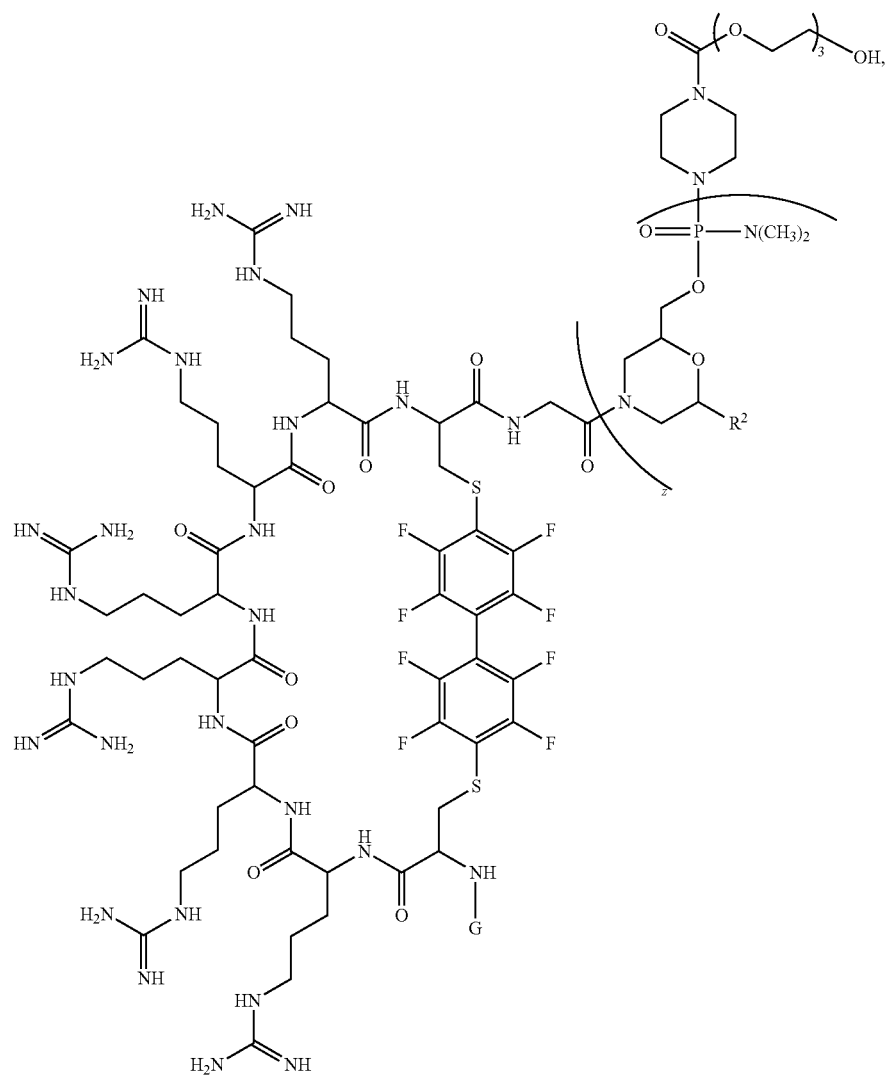

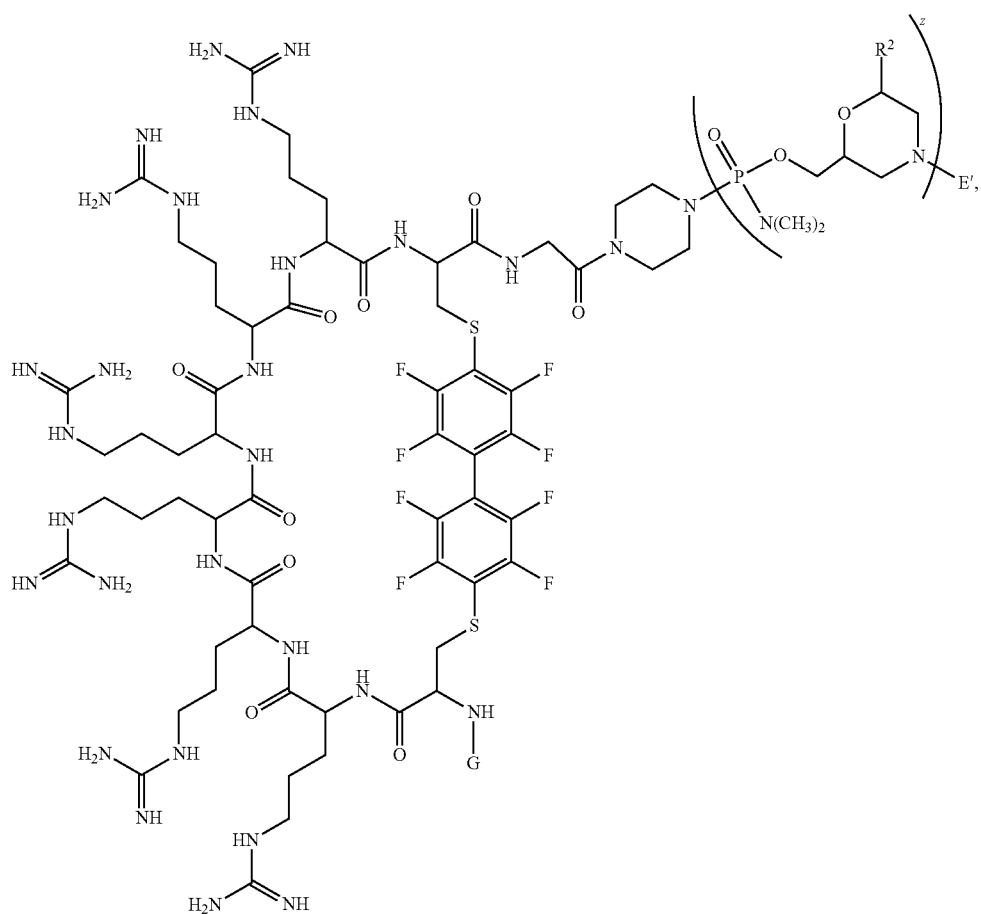
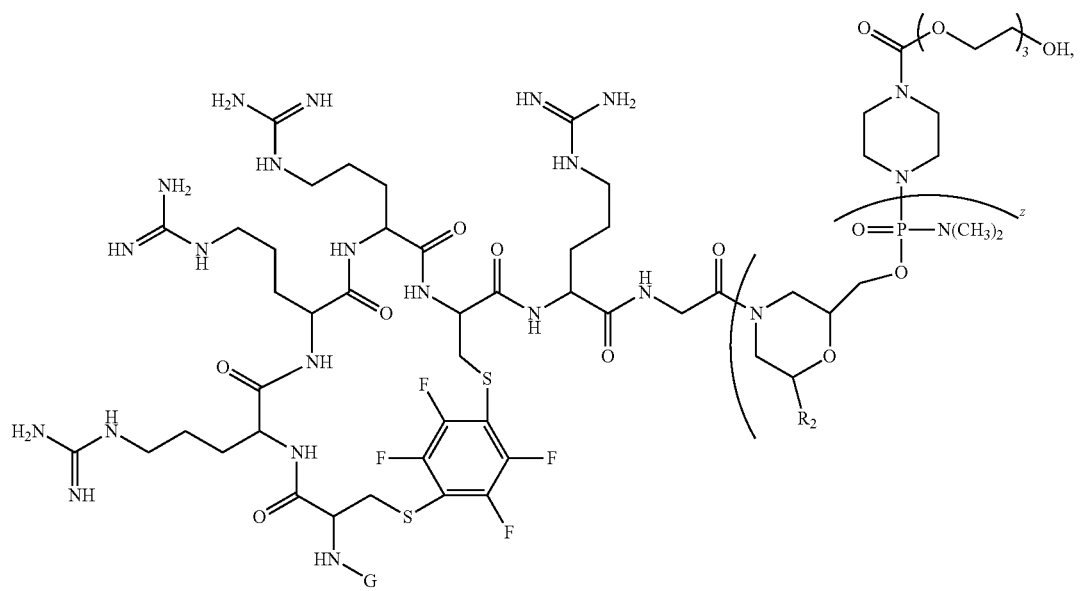

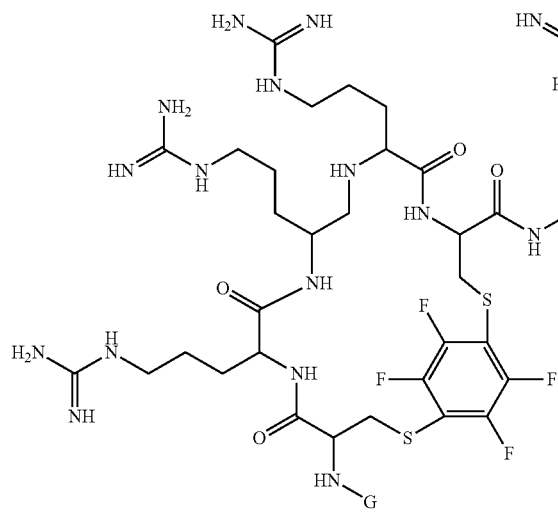
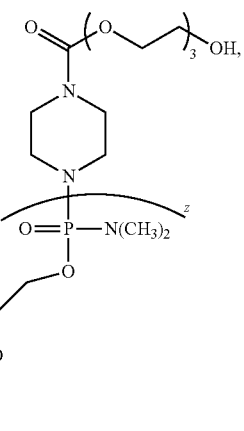
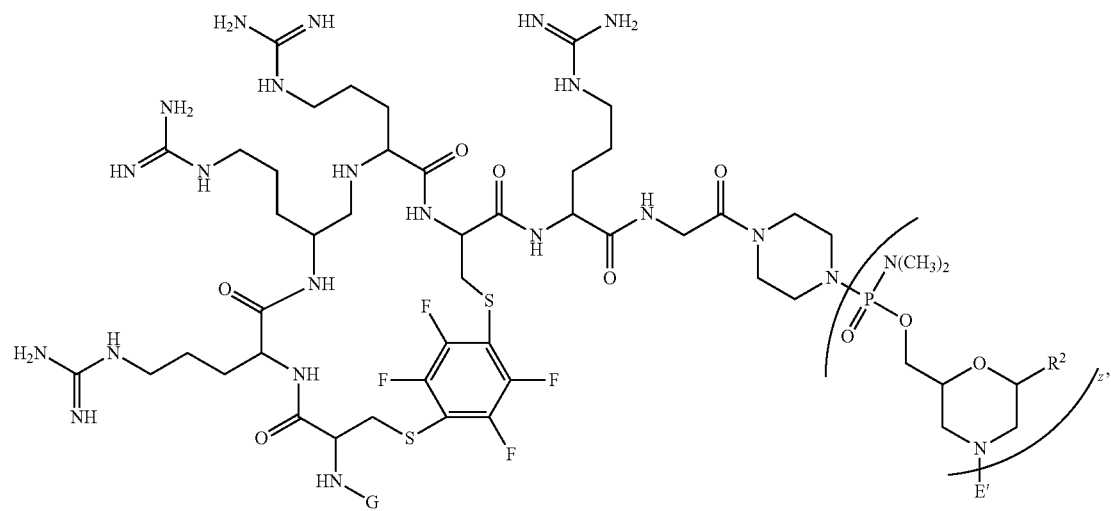

-continued
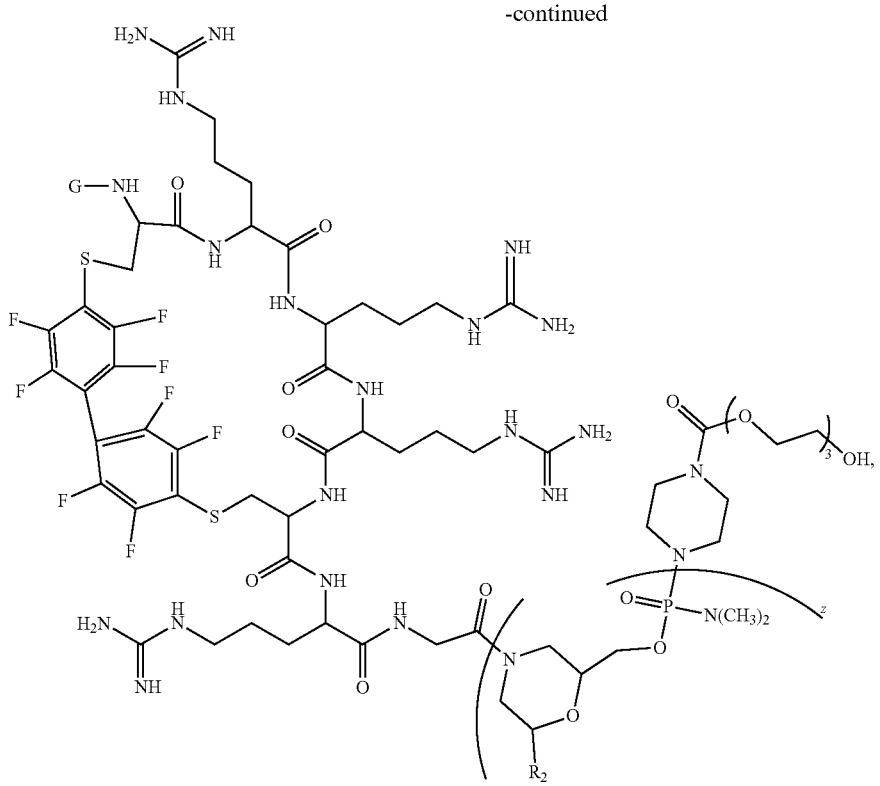
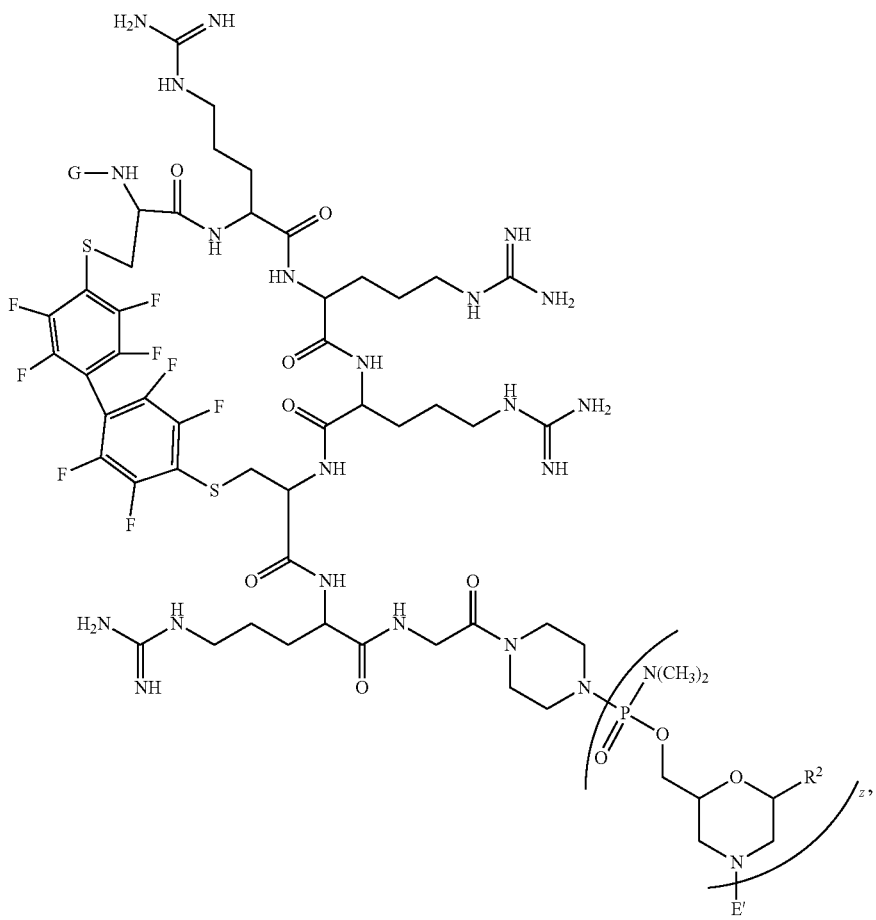

71
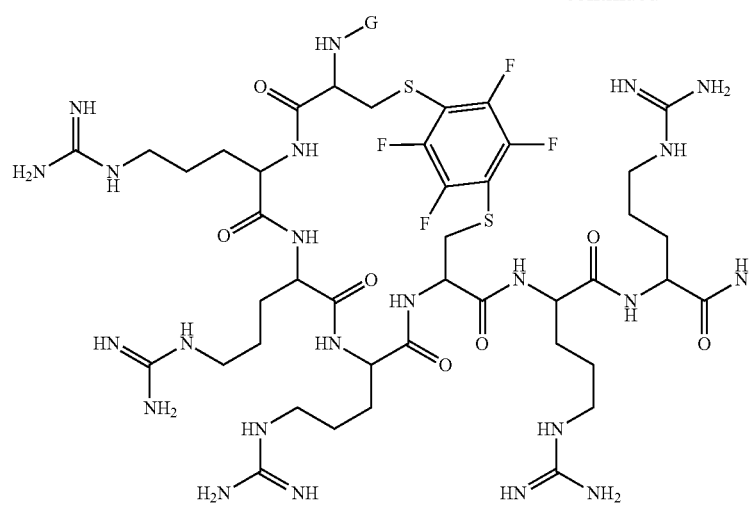 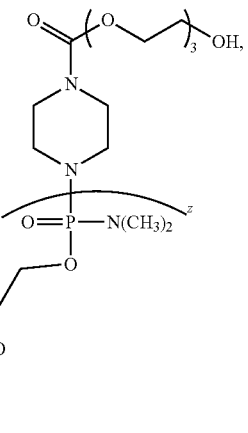
72
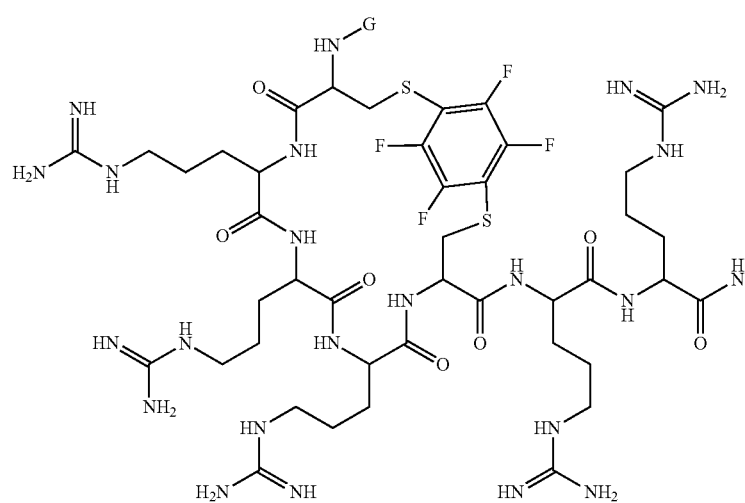 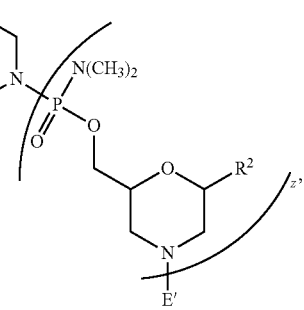

-continued
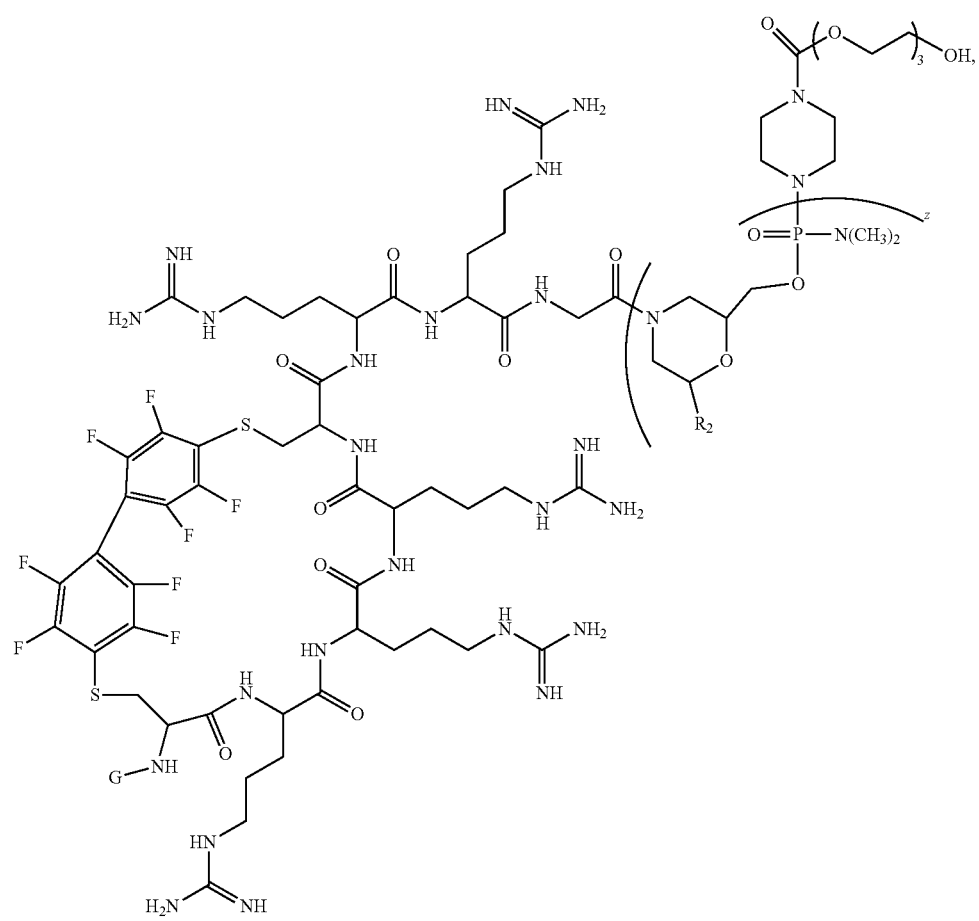

-continued
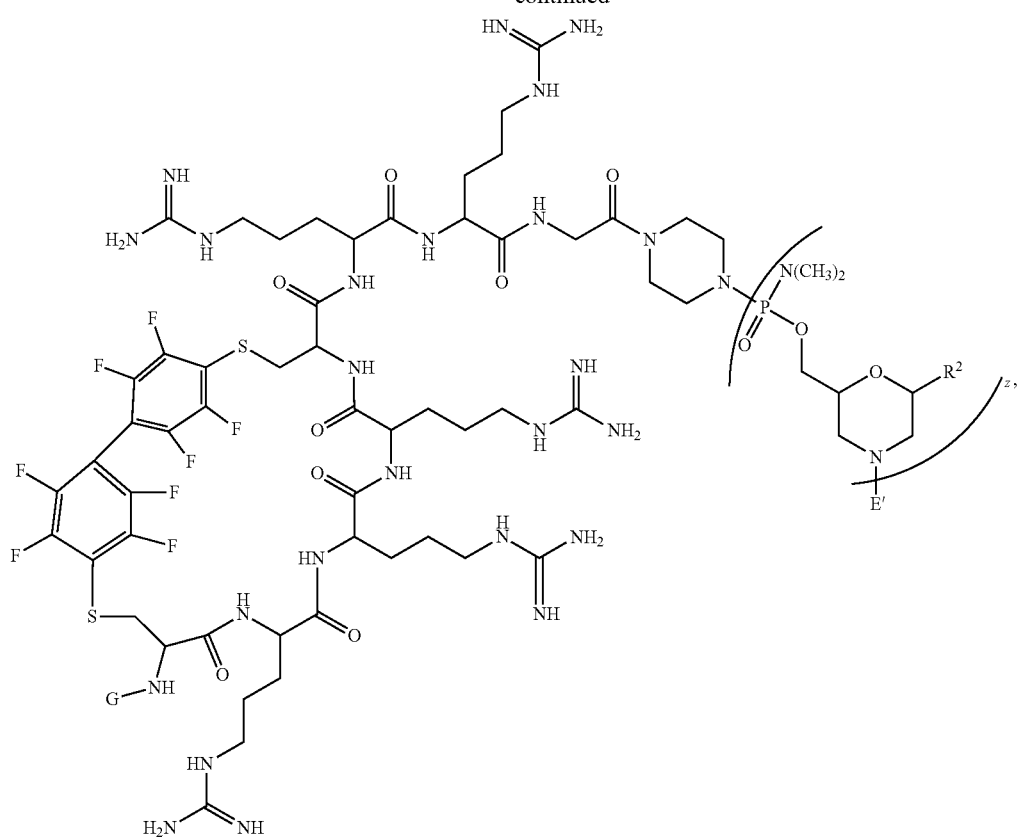
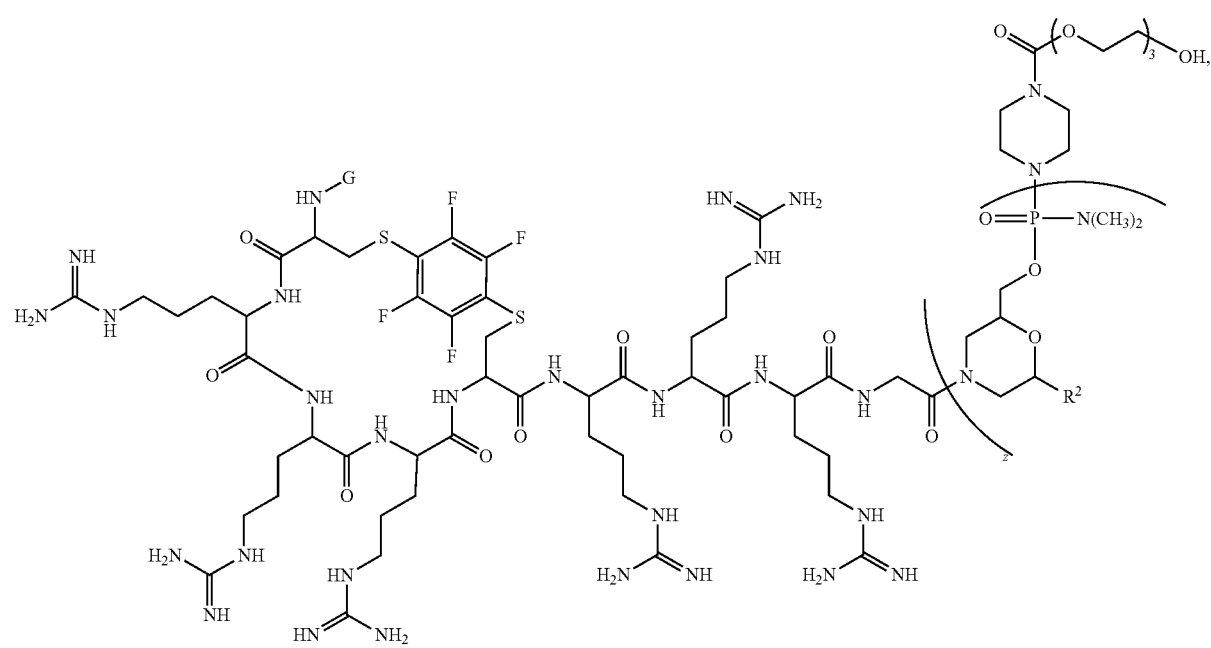

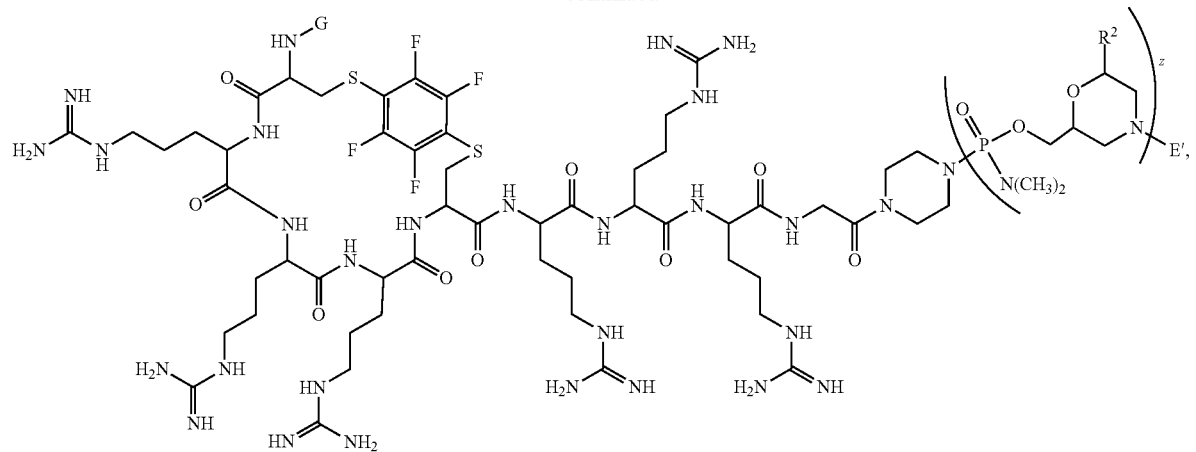
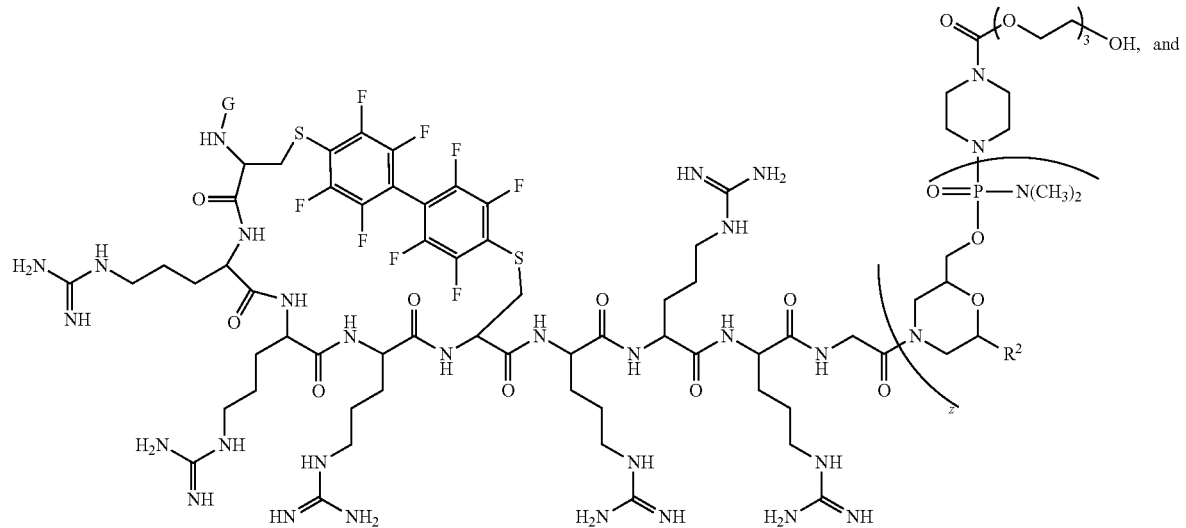
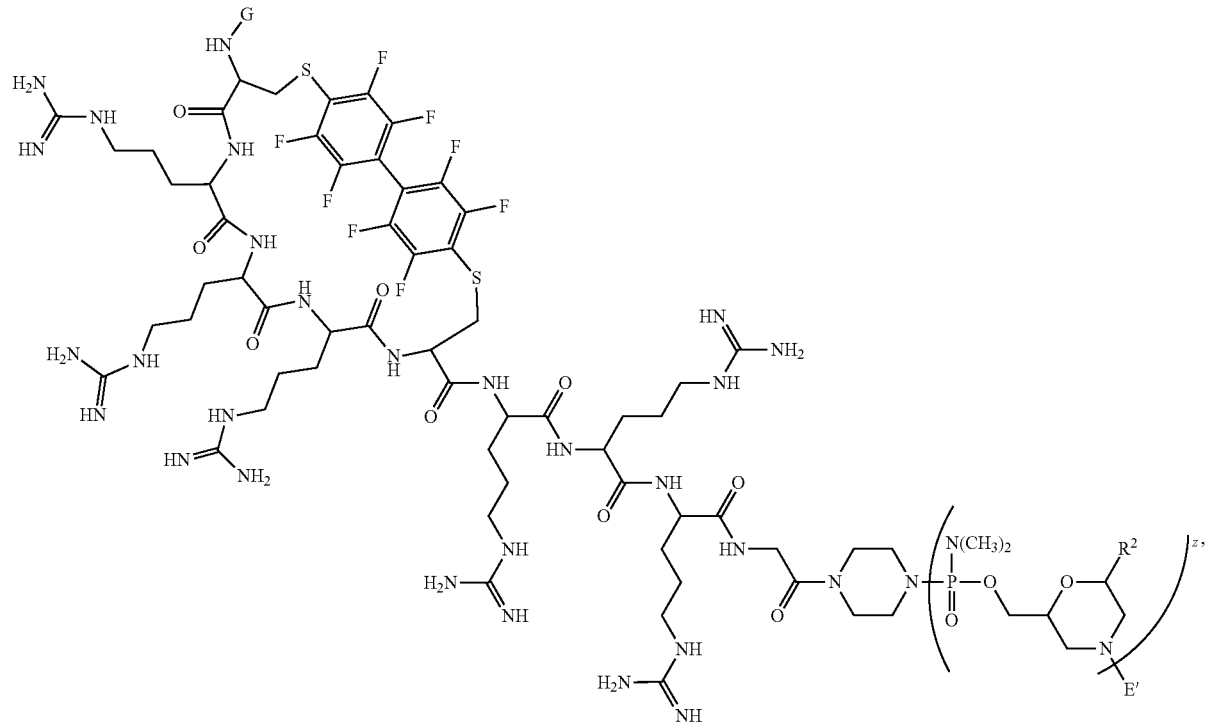

, or a pharmaceutically acceptable salt thereof, wherein
G is selected from H and —C(O)CH$_3$, and
E' is selected from H and —C(O)CH$_3$.

In one embodiment of the peptide-oligonucleotide-conjugates of the disclosure, G is H.

In another embodiment of the peptide-oligonucleotide-conjugates of the disclosure, G is —C(O)CH$_3$.

In still another embodiment of the peptide-oligonucleotide-conjugates of the disclosure, E' is H.

In yet another embodiment of the peptide-oligonucleotide-conjugates of the disclosure, E' is —C(O)CH$_3$.

In still another embodiment of the peptide-oligonucleotide-conjugates of the disclosure, E' and G are —C(O)CH$_3$.

In yet another embodiment of the peptide-oligonucleotide-conjugates of the disclosure, G is —C(O)CH$_3$ and E' is H.

In some embodiments, the peptide-oligonucleotide-conjugates described herein are unsolvated. In other embodiments, one or more of the peptide-oligonucleotide-conjugates are in solvated form. As known in the art, the solvate can be any of pharmaceutically acceptable solvent, such as water, ethanol, and the like.

Although the peptide-oligonucleotide-conjugates of Formulae I, Ia, Ib, Ic, Id, Ie, and IV are depicted in their neutral forms, in some embodiments, these peptide-oligonucleotide-conjugates are used in a pharmaceutically acceptable salt form.

Oligonucleotides

Important properties of morpholino-based subunits include: 1) the ability to be linked in a oligomeric form by stable, uncharged or positively charged backbone linkages; 2) the ability to support a nucleotide base (e.g. adenine, cytosine, guanine, thymidine, uracil, 5-methyl-cytosine and hypoxanthine) such that the polymer formed can hybridize with a complementary-base target nucleic acid, including target RNA, T$_M$ values above about 45° C. in relatively short oligonucleotides (e.g., 10-15 bases); 3) the ability of the oligonucleotide to be actively or passively transported into mammalian cells; and 4) the ability of the oligonucleotide and oligonucleotide: RNA heteroduplex to resist RNAse and RNase H degradation, respectively.

The stability of the duplex formed between an oligomer and a target sequence is a function of the binding T$_M$ and the susceptibility of the duplex to cellular enzymatic cleavage. The T$_M$ of an oligomer with respect to complementary-sequence RNA may be measured by conventional methods, such as those described by Hames et al., Nucleic Acid Hybridization, IRL Press, 1985, pp. 107-108 or as described in Miyada C. G. and Wallace R. B., 1987, Oligomer Hybridization Techniques, Methods Enzymol. Vol. 154 pp. 94-107. In certain embodiments, antisense oligomers may have a binding T$_M$, with respect to a complementary-sequence RNA, of greater than body temperature and, in some embodiments greater than about 45° C. or 50° C. T$_M$'s in the range 60-80° C. or greater are also included. According to well-known principles, the T$_M$ of an oligomer, with respect to a complementary-based RNA hybrid, can be increased by increasing the ratio of C:G paired bases in the duplex, or by increasing the length (in base pairs) of the heteroduplex, or both. At the same time, for purposes of optimizing cellular uptake, it may be advantageous to limit the size of the oligomer. For this reason, compounds of the disclosure include compounds that show a high T$_M$ (45-50° C. or greater) at a length of 25 bases or less.

The length of an oligonucleotide may vary so long as it is capable of binding selectively to the intended location within the pre-mRNA molecule. The length of such sequences can be determined in accordance with selection procedures described herein. Generally, the oligonucleotide will be from about 8 nucleotides in length up to about 50 nucleotides in length. For example, the length of the oligonucleotide (z) can be 8-38, 8-25, 15-25, 17-21, or about 18. It will be appreciated however that any length of nucleotides within this range may be used in the methods described herein.

In some embodiments, the antisense oligonucleotides contain base modifications or substitutions. For example, certain nucleo-bases may be selected to increase the binding affinity of the antisense oligonucleotides described herein. These include 5-substituted pyrimidines, 6-azapyrimidines and N-2, N-6 and 0-6 substituted purines, including 2-aminopropyladenine, 5-propynyluracil, 5-propynylcytosine and 2,6-diaminopurine. 5-methylcytosine substitutions have been shown to increase nucleic acid duplex stability by 0.6-1.2° C., and may be incorporated into the antisense oligonucleotides described herein. In one embodiment, at least one pyrimidine base of the oligonucleotide comprises a 5-substituted pyrimidine base, wherein the pyrimidine base is selected from the group consisting of cytosine, thymine and uracil. In one embodiment, the 5-substituted pyrimidine base is 5-methylcytosine. In another embodiment, at least one purine base of the oligonucleotide comprises an N-2, N-6 substituted purine base. In one embodiment, the N-2, N-6 substituted purine base is 2, 6-diaminopurine.

Morpholino-based oligomers (including antisense oligomers) are detailed, for example, in U.S. Pat. Nos. 5,698,685; 5,217,866; 5,142,047; 5,034,506; 5,166,315; 5,185,444; 5,521,063; 5,506,337 and pending U.S. patent application Ser. Nos. 12/271,036; 12/271,040; and PCT Publication No. WO/2009/064471 and WO/2012/043730 and Summerton et al. 1997, Antisense and Nucleic Acid Drug Development, 7, 187-195, which are hereby incorporated by reference in their entirety.

Accordingly, in one aspect, provided herein is an oligonucleotide of Formula II:

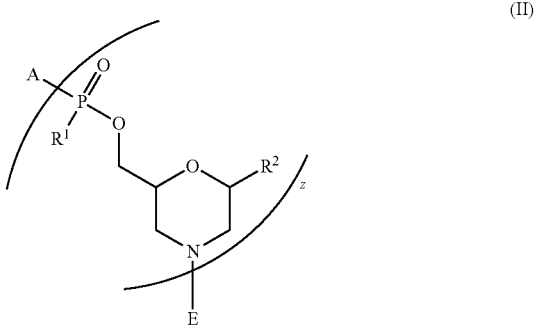

(II)

or a pharmaceutically acceptable salt thereof,
wherein
A is selected from the group consisting of OH, —NHCH$_2$C(O)NH$_2$, —N(C alkyl)CH$_2$C(O)NH$_2$, and

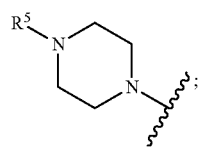

$R^5$ is —C(O)(O-alkyl)$_x$OH, wherein x is 3-10 and each alkyl group is independently at each occurrence —C$_{2-6}$-alkyl, or $R^5$ is selected from the group consisting of —C(O)C$_{1-6}$-alkyl, trityl, monomethoxytrityl, —C$_{1-6}$-alkyl-R$^6$, —C$_{1-6}$-heteroalkyl-R$^6$, -aryl-R$^6$, -heteroaryl-R$^6$, —C(O)O—C$_{1-6}$-alkyl-R$^6$, —C(O)O-aryl-R$^6$, and —C(O)O-heteroaryl-R$^6$;

$R^6$ is selected from the group consisting of OH, SH, and NH$_2$, or $R^6$ is O, S, or NH, covalently linked to a solid support;

each $R^1$ is independently OH or —NR$^3$R$^4$;

each $R^3$ and $R^4$ are independently at each occurrence —C$_{1-6}$-alkyl;

each $R^2$ is independently selected from the group consisting of H, a nucleobase, and a nucleobase functionalized with a chemical protecting-group, wherein the nucleobase independently at each occurrence comprises a C$_{3-6}$-heterocyclic ring selected from the group consisting of pyridine, pyrimidine, triazinane, purine, and deaza-purine;

z is 8-40;

E is selected from the group consisting of H, —C$_{1-6}$-alkyl, —C(O)C$_{1-6}$-alkyl, benzoyl, stearoyl, trityl, monomethoxytrityl, dimethoxytrityl, trimethoxytrityl,

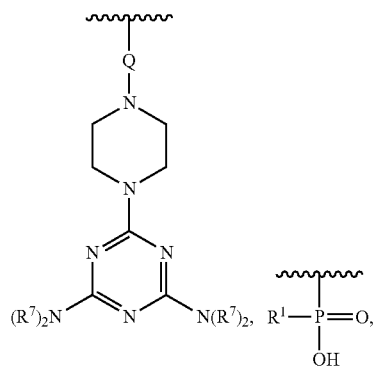

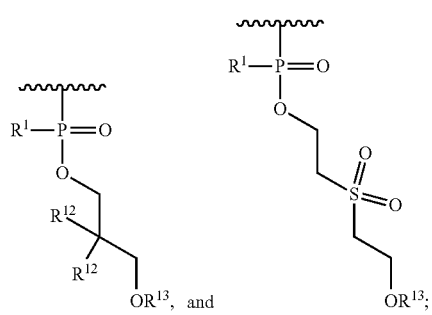

Q is —C(O)(CH$_2$)$_6$C(O)— or —C(O)(CH$_2$)$_2$S$_2$(CH$_2$)$_2$C(O)—;

$R^7$ is —(CH$_2$)$_2$OC(O)N(R$^8$)$_2$;

$R^8$ is —(CH$_2$)$_6$NHC(=NH)NH$_2$;

$R^{12}$ is —C(O)NHC$_{1-6}$-alkyl or —C(O)OC$_{1-6}$-alkyl; and $R^{13}$ is selected from the group consisting of trityl, monomethoxytrityl, dimethoxytrityl, and trimethoxytrityl.

In one embodiment of Formula II, A is

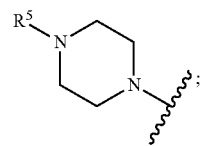

E is selected from the group consisting of H, —C(O)CH$_3$, benzoyl, and stearoyl;

$R^5$ is —C(O)(O-alkyl)$_x$-OH, wherein each alkyl group is independently at each occurrence —C$_{2-6}$-alkyl, trityl, and 4-methoxytrityl; and each $R^2$ is independently a nucleobase, wherein the nucleobase independently at each occurrence comprises a C$_{4-6}$-heterocyclic ring selected from the group consisting of pyridine, pyrimidine, purine, and deaza-purine.

In another embodiment of Formula II, $R^5$ is C(O)(O—CH$_2$CH$_2$)$_3$—OH; and each $R^2$ is independently a nucleobase, wherein the nucleobase independently at each occurrence comprises a pyrimidine or a purine.

In still another embodiment, the oligonucleotide of Formula II is an oligonucleotide of Formula IIa:

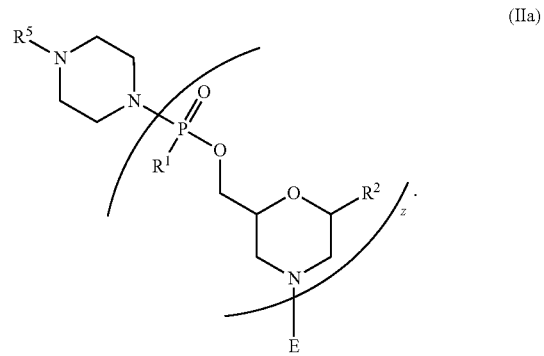

(IIa)

In an embodiment of Formula II and IIa, $R^2$ is independently at each occurrence adenine, 2,6-diaminopurine, guanine, hypoxanthine, cytosine, 5-methyl-cytosine, thymine, uracil, and hypoxanthine; and each $R^1$ is —N(CH$_3$)$_2$.

Provided in Table 1 are various embodiments of nucleotide moieties as described herein.

TABLE 1

Various embodiments of nucleotide moieties.

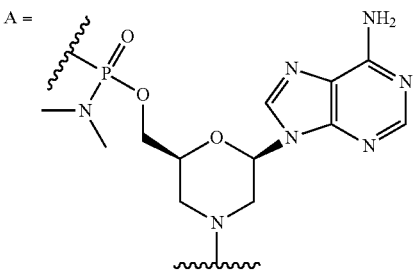

TABLE 1-continued

Various embodiments of nucleotide moieties.

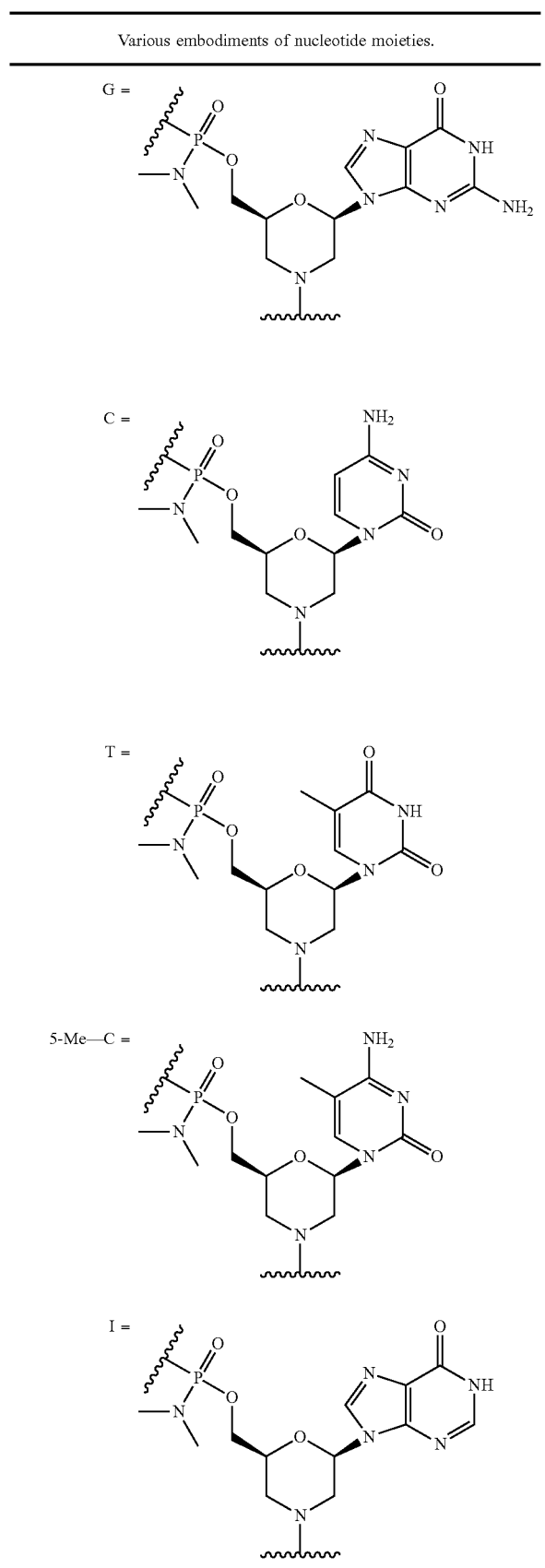

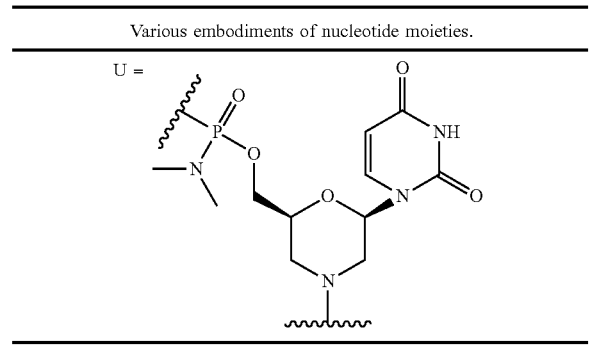

In some embodiments, the oligonucleotides described herein are unsolvated. In other embodiments, one or more of the oligonucleotides are in solvated form. As known in the art, the solvate can be any of pharmaceutically acceptable solvent, such as water, ethanol, and the like.

Although the oligonucleotides of Formulas II and IIa, are depicted in their neutral forms, in some embodiments, these oligonucleotides are used in a pharmaceutically acceptable salt form.

Peptides

The oligonucleotides provided herein include an oligonucleotide moiety conjugated to a CPP. In some embodiments, the CPP can be an arginine-rich peptide transport moiety effective to enhance transport of the compound into cells. The transport moiety is, in some embodiments, attached to a terminus of the oligomer. The peptides have the capability of inducing cell penetration within 30%, 40%, 50%, 60%, 70%, 80%, 90% or 100% of cells of a given cell culture population, including all integers in between, and allow macromolecular translocation within multiple tissues in vivo upon systemic administration. In one embodiment, the cell-penetrating peptide may be an arginine-rich peptide transporter. In various embodiments, a peptide-oligonucleotide-conjugate of the present disclosure may utilize glycine as the linker between the CPP and the antisense oligonucleotide.

The transport moieties as described above have been shown to greatly enhance cell entry of attached oligomers, relative to uptake of the oligomer in the absence of the attached transport moiety. Uptake may be enhanced at least ten fold, and, in some embodiments, twenty fold, relative to the unconjugated compound.

The use of arginine-rich peptide transporters (i.e., cell-penetrating peptides) are particularly useful in practicing the present disclosure. Certain peptide transporters have been shown to be highly effective at delivery of antisense compounds into primary cells including muscle cells. Furthermore, compared to other known peptide transporters such as Penetratin and the Tat peptide, the peptide transporters described herein, when conjugated to an antisense PMO, demonstrate an enhanced ability to alter splicing of several gene transcripts.

Thus, in one aspect, provided herein is a peptide of Formula III:

$$G-(J)_r-L \qquad (III)$$

or a pharmaceutically acceptable salt thereof,
wherein
G is selected from the group consisting of H, C(O)C$_{1-6}$-alkyl, benzoyl, and stearoyl;

each J is independently at each occurrence selected from an amino acid of the

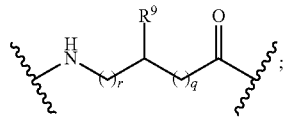

structure

- each $R^9$ is independently at each occurrence selected from the group consisting of H, an amino acid side-chain, and an amino acid side-chain functionalized with a chemical protecting-group;
- wherein two or more amino acid side-chain groups of $R^9$ independently at each occurrence comprise a thiol or a thiol functionalized with a chemical protecting-group;
- r and q are independently 0, 1, 2, 3, or 4;
- L is selected from the group consisting of —NH(CH$_2$)$_{1-6}$C(O)OH, —NH(CH$_2$)$_5$C(O)NH(CH$_2$)$_2$C(O)OH, and

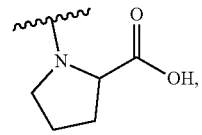 [SMILES: *N1CCCC1C(=O)O]

each of which may be covalently-linked to a solid support; and t is 4-9.

In one embodiment, two amino acid side-chain groups, wherein each of the two amino acid side-chain groups independently comprise a sulfur, together with the atoms to which they are attached, form the structure

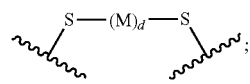

M is selected from the group consisting of

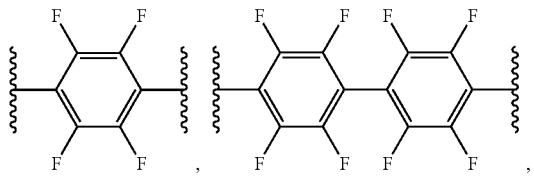

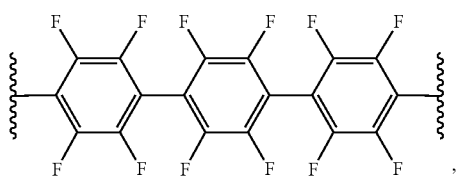

-continued

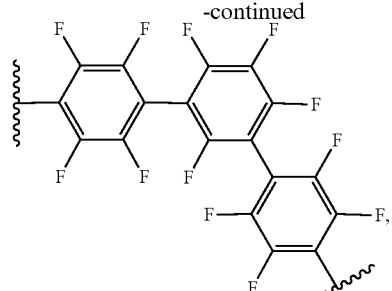

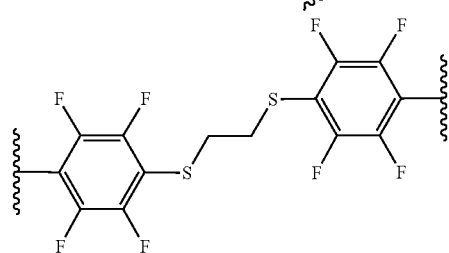

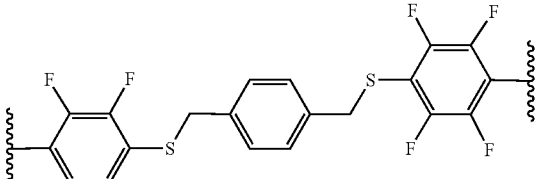

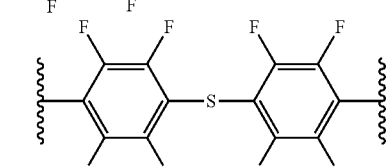

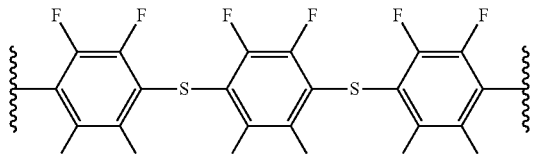

and d is 0 or 1.

In another embodiment, M is

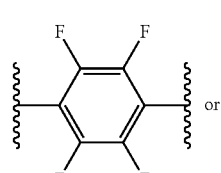

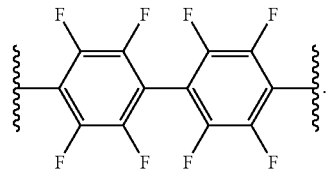

In yet another embodiment, two amino acid side-chain groups are independently at each occurrence cysteine or homocysteine amino acid side-chain groups.

In still another embodiment, each J is independently at each occurrence selected from an α-amino acid, a β²-amino acid, and a β³-amino acid.

In another embodiment, r and q are each 0.

In another embodiment, J is independently selected from cysteine and arginine.

In yet another embodiment, two J groups are cysteine.

In still another embodiment, L is selected from —NH(CH$_2$)$_{1-6}$C(O)OH and

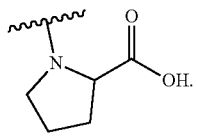 [SMILES: *N1CCCC1C(=O)O]

In another embodiment, L is

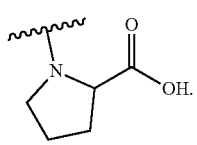 [SMILES: *N1CCCC1C(=O)O]

In yet another embodiment, L is NHCH$_2$C(O)OH.

In yet another embodiment, G is selected from the group consisting of H, C(O)CH$_3$, benzoyl, and stearoyl.

In still another embodiment, G is C(O)CH$_3$ or stearoyl.

In another embodiment, G is C(O)CH$_3$.

In yet another embodiment, G is covalently linked to the amino-terminus of J. In a further embodiment, L is covalently linked by an amide bond to the carboxy-terminus of J.

In another embodiment, d is 0.

In yet another embodiment, d is 1.

Provided in Table 2 are representative peptides as described herein.

TABLE 2

| Exemplary Peptides | | |
|---|---|---|
| Structure | Compound | SEQ ID NO |
| Ac-Cys-R$_3$-Cys-R$_2$-Gly-OH | 1AC<br>1AD<br>1AE<br>1BC<br>1BD<br>1BE | 1 |
| Ac-Cys-R$_3$-Cys-R$_2$-Gly-OH | 2AC<br>2AD<br>2AE<br>2BC<br>2BD<br>2BE | 2 |
| Ac-Cys-R$_3$-Cys-R$_2$-Gly-OH | 3AC<br>3AD<br>3AE<br>3BC<br>3BD<br>3BE | 3 |
| Ac-Cys-R$_6$-Cys-Gly-OH | 4AC<br>4AD<br>4AE<br>4BC<br>4BD<br>4BE | 4 |

TABLE 2-continued

| Exemplary Peptides | | |
|---|---|---|
| Structure | Compound | SEQ ID NO |
| Ac-Cys-R$_5$-Cys-Gly-OH | 5AC<br>5AD<br>5AE<br>5BC<br>5BD<br>5BE | 5 |
| Ac-Cys-R$_4$-Cys-Gly-OH | 6AC<br>6AD<br>6AE<br>6BC<br>6BD<br>6BE | 6 |
| Ac-Cys-R$_3$-Cys-Gly-OH | 7AC<br>7AD<br>7AE<br>7BC<br>7BD<br>7BE | 7 |
| Ac-Cys-R$_2$-Cys-Gly-OH | 8AC<br>8AD<br>8AE<br>8BC<br>8BD<br>8BE | 8 |

Gly = glycinyl or Gly-P3P        R = Arg
 (A)         (B)

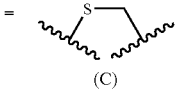
(C)

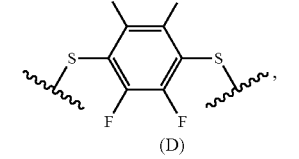
(D)

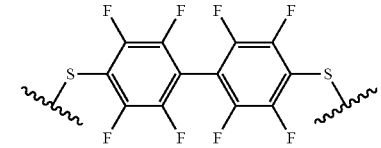 [SMILES: *Sc1c(F)c(F)c(-c2c(F)c(F)c(S*)c(F)c2F)c(F)c1F]
(E)

In some embodiments, the peptides described herein are unsolvated. In other embodiments, one or more of the peptides are in solvated form. As known in the art, the solvate can be any of pharmaceutically acceptable solvent, such as water, ethanol, and the like.

Although the peptides of Formula III, are depicted in their neutral forms, in some embodiments, these oligonucleotides are used in a pharmaceutically acceptable salt form.

General Synthetic Schemes
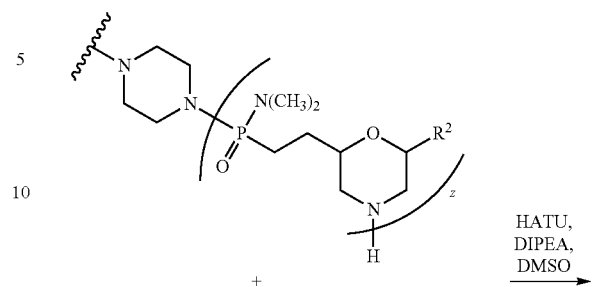
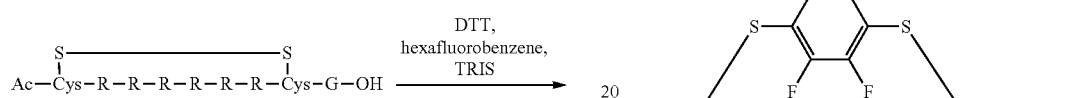
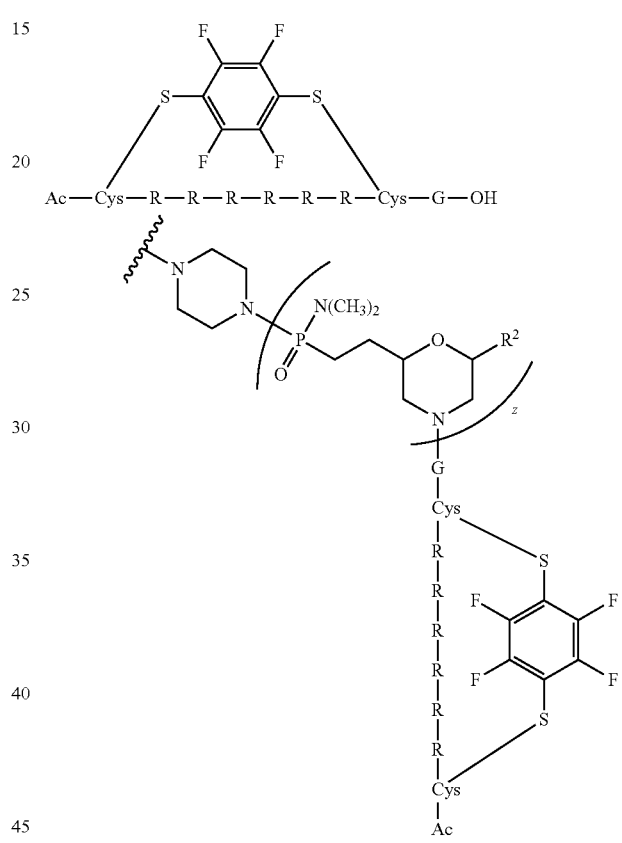
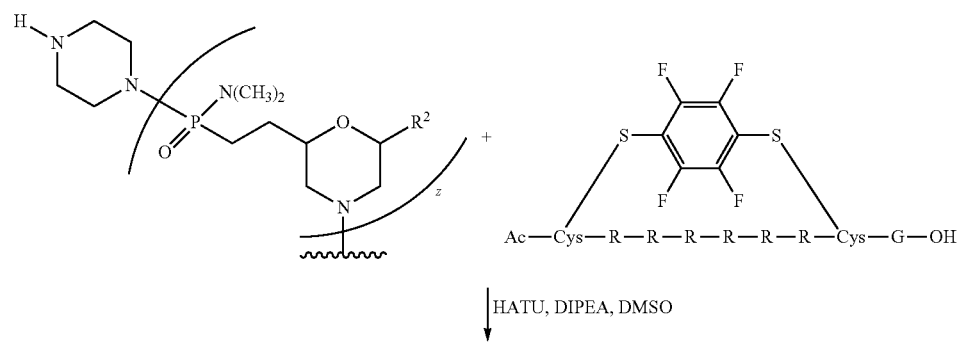

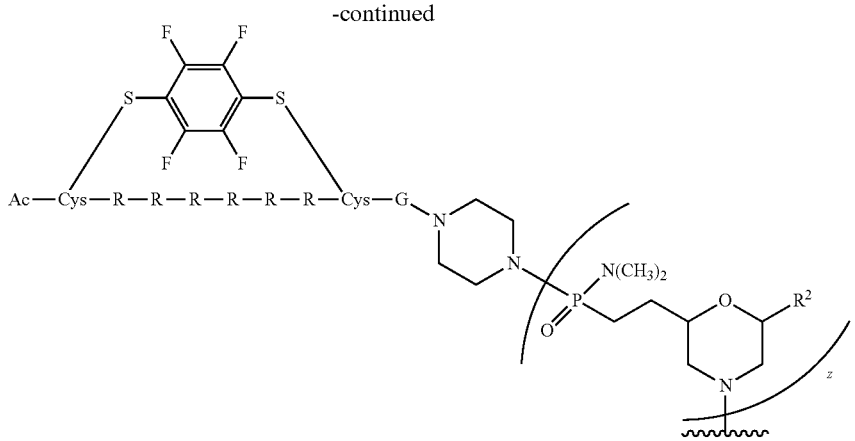
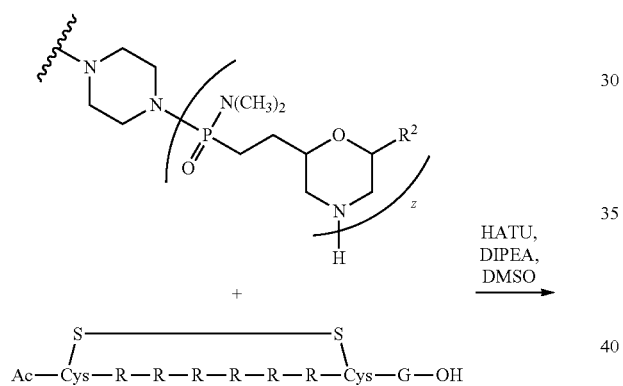
The process of Scheme IIa is applicable to conjugation of the peptide to the 5' end of the PMO under similar conditions (see Scheme Ic).
Scheme IIa: Conjugation of disulfide peptide to 3' end of PMO
Scheme IIb: Stapling of peptide-PMO-conjugate
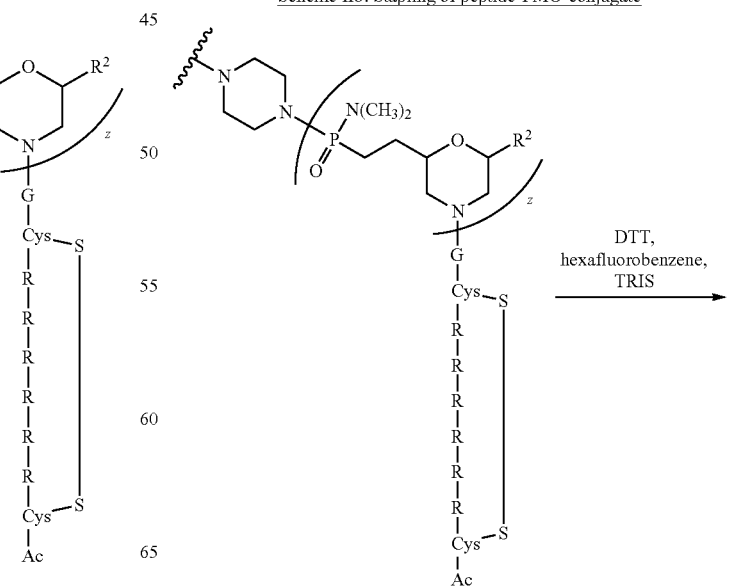

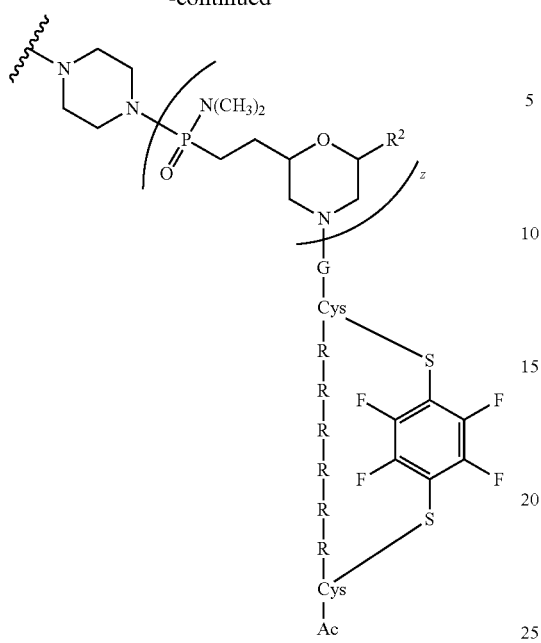
The process of Scheme IIb is applicable to conjugation of the peptide to the 5' end of the PMO under similar conditions.
Scheme IIIa: One-pot conjugation and stapling with peptide and PMO
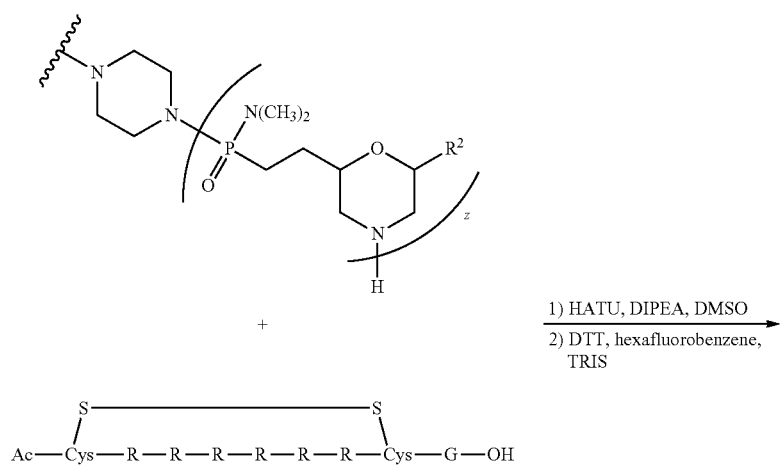

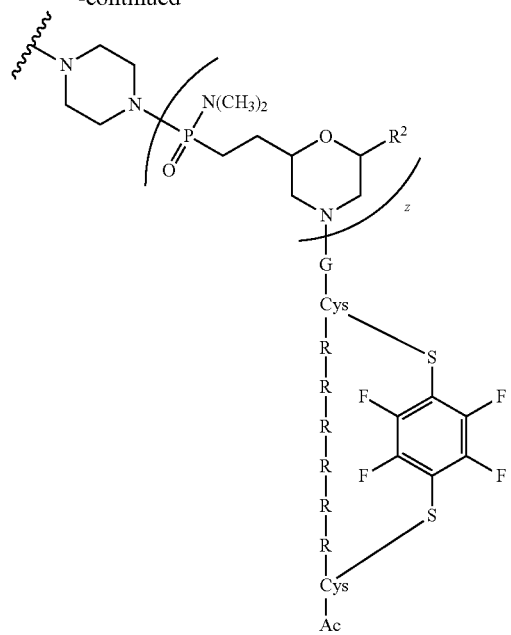

Scheme IIIb: One-pot conjugation and stapling with peptide and PMO

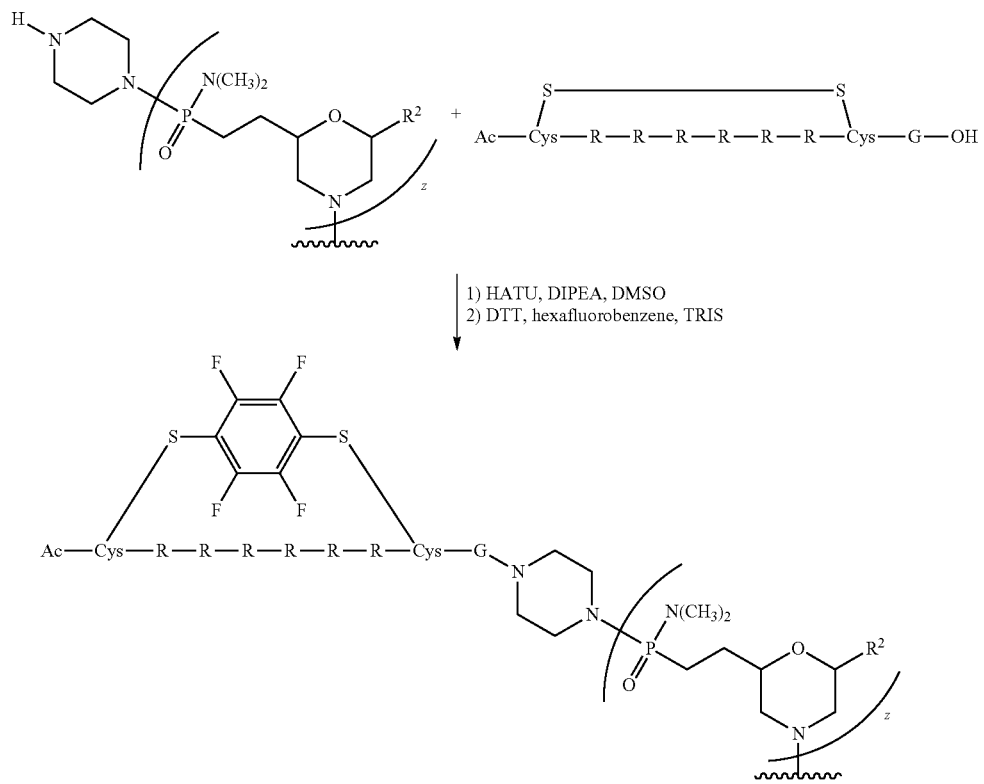

Methods

Provided herein are methods of treating a muscle disease, a viral infection, or a bacterial infection in a subject in need thereof, comprising administering to the subject a peptide-oligonucleotide-conjugate of Formulae I, Ia, Ib, Ic, Id, Ie, or V.

Accordingly, in one aspect, provided herein is a method of treating a muscle disease, a viral infection, or a bacterial infection in a subject in need thereof, comprising administering to the subject a peptide-oligonucleotide-conjugate of the present disclosure.

In one embodiment, the muscle disease is Duchenne Muscular Dystrophy.

In another embodiment, the viral infection is caused by a virus selected from the group consisting of marburg virus, ebola virus, influenza virus, and dengue virus.

In another embodiment, the bacterial infection is caused by *Mycobacterium tuberculosis*.

The subject considered herein is typically a human. However, the subject can be any mammal for which treatment is desired. Thus, the methods described herein can be applied to both human and veterinary applications.

Administration/Dose

The formulation of therapeutic compositions and their subsequent administration (dosing) is within the skill of those in the art. Dosing is dependent on severity and responsiveness of the disease state to be treated, with the course of treatment lasting from several days to several months, or until a sufficient diminution of the disease state is achieved. Optimal dosing schedules can be calculated from measurements of drug accumulation in the body of the patient.

Persons of ordinary skill can easily determine optimum dosages, dosing methodologies and repetition rates. Optimum dosages may vary depending on the relative potency of individual oligomers, and can generally be estimated based on $EC_{50}$s found to be effective in in vitro and in vivo animal models. In general, dosage is from 0.01 µg to 100 g/kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligomer is administered in maintenance doses, ranging from 0.01 µg to 100 g/kg of body weight, once or more daily, to once every 20 years.

In some embodiments, the oligonucleotide (an oligonucleotide of Formulae II or IIa) is administered alone.

In some embodiments, the oligonucleotide is administered in a therapeutically effective amount or dosage. A "therapeutically effective amount" is an amount of an oligonucleotide of Formula II or IIa that, when administered to a patient by itself, effectively treats a muscle disease, a viral infection, or a bacterial infection. An amount that proves to be a "therapeutically effective amount" in a given instance, for a particular subject, may not be effective for 100% of subjects similarly treated for the disease or condition under consideration, even though such dosage is deemed a "therapeutically effective amount" by skilled practitioners. The amount of the oligonucleotide that corresponds to a therapeutically effective amount is strongly dependent on the type of disease, stage of the disease, the age of the patient being treated, and other facts.

In different embodiments, depending on the oligonucleotide of Formulae II or IIa and the effective amounts used, the oligonucleotides can modulate the expression of a gene involved in a muscle disease, a viral infection, or a bacterial infection.

While the amounts of an oligonucleotide of Formulae II or IIa should result in the effective treatment of a muscle disease, a viral infection, or a bacterial infection, the amounts, are preferably not excessively toxic to the patient (i.e., the amounts are preferably within toxicity limits as established by medical guidelines). In some embodiments, either to prevent excessive toxicity or provide a more efficacious treatment, or both, of a muscle disease, a viral infection, or a bacterial infection, a limitation on the total administered dosage is provided. Typically, the amounts considered herein are per day; however, half-day and two-day or three-day cycles also are considered herein.

Different dosage regimens may be used to treat a muscle disease, a viral infection, or a bacterial infection. In some embodiments, a daily dosage, such as any of the exemplary dosages described above, is administered once, twice, three times, or four times a day for three, four, five, six, seven, eight, nine, or ten days. Depending on the stage and severity of the disease being treated, a shorter treatment time (e.g., up to five days) may be employed along with a high dosage, or a longer treatment time (e.g., ten or more days, or weeks, or a month, or longer) may be employed along with a low dosage. In some embodiments, a once- or twice-daily dosage is administered every other day.

Oligonucleotides of Formula II and IIa, or their pharmaceutically acceptable salts or solvate forms, in pure form or in an appropriate pharmaceutical composition, can be administered via any of the accepted modes of administration or agents known in the art. The oligonucleotides can be administered, for example, orally, nasally, parenterally (intravenous, intramuscular, or subcutaneous), topically, transdermally, intravaginally, intravesically, intracistemally, or rectally. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, for example, in unit dosage forms suitable for simple administration of precise dosages. A particular route of administration is oral, particularly one in which a convenient daily dosage regimen can be adjusted according to the degree of severity of the disease to be treated.

Auxiliary and adjuvant agents may include, for example, preserving, wetting, suspending, sweetening, flavoring, perfuming, emulsifying, and dispensing agents. Prevention of the action of microorganisms is generally provided by various antibacterial and antifungal agents, such as, parabens, chlorobutanol, phenol, sorbic acid, and the like. Isotonic agents, such as sugars, sodium chloride, and the like, may also be included. Prolonged absorption of an injectable pharmaceutical form can be brought about by the use of agents delaying absorption, for example, aluminum monostearate and gelatin. The auxiliary agents also can include wetting agents, emulsifying agents, pH buffering agents, and antioxidants, such as, for example, citric acid, sorbitan monolaurate, triethanolamine oleate, butylated hydroxytoluene, and the like.

Solid dosage forms can be prepared with coatings and shells, such as enteric coatings and others well-known in the art. They can contain pacifying agents and can be of such composition that they release the active oligonucleotide or oligonucleotides in a certain part of the intestinal tract in a delayed manner. Examples of embedded compositions that can be used are polymeric substances and waxes. The active oligonucleotides also can be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the HDAC inhibitors or retinoic acid described herein, or a pharmaceutically acceptable salt thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethyl formamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Generally, depending on the intended mode of administration, the pharmaceutically acceptable compositions will contain about 1% to about 99% by weight of the oligonucleotides described herein, or a pharmaceutically acceptable salt thereof, and 99% to 1% by weight of a pharmaceutically acceptable excipient. In one example, the composition will be between about 5% and about 75% by weight of a oligonucleotide described herein, or a pharmaceutically acceptable salt thereof, with the rest being suitable pharmaceutical excipients.

Actual methods of preparing such dosage forms are known, or will be apparent, to those skilled in this art. Reference is made, for example, to Remington's Pharmaceutical Sciences, 18th Ed. (Mack Publishing Company, Easton, Pa., 1990).

Kits

In other embodiments, kits are provided. Kits according to the disclosure include package(s) comprising oligonucleotides, peptides, peptide-oligonucleotide-conjugates, or compositions of the disclosure. In some embodiments, kits comprise a peptide-oligonucleotide-conjugate according to Formulae I, Ia, Ib, Ic, Id, Ie, or V, or a pharmaceutically acceptable salt thereof. In other embodiments, kits comprise an oligonucleotide according to Formulae II or IIa, or a pharmaceutically acceptable salt thereof. In still other embodiments, kits comprise a peptide according to Formula III, or a pharmaceutically acceptable salt thereof.

The phrase "package" means any vessel containing oligonucleotides or compositions presented herein. In some embodiments, the package can be a box or wrapping. Packaging materials for use in packaging pharmaceutical products are well-known to those of skill in the art. Examples of pharmaceutical packaging materials include, but are not limited to, bottles, tubes, inhalers, pumps, bags, vials, containers, syringes, bottles, and any packaging material suitable for a selected formulation and intended mode of administration and treatment.

The kit can also contain items that are not contained within the package, but are attached to the outside of the package, for example, pipettes.

Kits can further contain instructions for administering oligonucleotides or compositions of the disclosure to a patient. Kits also can comprise instructions for approved uses of oligonucleotides herein by regulatory agencies, such as the United States Food and Drug Administration. Kits can also contain labeling or product inserts for the oligonucleotides. The package(s) or any product insert(s), or both, may themselves be approved by regulatory agencies. The kits can include oligonucleotides in the solid phase or in a liquid phase (such as buffers provided) in a package. The kits can also include buffers for preparing solutions for conducting the methods, and pipettes for transferring liquids from one container to another.

Examples

Examples have been set forth below for the purpose of illustration and to describe certain specific embodiments of the disclosure. However, the scope of the claims is not to be in any way limited by the examples set forth herein. Various changes and modifications to the disclosed embodiments will be apparent to those skilled in the art and such changes and modifications including, without limitation, those relating to the chemical structures, substituents, derivatives, formulations or methods of the disclosure may be made without departing from the spirit of the disclosure and the scope of the appended claims. Definitions of the variables in the structures in the schemes herein are commensurate with those of corresponding positions in the formulae presented herein.

Example 1: A Protocol for Peptide Stapling With Hexafluorobenzene

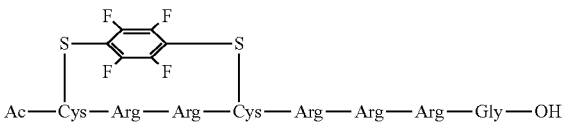

To the cyclic disulfide peptide Ac-CRRRCRRRG-OH (74.8 mg, 38.5 (SEQ ID NO:3) in a glass vial is added a solution of TRIS base (8 mL, 50 mM in DMF) and hexafluorobenzene (111 µL, 962 µmol). To this solution, TCEP solution in $H_2O$ (136 µL, 0.71 M, pH=8) is added to reduce the disulfide bond and initiate reaction. The reaction mixture is stirred at room temperature for 7 hours and monitored by LC-MS. The resulting mixture is diluted with 40 mL of 0.1% TFA in water, centrifuged, filtered, and subjected to purification by HPLC. Fractions containing peptide product (analyzed by LC-MS) are combined and lyophilized to give the desired perfluoroaryl peptide (19.9 mg, 8.9 µmol, 23% yield).

Example 2: A Protocol for Peptide Stapling With Decafluorobiphenyl

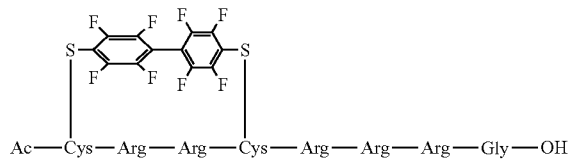

In a glass vial, the cyclic disulfide peptide Ac-CRRRCRRRG-OH (74.5 mg, 38.4 (SEQ ID NO:3) and decafluorobiphenyl (25.6 mg, 76.7 µmol are dissolved in a solution of TRIS base in DMF (8 mL, 50 mM). To this solution is added a TCEP solution in $H_2O$ (135 µL, 0.71 M, pH~8) in order to reduce the disulfide bond and initiate reaction. The reaction mixture is stirred at room temperature for 7 hours and monitored by LC-MS. The resulting mixture is diluted with TFA in water (40 mL of 0.1%), centrifuged, filtered, and subjected to purification by HPLC. Fractions containing peptide product are analyzed by LC-MS, combined, and lyophilized to give the final perfluoroaryl peptide (20 mg, 8.9 µmol, 23% yield).

Example 3: A Protocol for Peptide Conjugation

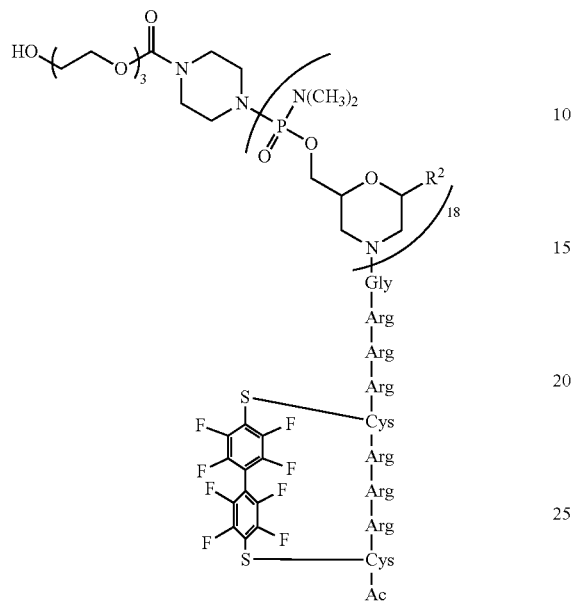

(PPMO 1)

To a mixture of the PMO (nucleobase sequence (R²) is: GCT ATT ACC TTA ACC CAG (SEQ ID NO:9); 10.7 mg, 1.72 µmol) and the decafluorobiphenyl peptide Ac-CRRR-CRRRG-OH (5.9 mg, 2.64 umol) in a plastic Eppendorf tube is added DMSO (0.4 mL), HATU in DMSO (6.6 µL, 2.64 µmol, 0.4 M), and DIPEA (2.3 µL, 13.2 µmol). The contents of the tube are mixed and allowed to stand at room temperature for 2 hours. The resulting mixture is diluted with water (8 mL) and subjected sequentially to weak cation exchange (CM Sepharose) and solid phase extraction (Amberchrom CG 300M). The resulting product is analyzed by LC-MS and MALDI-TOF MS, and lyophilized to give the PMO-peptide conjugate (9.8 mg, 1.26 µmol, 73% yield).

Example 4: A Protocol for Single Pot Conjugation of PMO with a Cyclic Disulfide Peptide Followed by Peptide Stapling

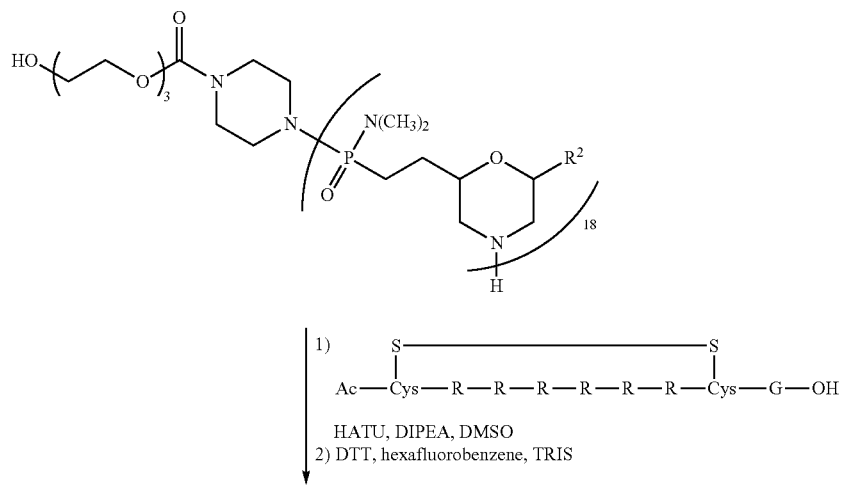

-continued

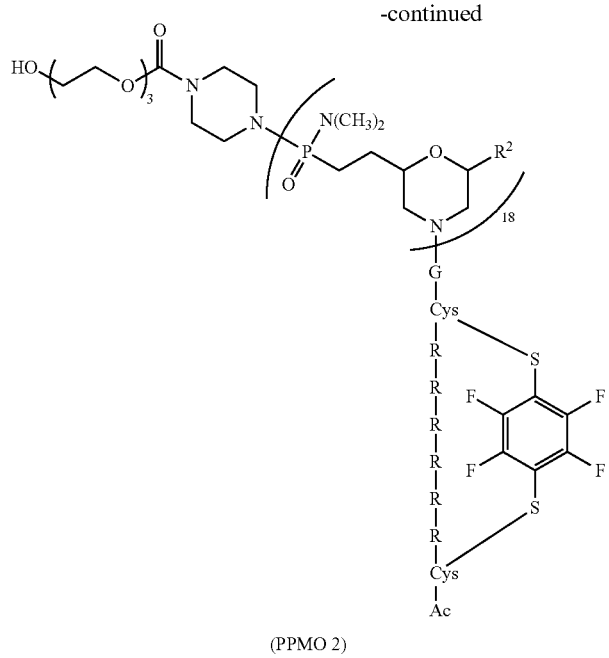

(PPMO 2)

To a solution of PMO (85 mg, 0.01 mmol, 1 eq; nucleobase sequence ($R^2$): GCT ATT ACC TTA ACC CAG (SEQ ID NO:9)), the peptide (Ac-Cys-Arg-Arg-Arg-Arg-Arg-Arg-Cys-Gly-OH or Ac-Cys-Arg-Arg-Arg-Cys-Arg-Arg-Arg-Gly-OH, 37 mg, each with a disulfide bridge, 2 eq) and HATU (8 mg, 2 eq) in DMSO (2 mL) is added diisopropylethylamine (9 μL, 5 eq). The reaction is stirred at room temperature for 5 hours. After adding 50 mM of dithiothreitol (DTT) in DMSO solution (1 mL, 5 eq), 50 mM of TRIS in DMSO solution (1 mL, 5 eq), followed by hexafluorobenzene (60 μL, 25 eq), the reaction solution is stirred for another 5 hours. The desired product is obtained by weak cation exchange chromatography (CM-Sepharose) followed by solid phase extraction (Amberchrome CG300M) to desalt, and finally lyophilization. MALDI/TOF mass spectrum (m/z): calcd: 9975; found: 9976 (M+H).

Example 5: HeLa Cell Assay

The graph in FIG. 1 (see also Table 3) shows on the y axis "mean fluorescence intensity" of e-GFP protein green fluorescence emission as read from each individual cell by an Accuri C6 flow cytometer and summed by the processing software. The height of the green fluorescent signal bars indicate different intensities based on the level of exon skipping that occurs in the nucleus of HeLa-654 cells, whether the cells are treated or untreated with test compounds. The signal intensity or size of the bar also corresponds to the effectiveness of cellular uptake (that is, delivery into the cell). The x axis shows test compounds tested with a variety of different treatment regimens. The various treatment regimens include continuous treatment of HeLa-654 cells over time or pulse-chase treatments where a test compound is incubated with cells and then after a period of time (3 hours) is washed away from the cells and fresh, test compound-free media is added.

Results: The baseline activity of unconjugated PMO and untreated cells is shown. The peptide/PMO (PPMO) conjugates of the present disclosure all show greater cellular uptake than: 1) unconjugated PMO, and 2) untreated cells (which reveal the green fluorescent background signal). This difference in fluorescence intensity between the peptide/PMO conjugates of the present invention and the background or unconjugated-PMO indicates significant pharmacological activity of the stapled peptide/PMO conjugates.

In each case, the PMO is of the following structure:

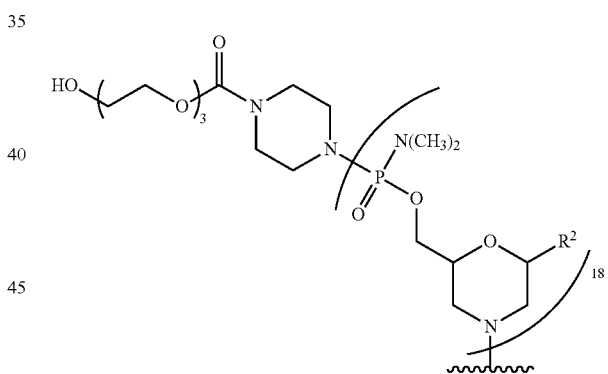

where the nucleobase sequence (comprising each occurrence of $R^2$ being independently selected from a nucleobase selected from A, G, C or T) is: GCT ATT ACC TTA ACC CAG (SEQ ID NO:9).

TABLE 3

| Cellular Delivery of peptide-oligonucleotide-conjugates (FIG. 1) | |
|---|---|
| | Mean FL1-H |
| No Treatment | 36,594.96 |
| PMO | 43,039.34 |
| (i, i + 4) Hexa – PPMO 3 | 123,401.08 |
| (i, i + 4) Deca – PPMO 1 | 87,951.78 |
| (i, i + 7) Deca – PPMO 4 | 137,184.08 |

PPMO 3 refers to the following structure:

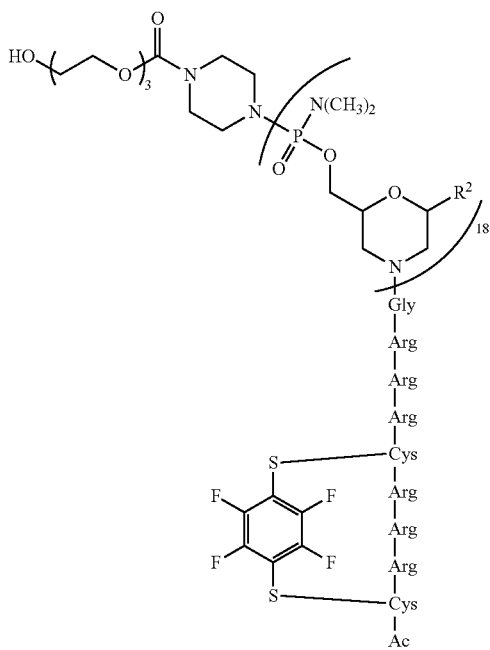

where the nucleobase sequence (comprising each occurrence of $R^2$ being independently selected from a nucleobase selected from A, G, C or T) is: GCT ATT ACC TTA ACC CAG (SEQ ID NO:9).

PPMO 4 refers to the following structure:

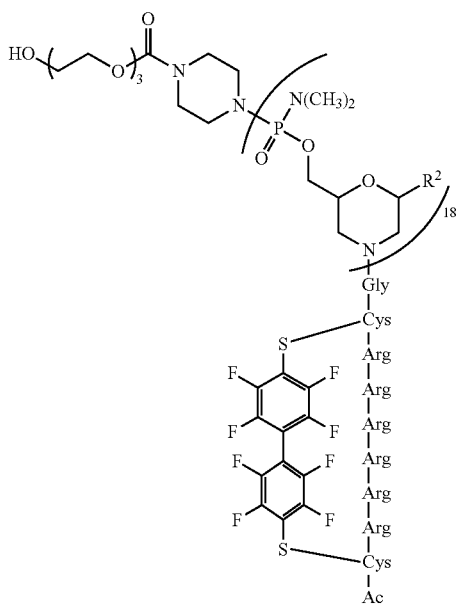

where the nucleobase sequence (comprising each occurrence of $R^2$ being independently selected from a nucleobase selected from A, G, C or T) is: GCT ATT ACC TTA ACC CAG (SEQ ID NO:9).

Example 6: In Vivo Protein and Exon Skipping 14 groups of 5 mice each (70 mice total; 65 mdx, 5 wt) were treated as described below, and then analyzed for dystrophin protein and exon skipping.

Mice were given a 200 µLt bolus of compound via tail vein injection, and were then euthanized 8 days post-injection. Quadriceps, diaphragm, heart and brain tissues (individual structures) were collected, lysed, and analyzed for dystrophin protein using traditional western blot, and analyzed for exon skipping using RT-PCR and Caliper (see FIGS. 2-7).

Figure 7A:
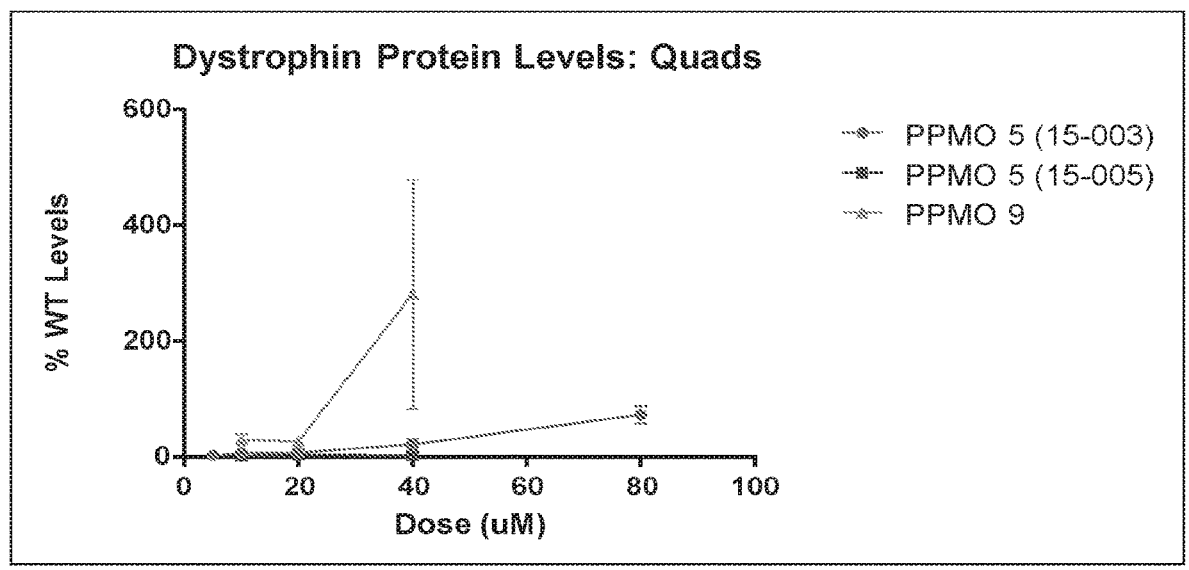
FIG. 7A shows the quantification of dystrophin levels in mouse quadriceps tissue following administration of PPMO 5 (two replications of same assay) or PPMO 9.
Figure 7B:
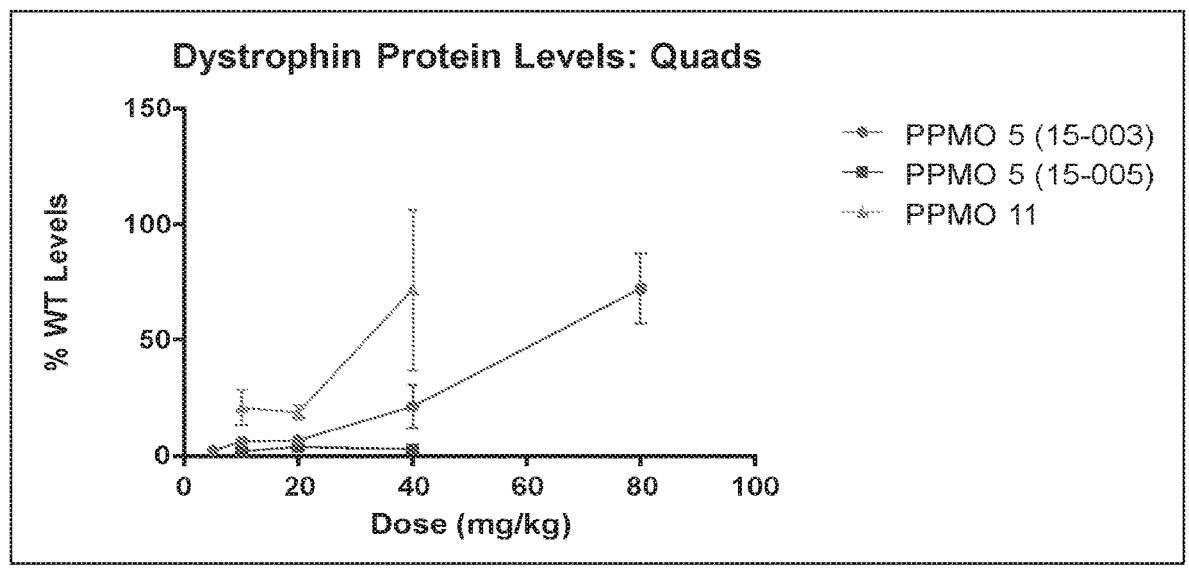
FIG. 7B shows the quantification of dystrophin levels in mouse quadriceps tissue following administration of PPMO 5 (two replications of same assay) or PPMO 11.
Figure 7C:
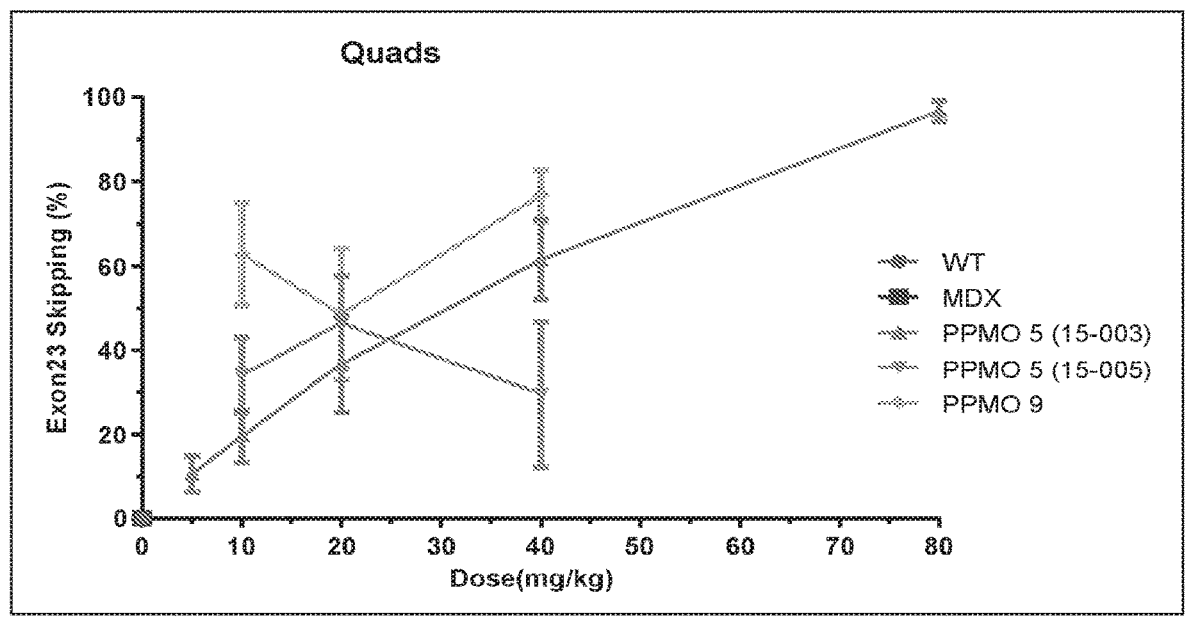
FIG. 7C shows the quantification of Exon23 Skipping (%) in mouse quadriceps tissue following administration of PPMO 5 (two replications of same assay) or PPMO 9; wildtype and mdx mice were used as controls.
Figure 7D:
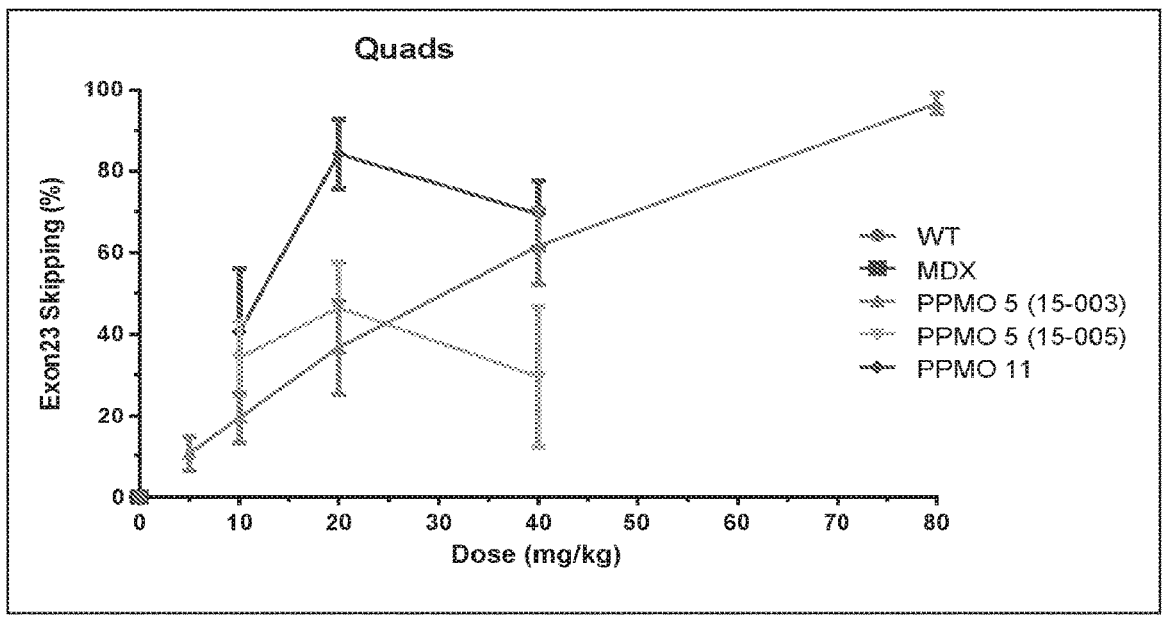
FIG. 7D shows the quantification of Exon23 Skipping (%) in mouse quadriceps tissue following administration of PPMO 5 (two replications of same assay) or PPMO 11; wildtype and mdx mice were used as controls.

Embodiments of compounds of the present disclosure were tested for their ability in vivo to effect mRNA and protein remodeling. In the event, these tested compounds showed activity in the mdx mouse, causing substantial increases in exon 23 skipping and dystrophin protein expression as shown by RT-PCR and western blot, respectively. This activity is especially pronounced when measured against the background of negative control experiments where the mdx mouse was dosed with saline, a condition which produced essentially zero exon 23 skipping and dystrophin (FIGS. 4D, 5C, 5D, 6D, 7C, and 7D). When compared to the two positive controls, wild type mice and mdx mice dosed with a known active compound Ac-R6-Gly-M23D(+7-18) (PPMO 5), the tested compounds were clearly active. In some cases the activity was greater than control; for example, PPMO 11 (Table 4) produced much larger responses in exon skipping and dystrophin expression at lower doses than the positive control compound (FIGS. 7B and 7D). Thus the tested compounds meet the condition of eliciting positive pharmacological responses in the context of a seven day in vivo screening assay.

Embodiments of compounds (PPMOs) of the present disclosure used in these studies have a structure according to Formula V:

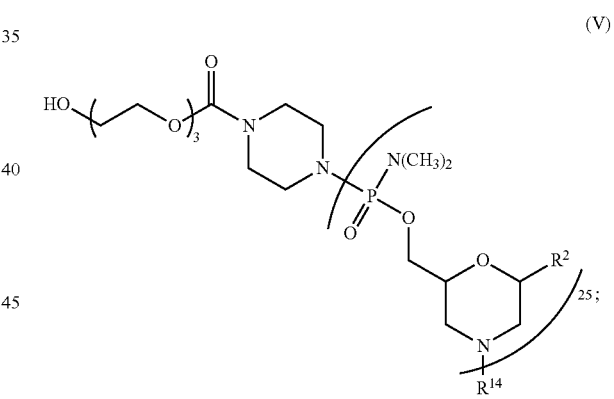

wherein
the nucleobase sequence (comprising each occurrence of $R^2$ being independently selected from a nucleobase selected from A, G, C or T) is: 5'-GGC CAA ACC TCG GCT TAC CTG AAA T-3' (SEQ ID NO:14); and
$R^{14}$ is as defined in Table 4.

Compounds of Table 4 were prepared according to Examples 1~4 above.

TABLE 4

| Compound of Formula (V) | $R^{14}$ (* see Table 2) |
|---|---|
| PPMO 5 | Ac-R$_6$-Gly-(SEQ ID NO: 15) |
| PPMO 6 | 4AD* |
| PPMO 7 | 3AD* |

TABLE 4-continued

| Compound of Formula (V) | R$^{14}$ (* see Table 2) |
| --- | --- |
| PPMO 8 | 4AC* |
| PPMO 9 | 3AC* |
| PPMO 10 | 4AE* |
| PPMO 11 | 3AE* |

Dystrophin Western Blot Protocol:
1. Tissue was removed from −80° C. and manually chopped into small pieces, 400-800 µL of RIPA lysis buffer added depending on the tissue type.
   a. TA: 400 µL, QC: 800 µL, Heart: 400 µL
   b. Lysis buffer: RIPA buffer (Pierce, cat #89901) and proteinase inhibitor cocktail (Roche, cat #04693124001)
2. About ten 2.0 mm Zirconia Beads (Biospec, Cat #11079124zx) were added to the tube, and the tissues were lysed with MagNA Lyser (Roche) as follows:
   a. 5,000 rpm, 30-40 s, cooled for 2 min on ice. The cycles were repeated until the tissues were completely lysed.
   Alternatively to Zirconia Beads, metal beads (3-5 beads) were used, 3000 rpm, 20 s per cycle (cooled on ice between cycles for 3-5 minutes or until cold to the touch).
3. Following lysis, samples were centrifuged at 12,000 rpm for 10 min and the supernatant transferred to a fresh tube, and a BCA assay was performed to quantify protein levels.
4. Gel Electrophoresis:
   a. Marker was loaded (Invitrogen, cat #P/NLC5699) and 100 µg of protein was loaded per lane, and the samples were run on a 3-8% Tris Acetate gel (midi gel, Biorad, cat #345-0130) at 50 v, 5 min; 150 v, 1 hr and then 200 v for 1.5 hr (71 kD marker was at the bottom of the gel).
5. Transfer: Overnight wet transfer (16-18 hr) at 4° C., constant 100 mA (~25 v), 0.45 µm PVDF membrane (Biorad, cat #1620261).
6. The membrane was washed in TBST for 5 min, and blocked in 10% milk (Biorad, cat #170-6404) in TBST for 1-2 hr at room temperature (RT).
7. The PVDF membrane was rinsed with TBST 2-3 times, and then incubated with primary antibody in 5% BSA in PBS overnight at 4° C.
   a. Dys2 (Novocastra, Leica Biosystem, cat #NCL-DYS2) 1:30
   b. Dys1 (Novocastra, Leica Biosystem, cat #NCL-DYS1) 1:1000
   c. Mandys8 (Sigma, cat #D8168) 1:3000.
8. The membrane was washed with TBST (10 min for each time, 3 times), HRP conjugated goat anti-mouse (BioRad, cat #1706516, 1:10000) secondary antibody was added, incubated for 1 hr at RT, and then washed with TBST (10 min for each time, 3 times).
9. Clarity Western ECL substrate (Biorad) was added and incubated for 5 min at RT, and then visualized with Chemidoc touch imaging system.
10. The membrane was stripped with 0.2N NaOH for 7 min, then equilibrated in TBST for at least 10 min. The blot was blocked with 10% milk in TBST for 1 hr at RT.
11. α-actinin2 antibody (Abcam, rabbit, cat #ab68168, 1:15000) was added and incubated for 1 hr at RT.
12. Washed with TBST (10 min for each time, 3 times) and then incubated with the HRP conjugated goat anti-rabbit (BioRad, cat #1706515, 1:10000) secondary antibody for 1 hr at RT.
13. The membrane was washed with TBST extensively and then imaged as described above.

RNA Extration Method for Mouse Tissues:
1. Whole tissue pieces (half quadricep, half heart, whole TA . . . .) were homogenized with MagNA Lyser and metal beads at 3000 rpm, 20 per cycle until the tissues were lysed well (samples were cooled on ice in between cycles for 3-5 minutes or until cold to the touch). 50-100 µL of whole lysate were transferred into a new 96 well plate and mixed with the same volume of RA4 buffer (from GE RNAspin Kit), the lysate mixture was then loaded into the 96 well RNAspin plate for the remaining purification steps. Unused lysate (in RA1 buffer) was stored at −80° C. for one year according to the kit protocol.
2. Samples were centrifuged for 2 min at 5200 g. 500 µL RA3 was added to each well of RNA binding plate, and the plate was centrifuged for 2 min at 5200 g. The flow through was discarded.
3. The membrane was washed by adding 500 µL RA2 to each well of RNA binding plate, and centrifuged for 2 min at 5200 g.
4. 800 µL RA3 was added to each well and centrifuged for 2 min at 5200 g.
5. 500 µL RA4 was added to each well and centrifuged for 10 min at 5200 g.
6. The samples were eluted into a PCR plate (with conical wells) by pipetting 50 RNase free water into the bottom of each well, ensuring the membrane was completely wetted. Samples were incubated for 2 min at RT and centrifuged at 5200 g for 3 min. If there was any liquid remaining in the well, the samples were incubated for an additional 2 minutes at RT and centrifuged again at 5200 g for 3 min.
7. The RNA concentration was then measured on a Nanodrop 2000 spectrophotometer.

RT-PCR Protocol:
Primers used for RT-PCR were as follows: Dystrophin Outer Forward: 5'-CAATGTTTCTGGATGCA-GACTTTGTGG-3' (SEQ ID NO:10); Dystrophin Outer Reverse: 5'-GTTCAGCTTCACTCTTTATCTTCTGCC-3' (SEQ ID NO:11); Dystrophin Inner Forward: 5'-CA-CATCTTTGATGGTGTGAGG-3' (SEQ ID NO:12); and Dystrophin Inner Reverse: 5'-CAACTTCAGCCATCCAT-TTCTG-3' (SEQ ID NO:13).
25 µL reactions (Table 5) were prepared for RT-PCR and primary amplification. RT-PCR program was performed according to Table 6.

TABLE 5

| RT-PCR Reaction Mixture | |
| --- | --- |
| 2 × Reaction mix | 12.5 µL |
| Dys inner Forward Primer (10 µM) | 0.75 µL |
| Dys inner Reverse Primer (10 µM) | 0.75 µL |
| Superscript III Platinum Taq mix | 1 µL |
| Template RNA (RNA sample) | 3 µL |
| Water to 25 µL total volume | 7 µL |

TABLE 6

| RT-PCR and Primary Amplification Program | | | |
| --- | --- | --- | --- |
| | Temperature | Time | |
| Reverse Transcription | 55° C. | 30 minutes | 45 Cycles |
| RT Inactivation | 94° C. | 2 minutes | |
| Denaturing | 94° C. | 45 seconds | |

TABLE 6-continued

| RT-PCR and Primary Amplification Program | | |
|---|---|---|
| | Temperature | Time |
| Annealing | 59° C. | 45 seconds |
| Extention | 68° C. | 1 minute |
| | 4° C. | ∞ |

Caliper Protocol:

After RT-PCR was completed, 25 uL of PCR buffer was added and the total 50 uL of reaction mixture was transferred into a Caliper plate. Caliper LabChip bioanalysis was performed based on the manufacturers' recommended protocol. The PCR product from full-length dystrophin transcript is 445 bps, and 232 bps from exon 23-skipped mRNA.

INCORPORATION BY REFERENCE

The contents of all references (including literature references, issued patents, published patent applications, and co-pending patent applications) cited throughout this application are hereby expressly incorporated herein in their entireties. Unless otherwise defined, all technical and scientific terms used herein are accorded the meaning commonly known to one with ordinary skill in the art.

Equivalents

Those skilled in the art will recognize, or be able to ascertain using no more than routine experimentation, many equivalents of the specific embodiments of the disclosure described herein. Such equivalents are intended to be encompassed by the following claims.

What is claimed is:

1. A peptide-oligonucleotide-conjugate, or a pharmaceutically acceptable salt thereof, of Formula (I):

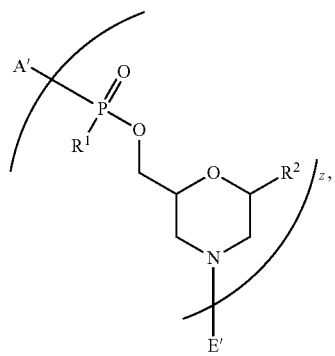

wherein:

z is 8-40;

each $R^1$ is independently selected from OH and —$NR^3R^4$, wherein each $R^3$ and $R^4$ are independently at each occurrence —$C_{1-6}$ alkyl;

each $R^2$ is independently selected from H, a nucleobase, and a nucleobase functionalized with a chemical protecting-group, wherein the nucleobase independently at each occurrence comprises pyridine, pyrimidine, triazinane, purine, or deaza-purine;

A' is selected from —$NHCH_2C(O)NH_2$, —$N(C_{1-6}$-alkyl)$CH_2C(O)NH_2$,

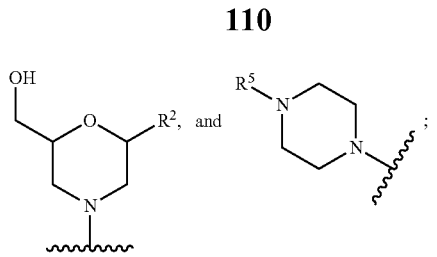

$R^5$ is —$C(O)(O$-alkyl$)_x$-OH, wherein x is 3-10 and each alkyl group is independently at each occurrence $C_{2-6}$-alkyl, or $R^5$ is selected from —$C(O)C_{1-6}$ alkyl, trityl, monomethoxytrityl, —$(C_{1-6}$-alkyl)$R^6$, —$(C_{1-6}$ heteroalkyl)-$R^6$, aryl-$R^6$, heteroaryl-$R^6$, —$C(O)O$—$(C_{1-6}$ alkyl)-$R^6$, —$C(O)O$-aryl-$R^6$, —$C(O)O$-heteroaryl-$R^6$, and -L-$(J)_t$—G;

$R^6$ is selected from OH, SH, and $NH_2$, or $R^6$ is O, S, or NH, covalently linked to a solid support;

E' is selected from H, —$C_{1-6}$ alkyl, —$C(O)C_{1-6}$ alkyl, benzoyl, stearoyl, trityl, monomethoxytrityl, dimethoxytrityl, trimethoxytrityl,

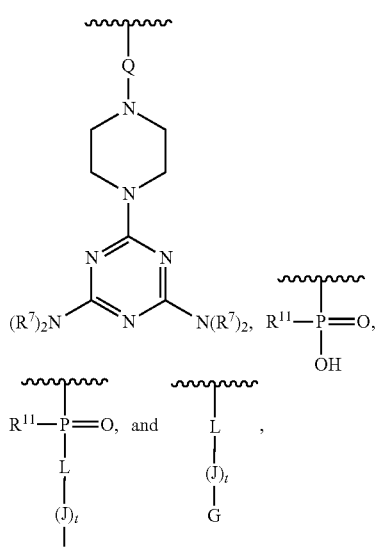

Q is —$C(O)(CH_2)_6C(O)$— or —$C(O)(CH_2)_2S_2(CH_2)_2C(O)$—, $R^7$ is —$(CH_2)_2OC(O)N(R^8)_2$;

$R^8$ is —$(CH_2)_6NHC(=NH)NH_2$;

$R^{11}$ is selected from —OH and —$NR^3R^4$;

-L-$(J)_t$—G is selected from:

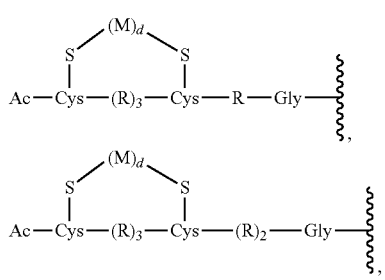

-continued

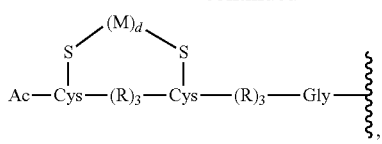,

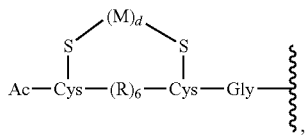,

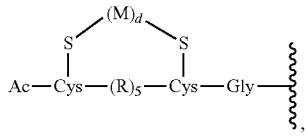,

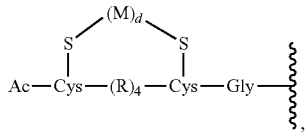,

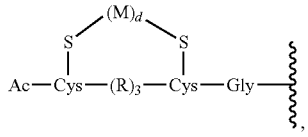, and

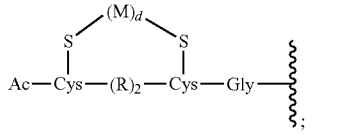;

R is arginine;
d is 0 or 1; and
M is:

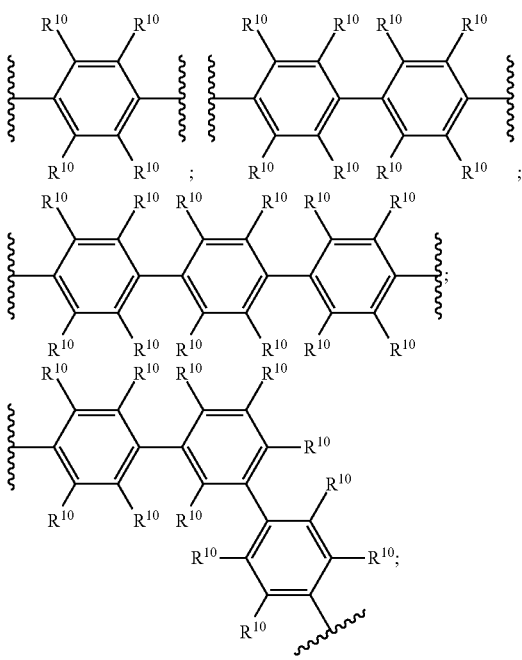

-continued

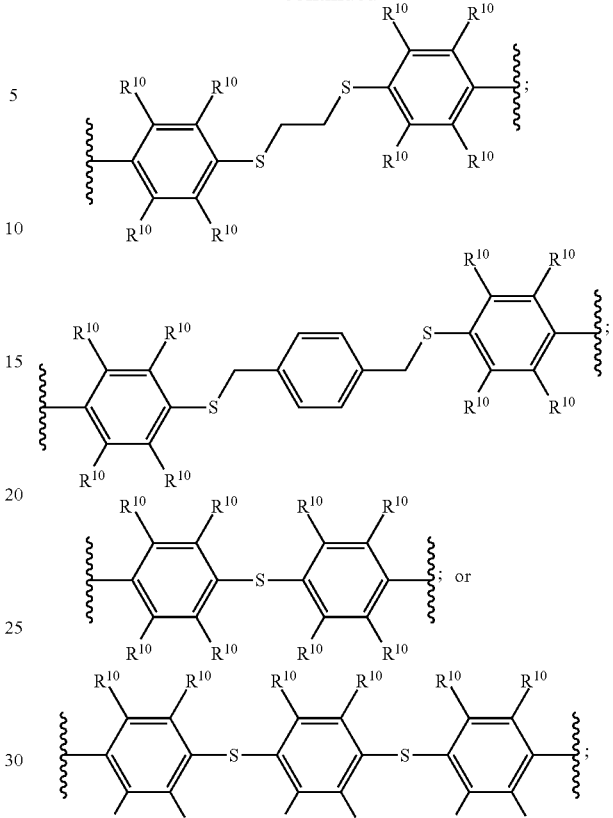

each $R^{10}$ is independently at each occurrence H or a halogen, wherein at least one of the following conditions is true:
1) A' is

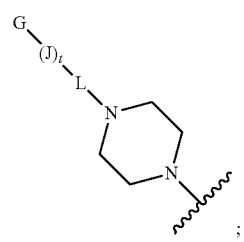;

2) E' is -L-(J)$_t$-G; or 3) E' is

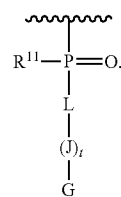

2. The peptide-oligonucleotide-conjugate of claim 1, or a pharmaceutically acceptable salt thereof, wherein E' is selected from H, —C(O) CH$_3$, trityl, 4-methoxytrityl, benzoyl, stearoyl, and -L-(J)$_t$-G.

3. The peptide-oligonucleotide-conjugate of claim 1, or a pharmaceutically acceptable salt thereof, wherein:

A' is

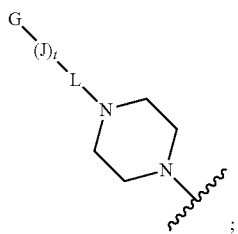

;

or

E' is -L-(J)$_t$-G.

4. The peptide-oligonucleotide-conjugate of claim 1, or a pharmaceutically acceptable salt thereof, wherein A' is selected from —N(C$_{1-6}$-alkyl)CH$_2$C(O) NH$_2$,

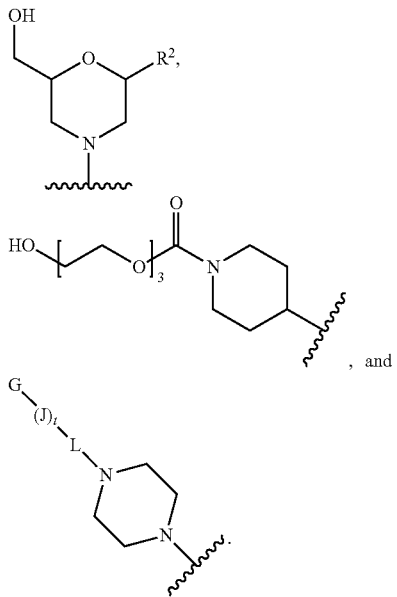

, and

5. The peptide-oligonucleotide-conjugate of claim 1, or a pharmaceutically acceptable salt thereof, wherein:

A' is

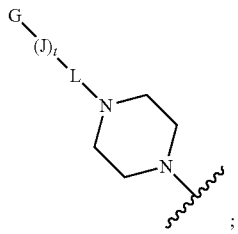

;

and

E' is selected from H, —C(O)CH$_3$, trityl, 4-methoxytrityl, benzoyl, and stearoyl.

6. The peptide-oligonucleotide-conjugate of claim 1, or a pharmaceutically acceptable salt thereof, wherein the peptide-oligonucleotide-conjugate of Formula (I) is a peptide-oligonucleotide-conjugate selected from:

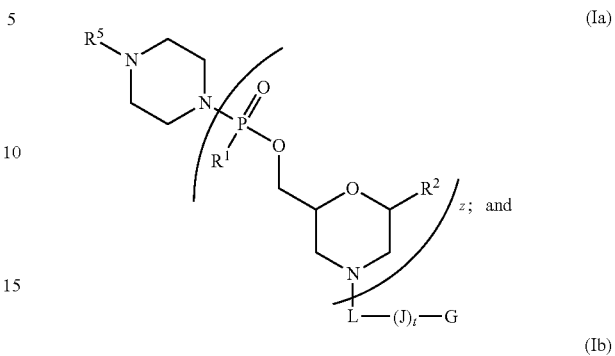

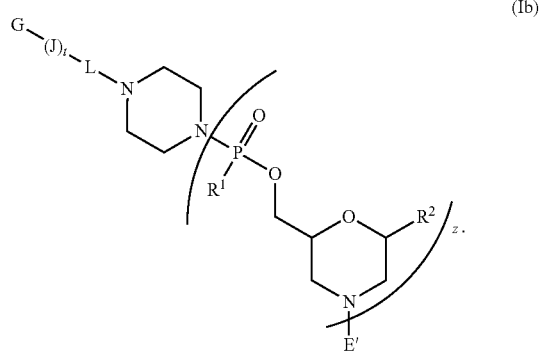

7. The peptide-oligonucleotide-conjugate of claim 6, or a pharmaceutically acceptable salt thereof, wherein the peptide-oligonucleotide-conjugate is of the Formula (Ia) and R$^5$ is —C(O)(O—CH$_2$CH$_2$)$_3$OH.

8. The peptide-oligonucleotide-conjugate of claim 6, or a pharmaceutically acceptable salt thereof, wherein the peptide-oligonucleotide-conjugate is of the Formula (Ib) and E' is selected from H, C$_{1-6}$ alkyl, —C(O)CH$_3$, benzoyl, and stearoyl.

9. The peptide-oligonucleotide-conjugate of claim 1, or a pharmaceutically acceptable salt thereof, wherein each R$^{10}$ is fluorine.

10. The peptide-oligonucleotide-conjugate of claim 1, or a pharmaceutically acceptable salt thereof, wherein M is:

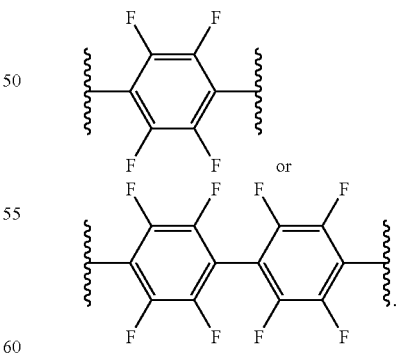

11. The peptide-oligonucleotide-conjugate of claim 1, or a pharmaceutically acceptable salt thereof, wherein z is 8-25.

12. The peptide-oligonucleotide-conjugate of claim 1, or a pharmaceutically acceptable salt thereof, wherein z is 10-20.

13. The peptide-oligonucleotide-conjugate of claim 1, or a pharmaceutically acceptable salt thereof, wherein z is 17-21.

14. The peptide-oligonucleotide-conjugate of claim 1, or a pharmaceutically acceptable salt thereof, wherein z is about 18.

15. The peptide-oligonucleotide-conjugate of claim 1, or a pharmaceutically acceptable salt thereof, wherein each $R^1$ is —$N(CH_3)_2$.

16. The peptide-oligonucleotide-conjugate of claim 1, or a pharmaceutically acceptable salt thereof, wherein each $R^2$ is a nucleobase independently at each occurrence selected from adenine, guanine, cytosine, 5-methyl-cytosine, thymine, uracil, and hypoxanthine.

17. The peptide-oligonucleotide-conjugate of claim 1, or a pharmaceutically acceptable salt thereof, wherein d is 1.

18. The peptide-oligonucleotide-conjugate of claim 1, or a pharmaceutically acceptable salt thereof, wherein d is 0.

19. The peptide-oligonucleotide-conjugate, of claim 1, or a pharmaceutically acceptable salt thereof, wherein the peptide-oligonucleotide-conjugate of Formula (I) is a peptide-oligonucleotide-conjugate of Formula (V):

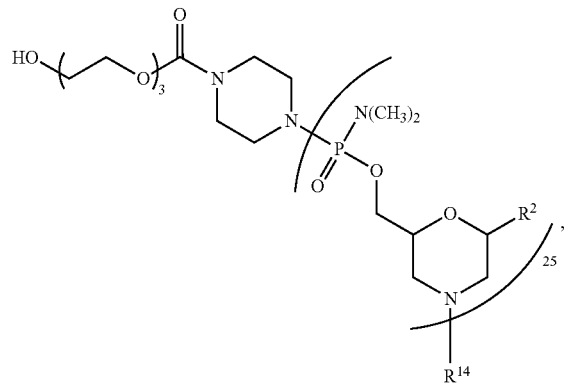

(V)

wherein $R^{14}$ is selected from:

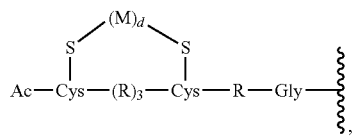

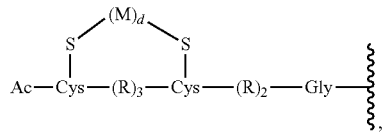

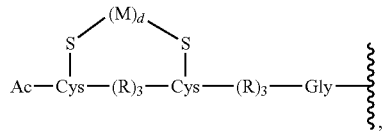

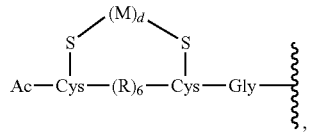

-continued

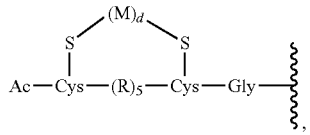

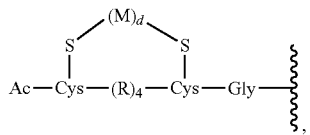

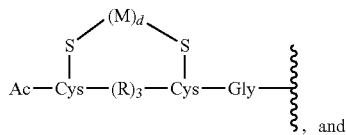

, and

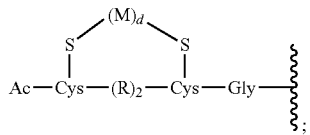

;

20. The peptide-oligonucleotide-conjugate of claim 1, or a pharmaceutically acceptable salt thereof, wherein $R^{14}$ is:

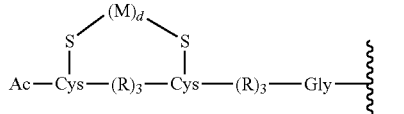

or

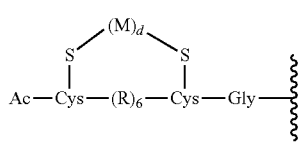

21. The peptide-oligonucleotide-conjugate of claim 1, or a pharmaceutically acceptable salt thereof, wherein:
$R^{14}$

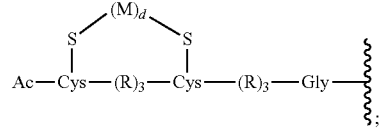

;

and
d is 0.

22. The peptide-oligonucleotide-conjugate of claim 1, or a pharmaceutically acceptable salt thereof, wherein:
$R^{14}$ is

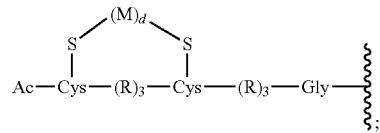

;

M is

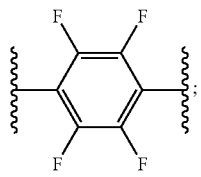 [SMILES: *c1c(F)c(F)c(*)c(F)c1F]

and d is 1.

23. The peptide-oligonucleotide-conjugate of claim 1, or a pharmaceutically acceptable salt thereof, wherein:

$R^{14}$ is

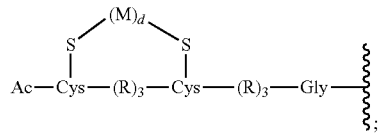

M is

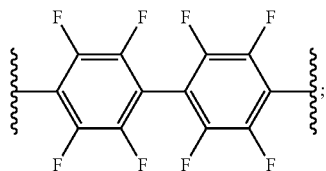

and d is 1.

24. The peptide-oligonucleotide-conjugate of claim 1, or a pharmaceutically acceptable salt thereof, wherein:

$R^{14}$ is

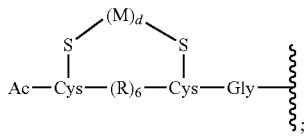

and d is 0.

25. The peptide-oligonucleotide-conjugate of claim 1, or a pharmaceutically acceptable salt thereof, wherein:

$R^{14}$ is

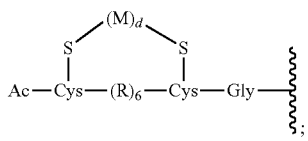

M is

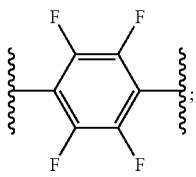 [SMILES: *c1c(F)c(F)c(*)c(F)c1F]

and d is 1.

26. The peptide-oligonucleotide-conjugate of claim 1, or a pharmaceutically acceptable salt thereof, wherein:

$R^{14}$ is

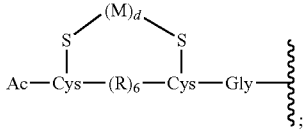

M is

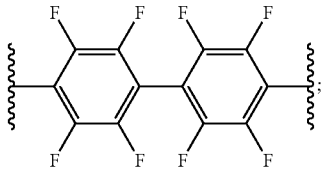 [SMILES: *c1c(F)c(F)c(-c2c(F)c(F)c(*)c(F)c2F)c(F)c1F]

and d is 1.

27. The peptide-oligonucleotide-conjugate of claim 1, or a pharmaceutically acceptable salt thereof, wherein the peptide-oligonucleotide-conjugate is:

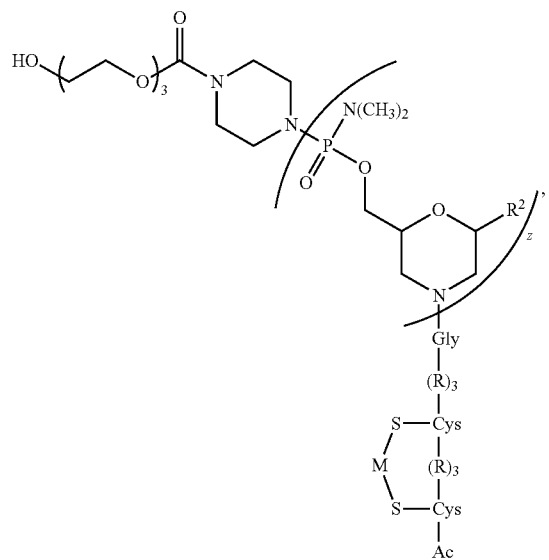

wherein:
M is
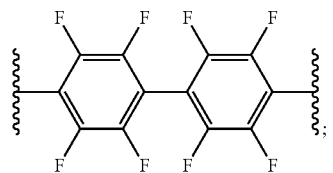 [SMILES: *c1c(F)c(F)c(-c2c(F)c(F)c(*)c(F)c2F)c(F)c1F]
and
each $R^2$ is a nucleobase independently at each occurrence selected from adenine, guanine, cytosine, 5-methylcytosine, thymine, uracil, and hypoxanthine.
* * * * *